United States Patent [19]

Yasukawa et al.

[11] Patent Number: 5,781,511
[45] Date of Patent: Jul. 14, 1998

[54] WRIST-WORN PORTABLE ELECTRONIC DEVICE

[75] Inventors: Naoaki Yasukawa; Akira Shinbo, both of Suwa; Masayuki Kawata; Kazumi Sakumoto, both of Chiba, all of Japan

[73] Assignees: Seiko Epson Corporation, Tokyo; Seiko Instruments, Inc., Chiba, both of Japan

[21] Appl. No.: 612,145

[22] Filed: Mar. 7, 1996

[30]   Foreign Application Priority Data

| Mar. 9, 1995 | [JP] | Japan | 7-050172 |
| May 12, 1995 | [JP] | Japan | 7-114964 |
| Jun. 22, 1995 | [JP] | Japan | 7-156524 |

[51] Int. Cl.⁶ ............................................. G04B 47/06
[52] U.S. Cl. ............................ 368/11; 368/10; 368/281
[58] Field of Search ....................... 368/11, 276, 10, 368/278; 73/300; 128/670

[56]   References Cited

U.S. PATENT DOCUMENTS

| 2,771,559 | 11/1956 | Montmeat | 368/224 |
| 2,771,560 | 11/1956 | Creiman | 368/224 |
| 3,831,449 | 8/1974 | MacNiel et al. | 73/300 |
| 4,280,506 | 7/1981 | Zurcher | |
| 4,312,358 | 1/1982 | Barney | 128/736 |
| 4,629,329 | 12/1986 | Komiyama | 386/10 |

FOREIGN PATENT DOCUMENTS 60-29296   2/1985   Japan .

*Primary Examiner*—Bernard Roskoski
*Attorney, Agent, or Firm*—Mark P. Watson

[57]   ABSTRACT

A wrist-worn portable electronic device comprises a main unit having a display member for displaying information including time, etc., a wrist band connected to the main unit for allowing a user to wear the device on the wrist, and a connector mechanism for allowing signals to be input to the main unit. The connector mechanism comprises a connector member disposed on an edge of the main unit at a 6 o'clock or 12 o'clock position of the main unit and a connector piece for removably coupling to the connector member. The connector member includes a first terminal group comprising a plurality of terminals. The connector piece includes a second termination group comprising a plurality of terminals for electrically connecting to the first terminal group. The second terminal group receives signals for inputting to the main unit. In the wrist-worn portable electronic device, the connector mechanism allows easy attachment and detachment of a cable, etc., to the main unit. Therefore, the wrist-worn portable device can be used as a regular wrist watch in daily use by just removing the cable, etc., from the main unit. Also, since the connector mechanism is disposed on the surface of the edge where the wrist band attaches to the main unit, the connector mechanism does not protrude from the main unit in the 3 o'clock direction. Therefore, the wrist can be moved freely. Also, since the connector mechanism does not protrude from the main unit in the 3 o'clock or 9 o'clock direction, the user's hand will not come in contact with the connector mechanism even if the user should stumble. For this reason, since the connector mechanism will not be damaged while being safe for the user, high reliability is maintained and ease of use is enhanced.

37 Claims, 21 Drawing Sheets

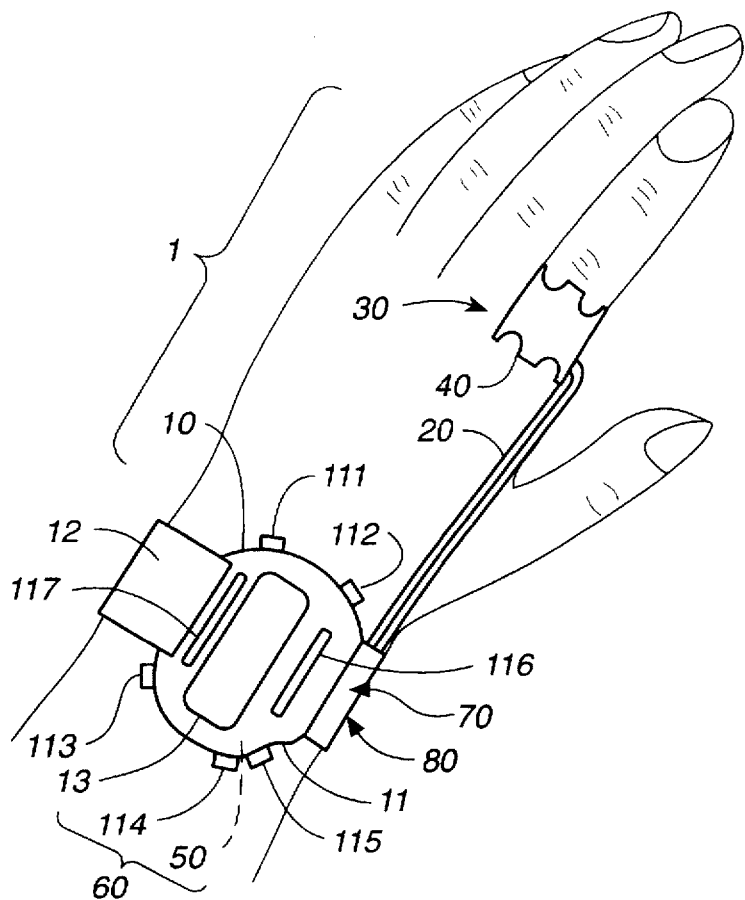
FIG._1A
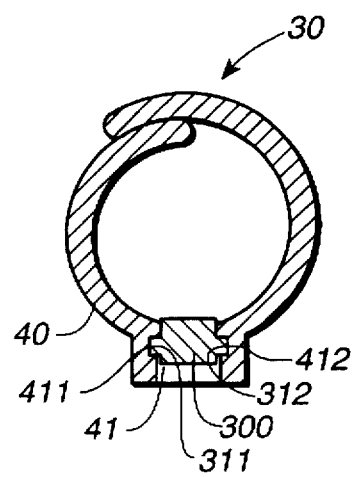
FIG._1B

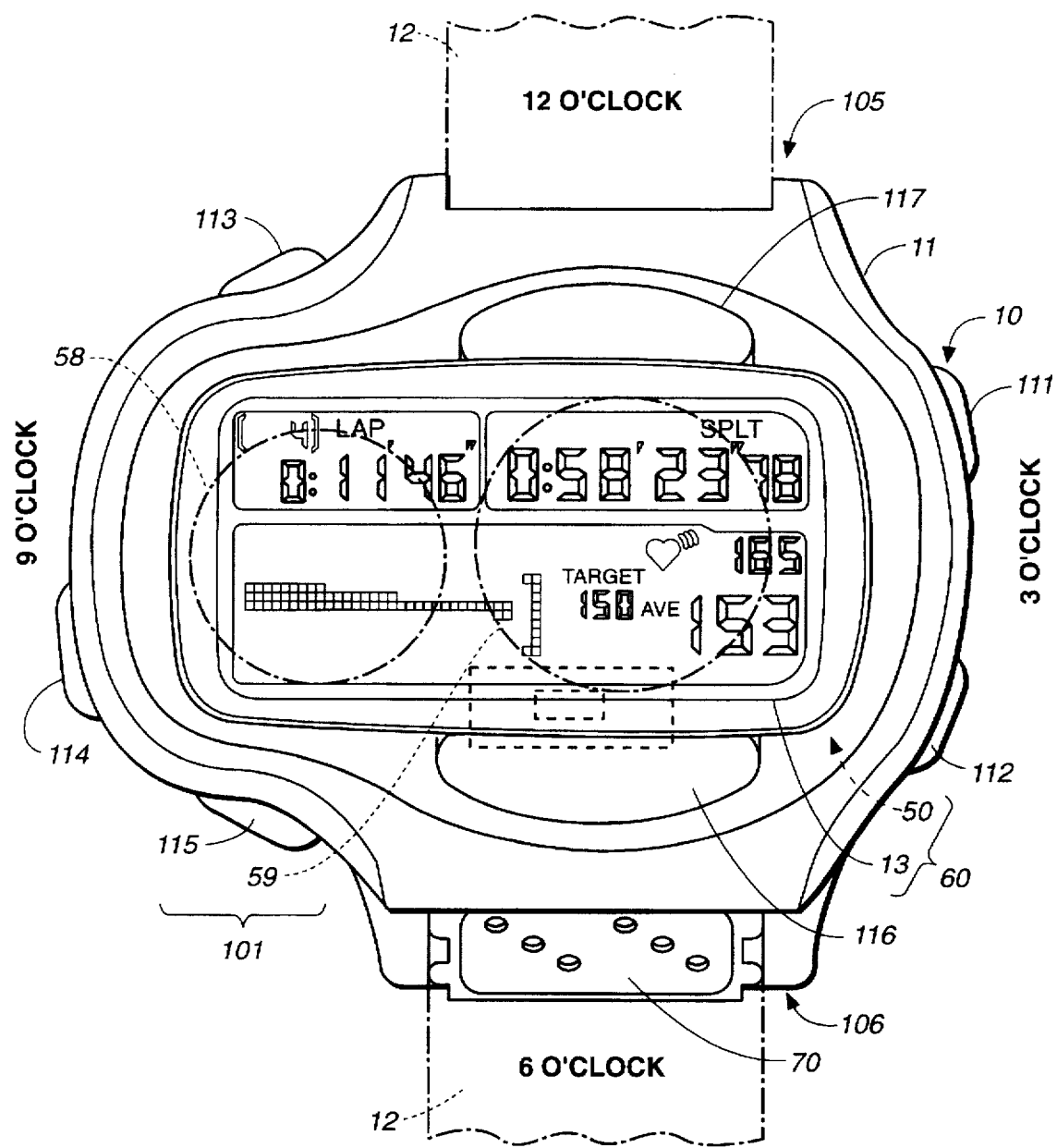
FIG._2

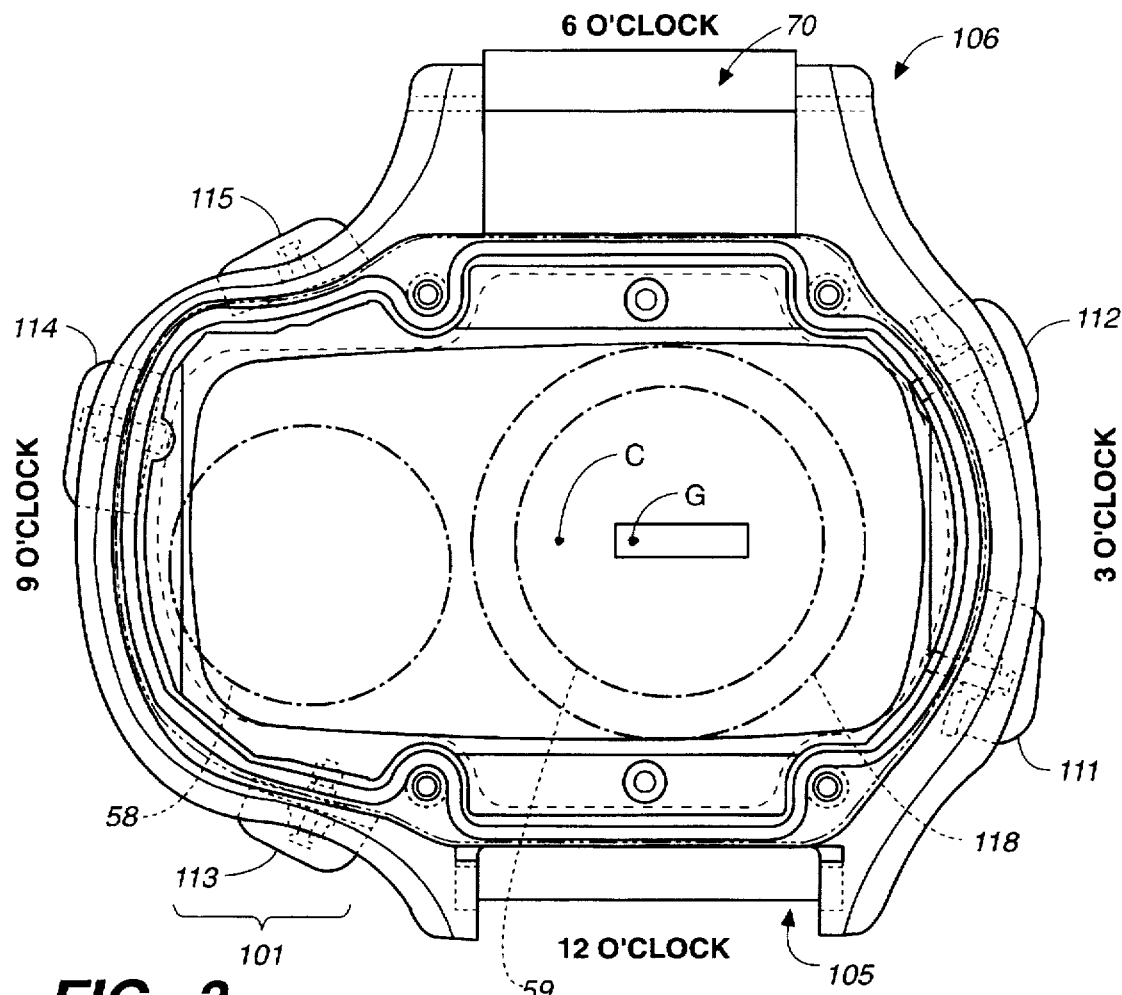
FIG._3
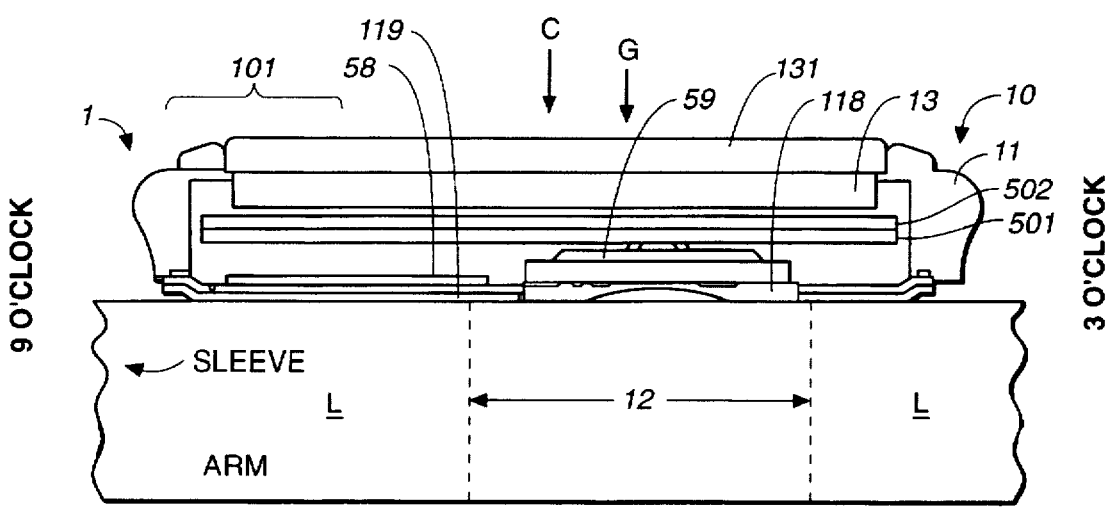
FIG._4

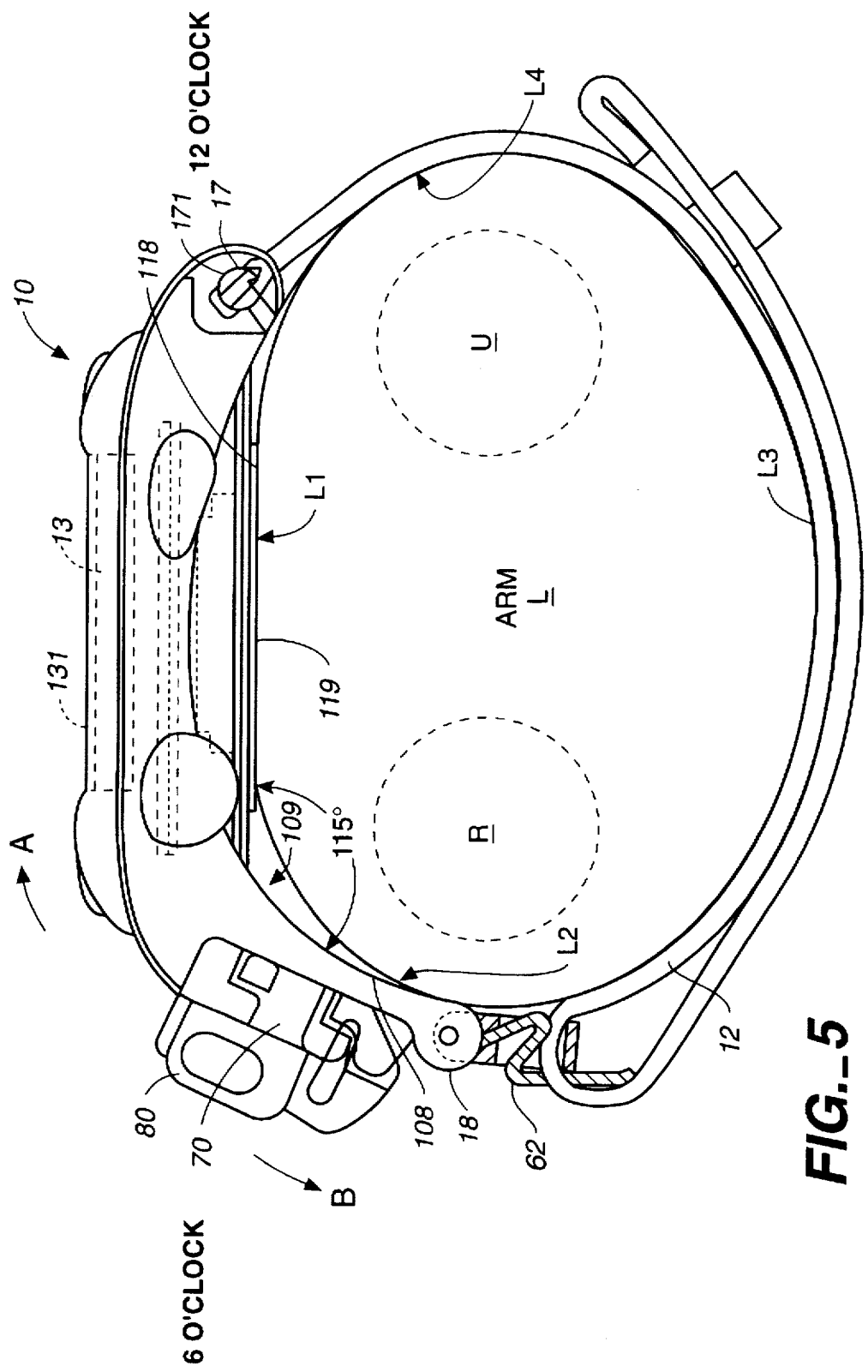
FIG._5

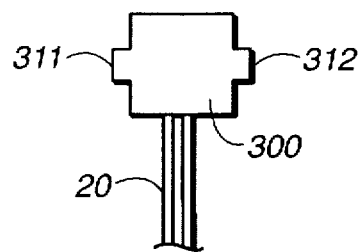
FIG._6A
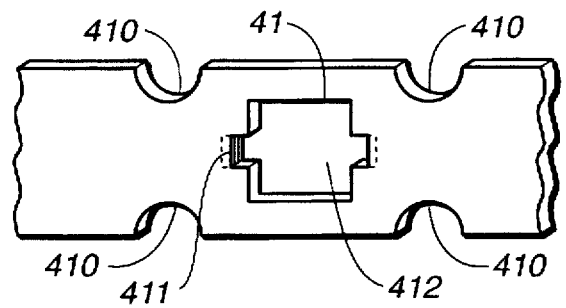
FIG._6B
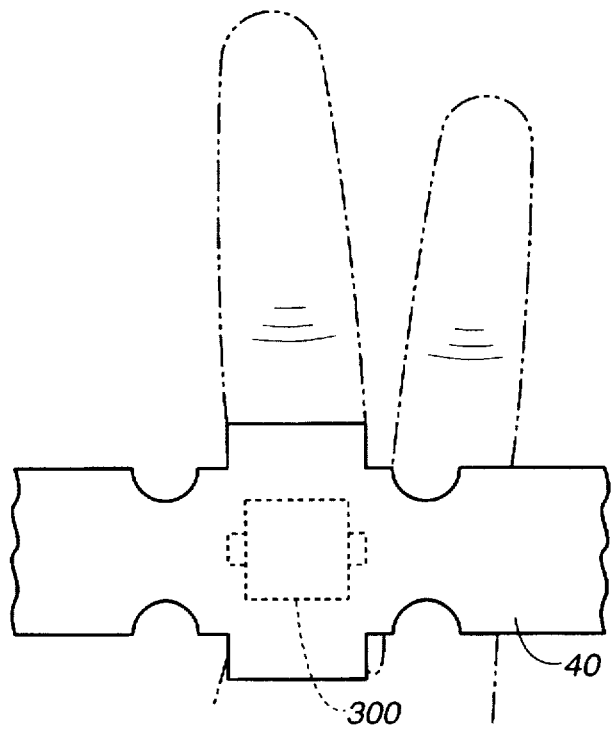
FIG._6C

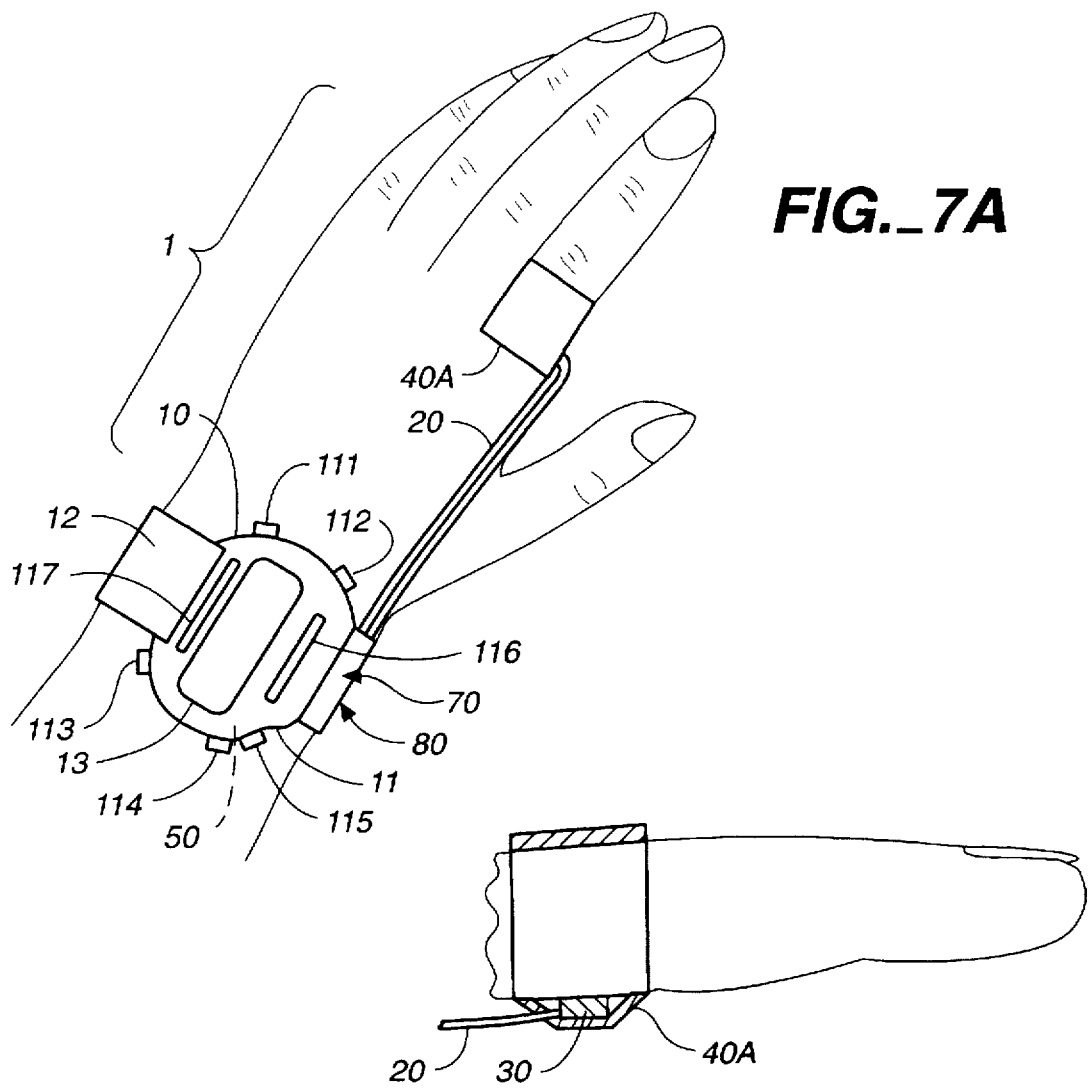
FIG._7A
FIG._7B
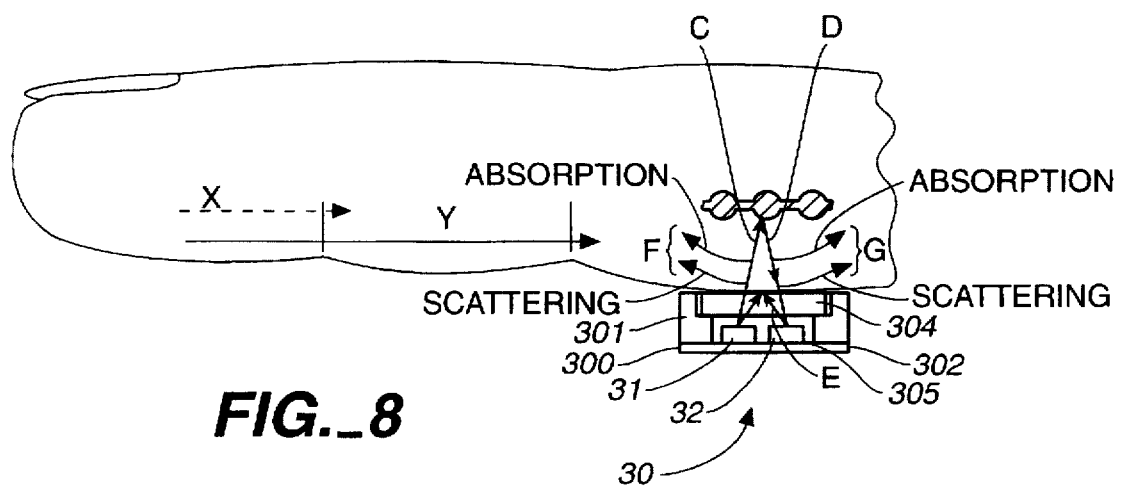
FIG._8

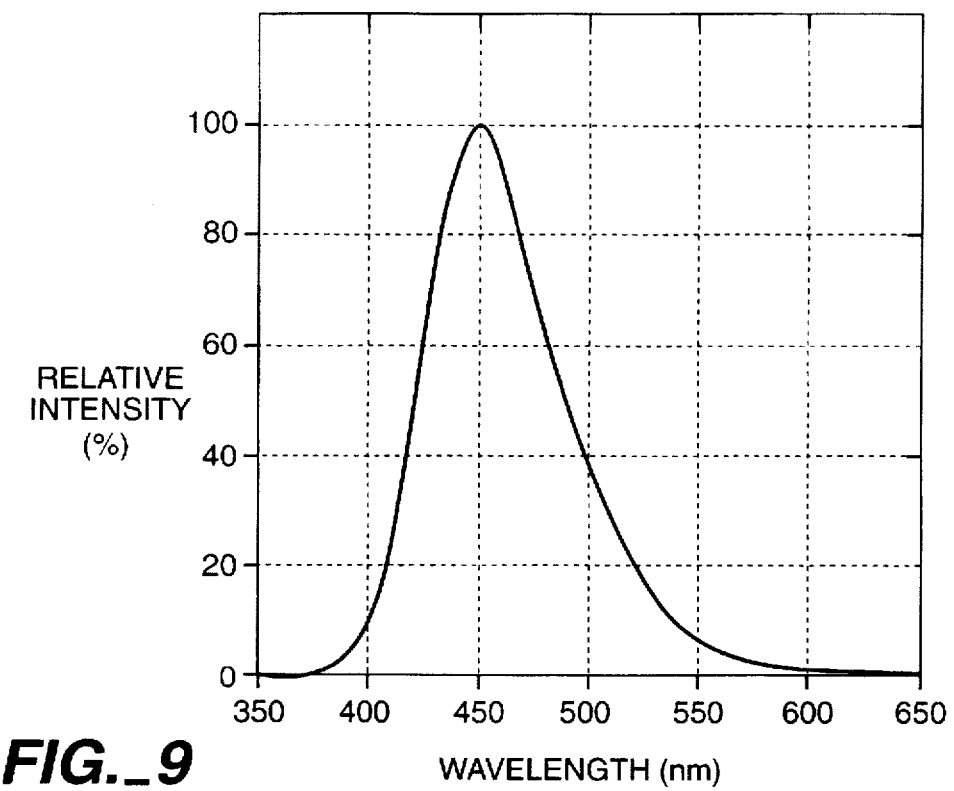
FIG._9
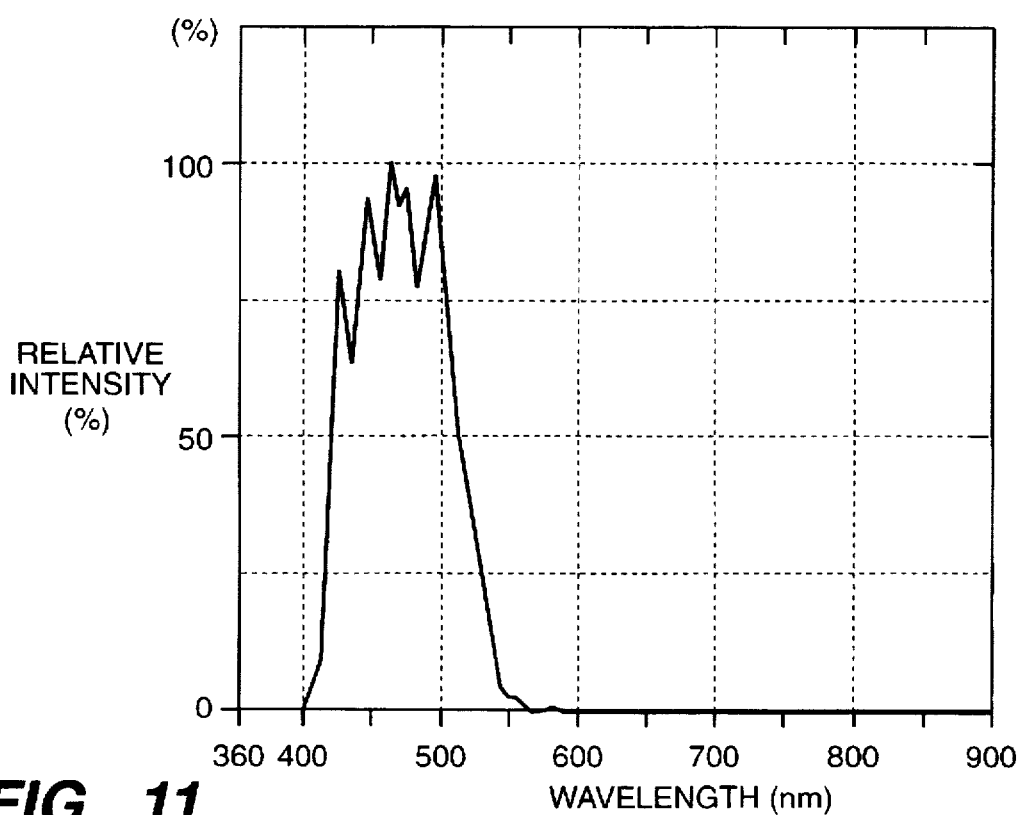
FIG._11

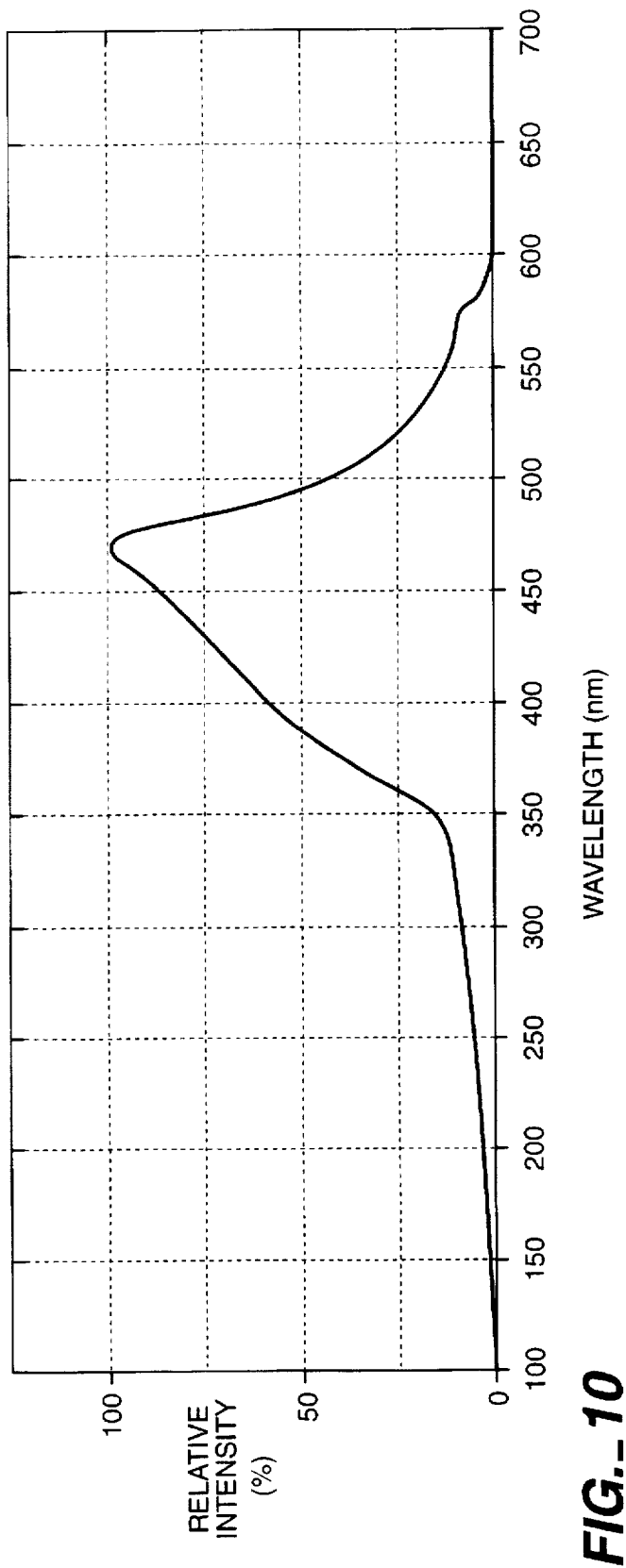
FIG._10
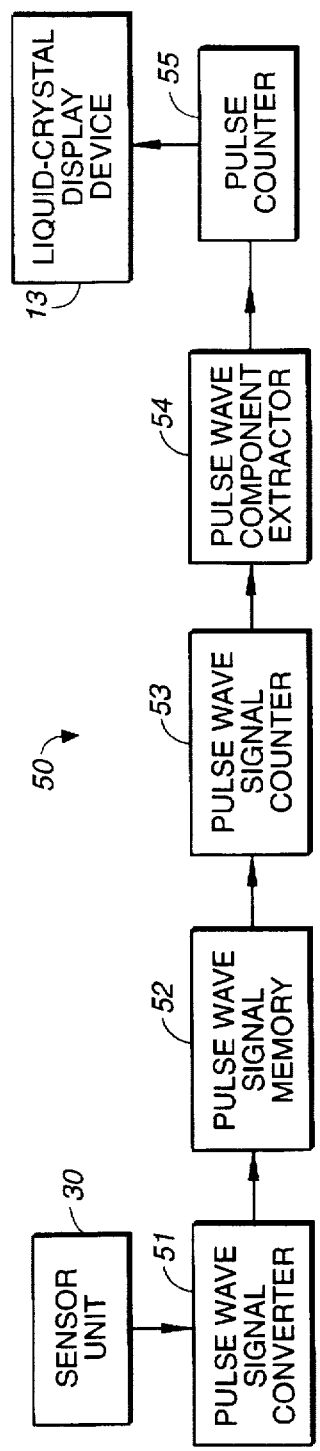
FIG._12

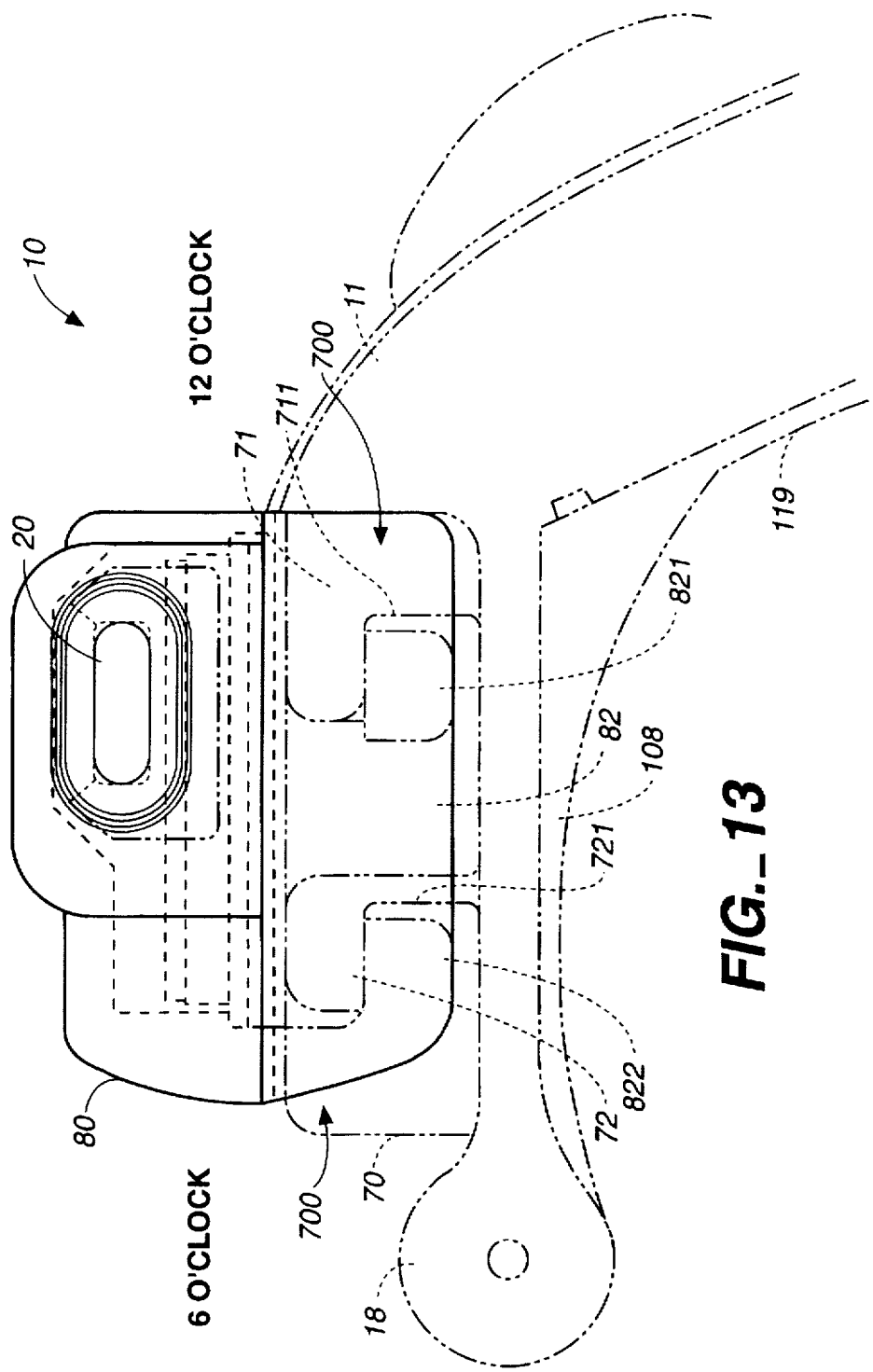
FIG._13

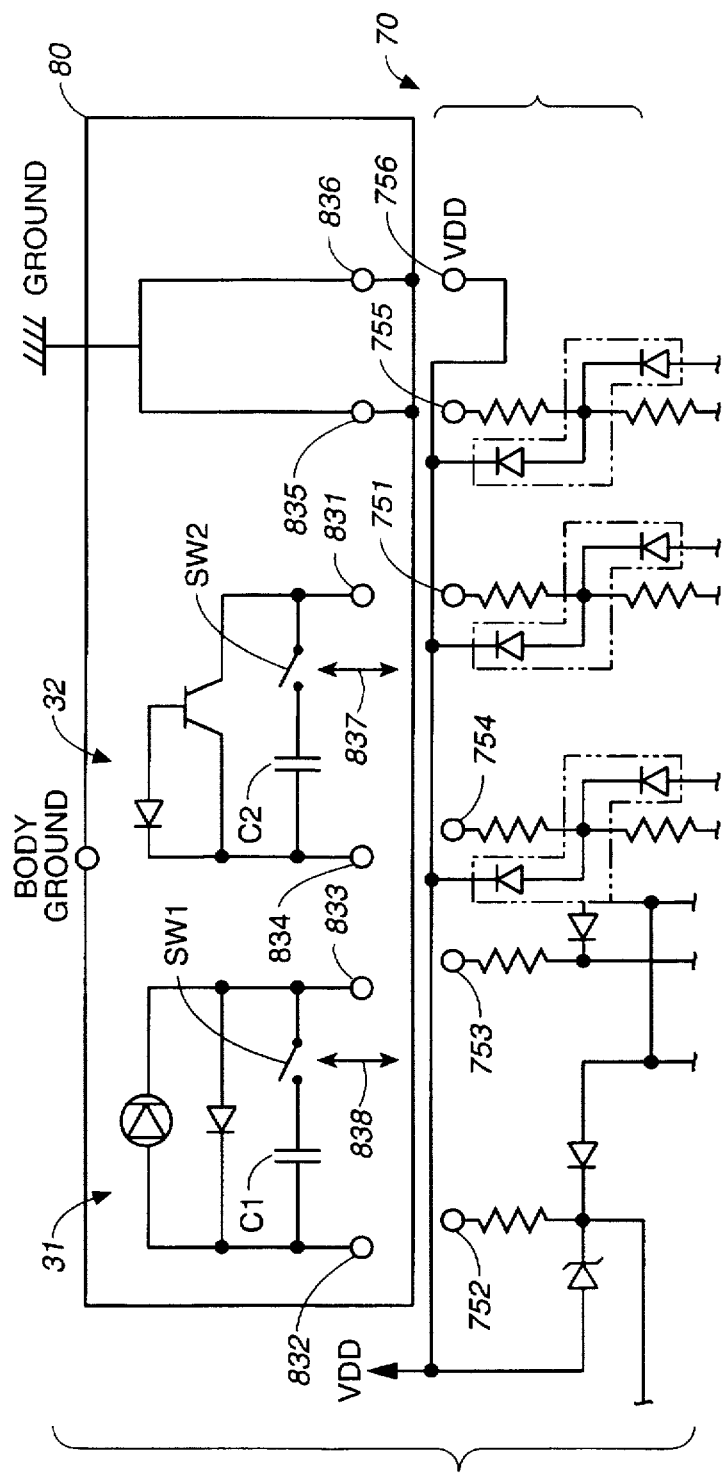
FIG._14

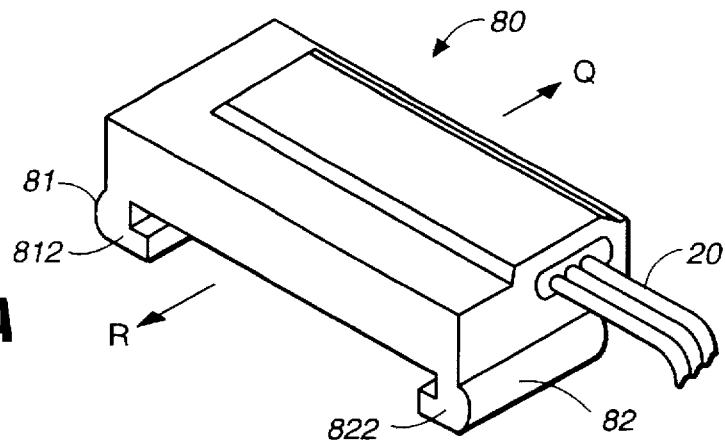
FIG._15A
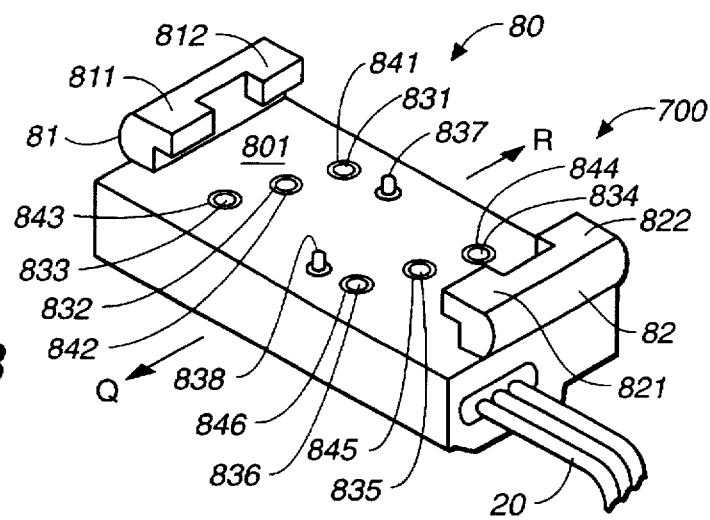
FIG._15B
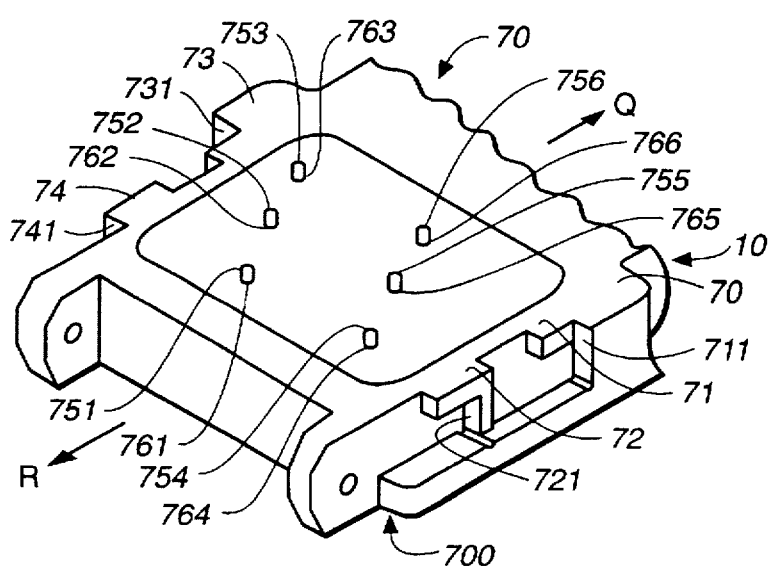
FIG._16

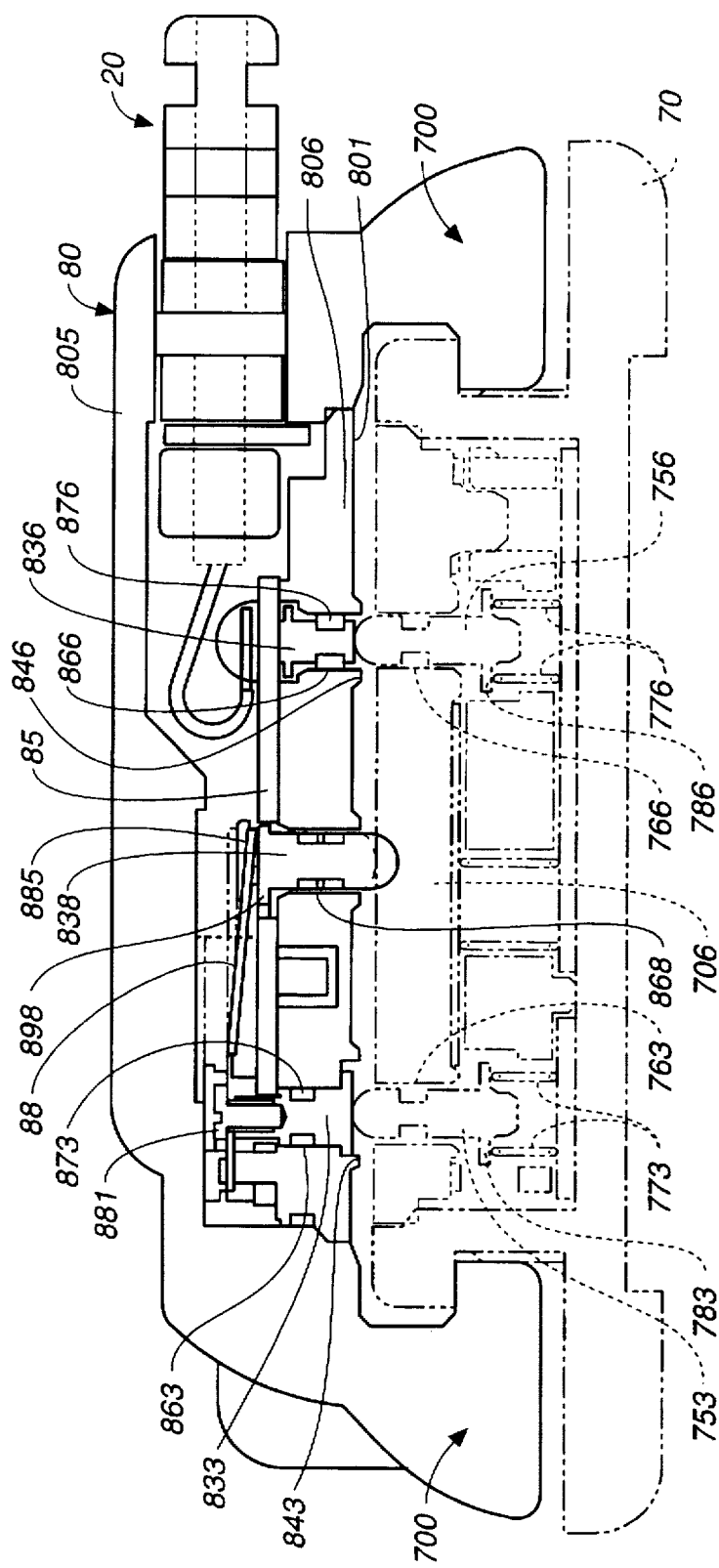
FIG._17

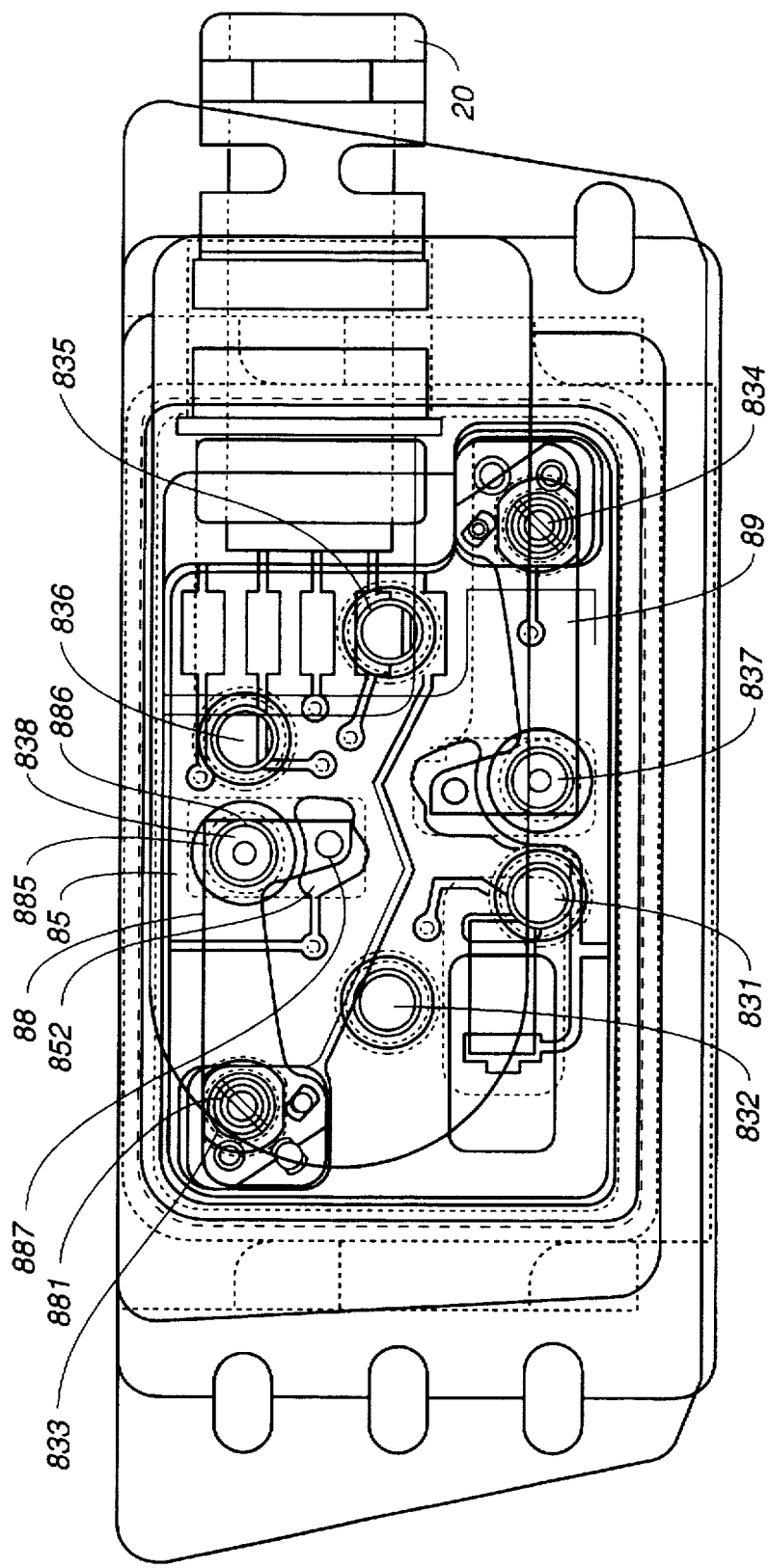
FIG._18

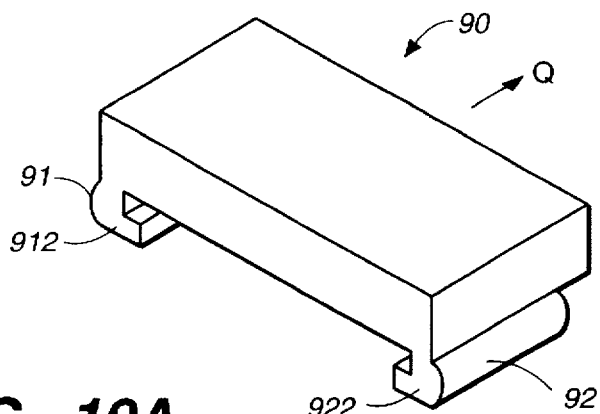
FIG._19A
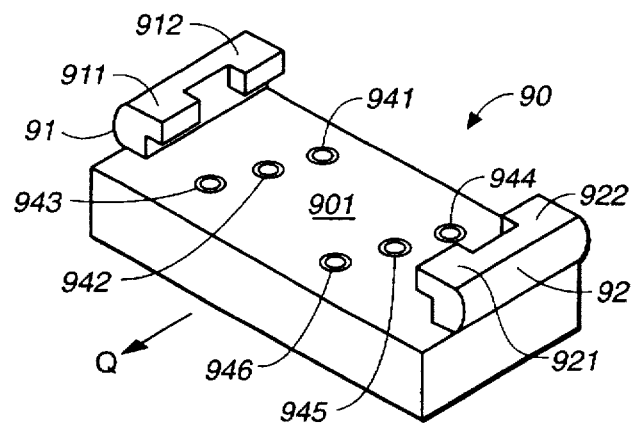
FIG._19B
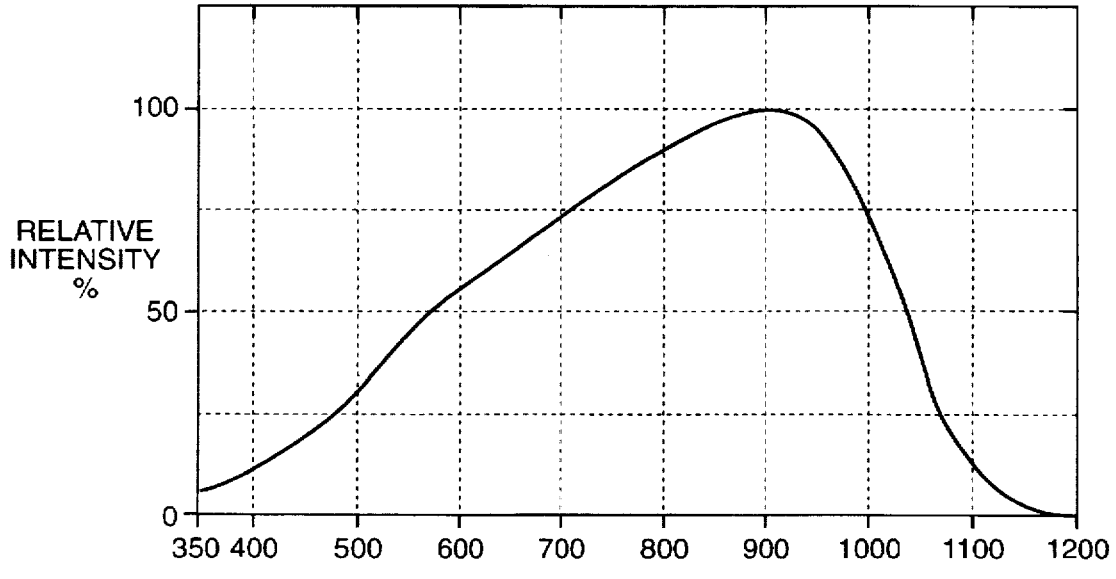
FIG._21

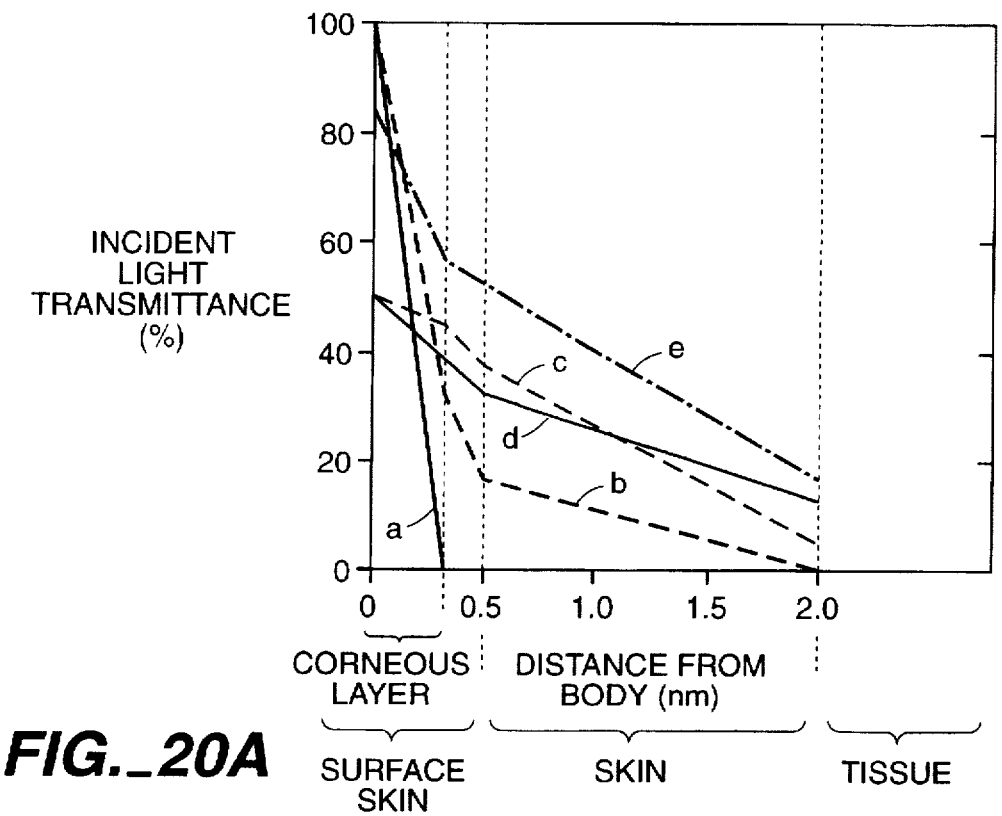
FIG._20A
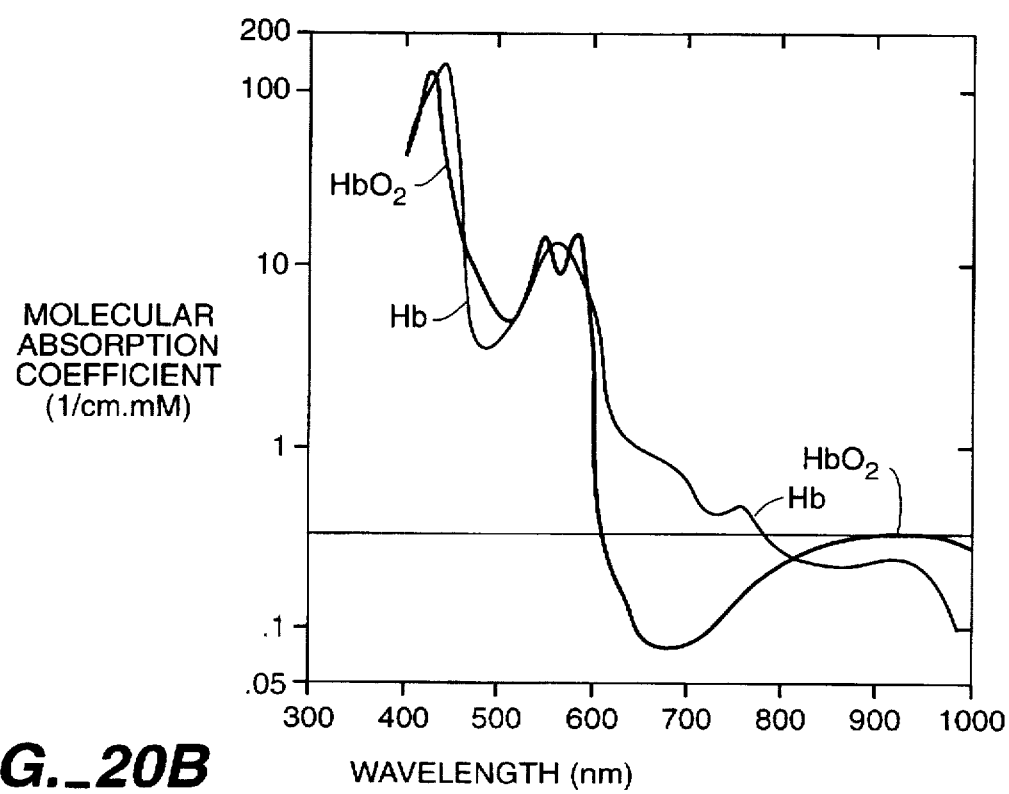
FIG._20B

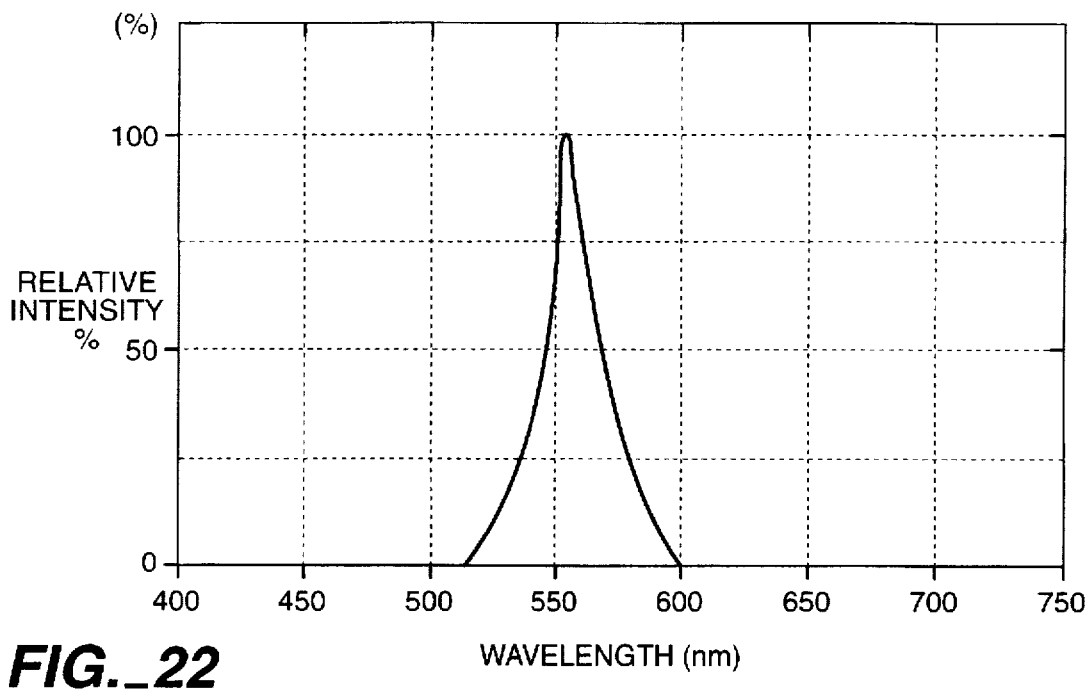
FIG._22
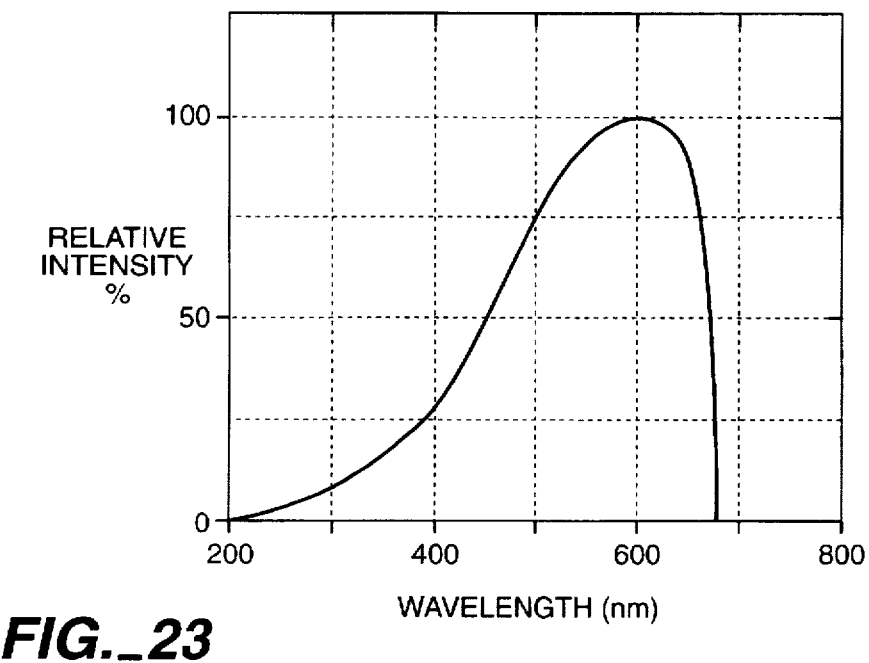
FIG._23

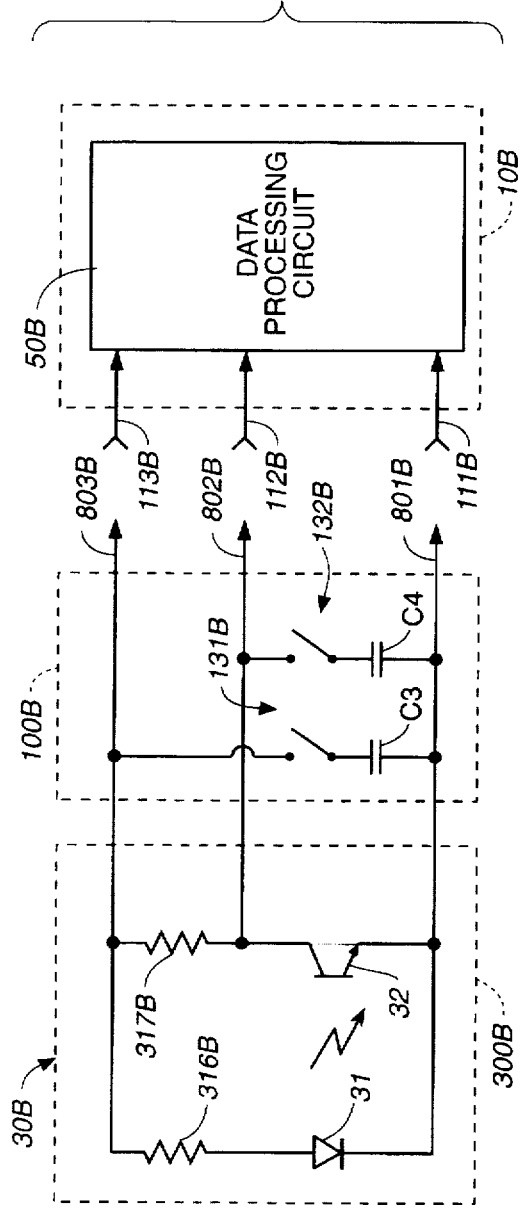
FIG._24
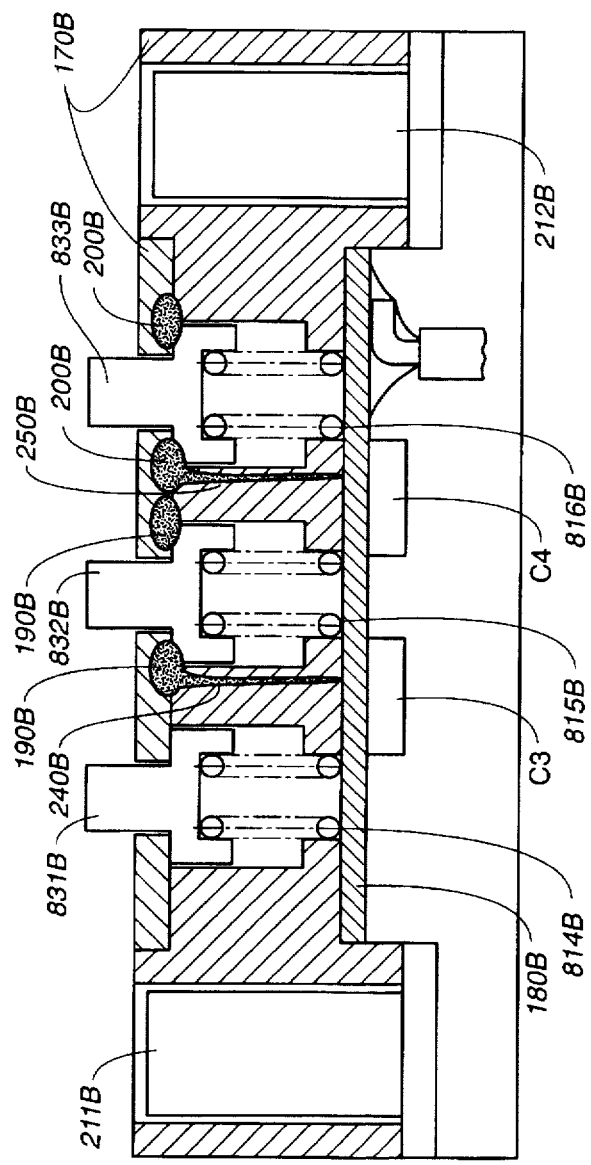
FIG._25

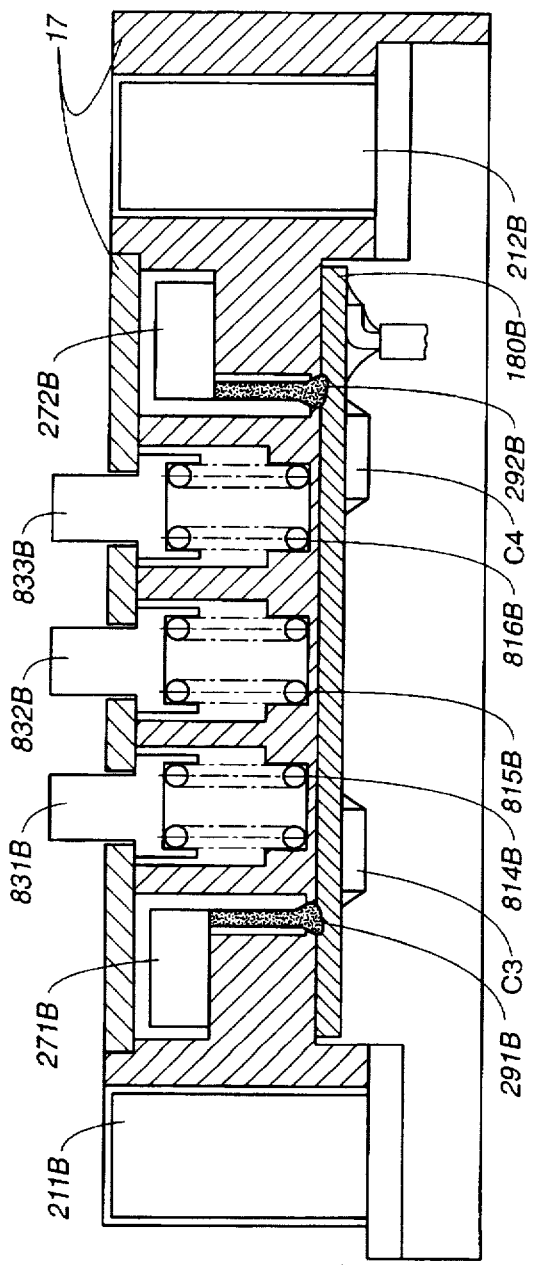
FIG._26
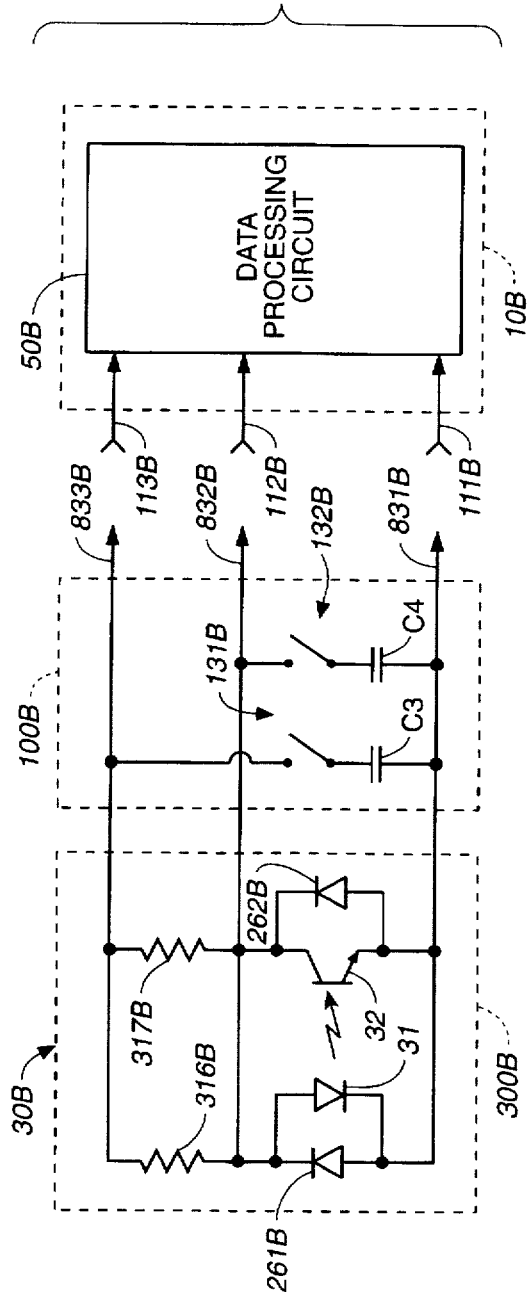
FIG._27

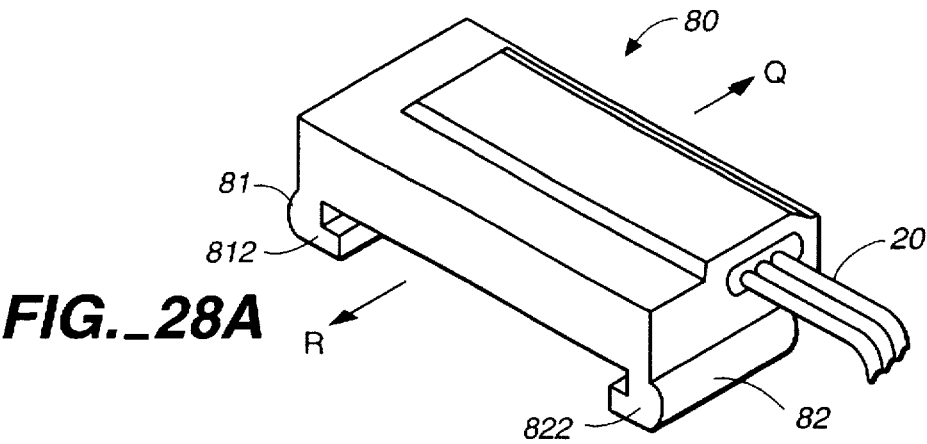
FIG._28A
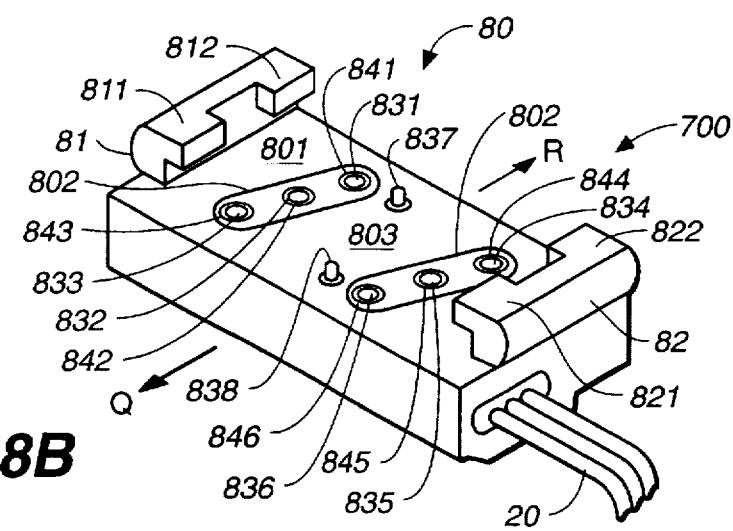
FIG._28B
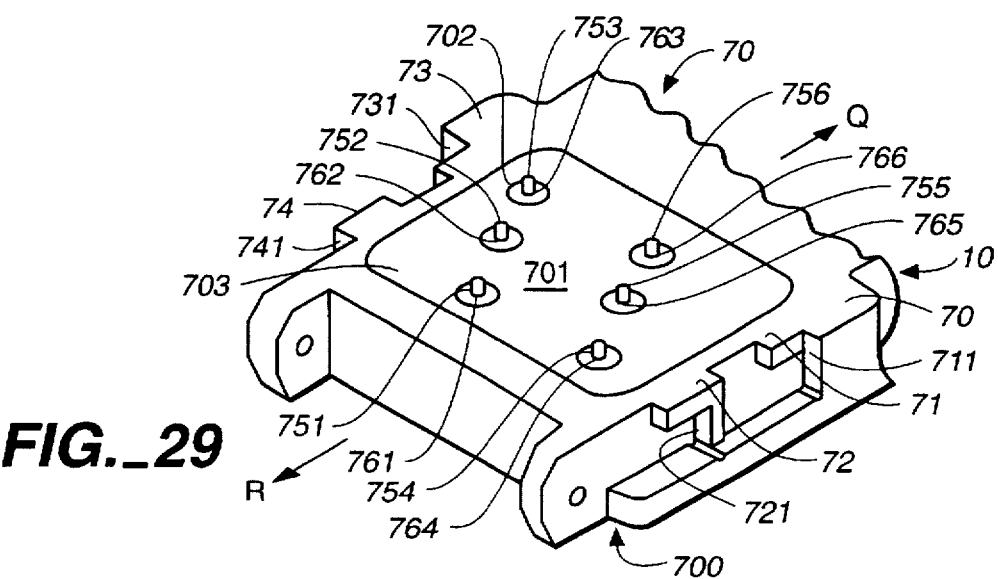
FIG._29

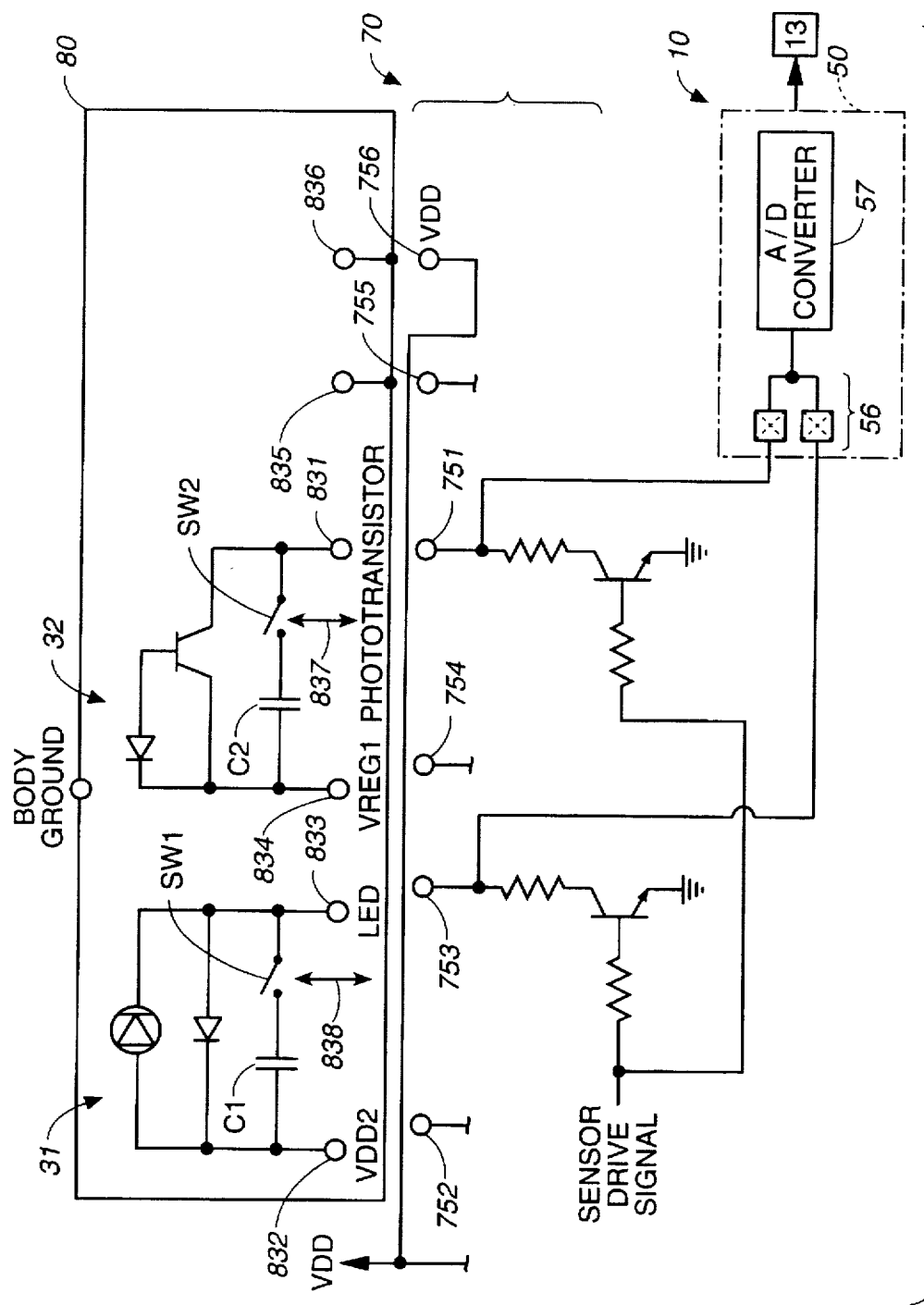
FIG._30

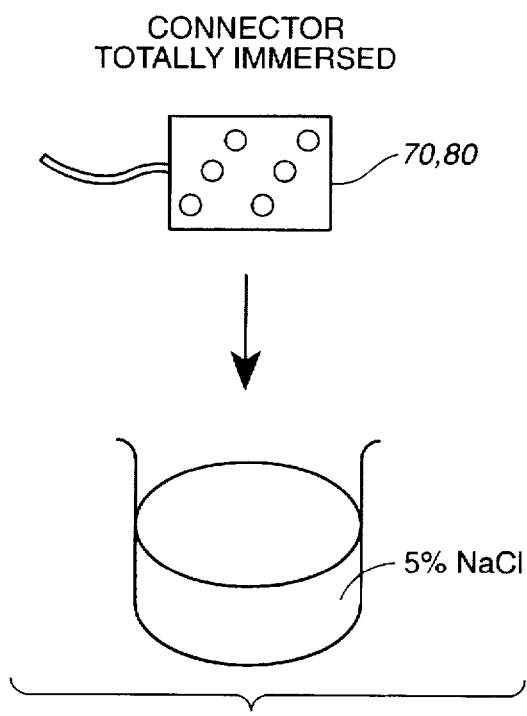
FIG._31A
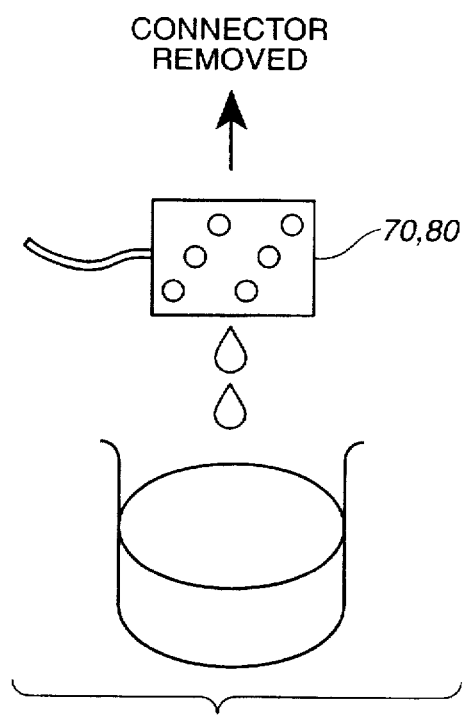
FIG._31B
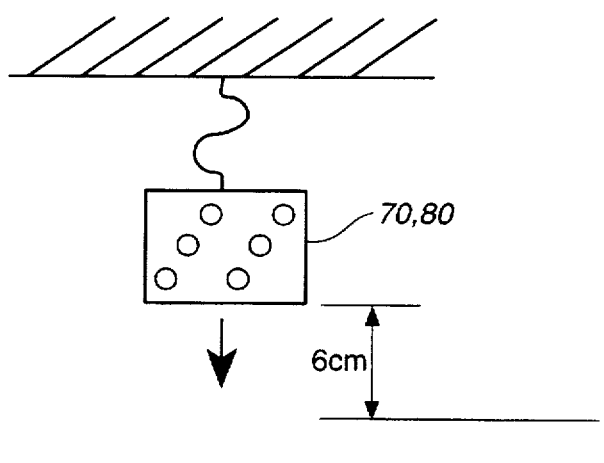
FIG._31C
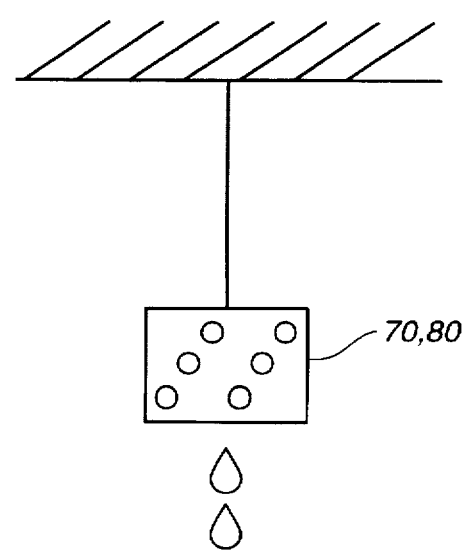
FIG._31D

WRIST-WORN PORTABLE ELECTRONIC DEVICE

BACKGROUND OF THE INVENTION

1. Field of the Invention

This invention relates to a wrist-worn portable electronic device with a connector mechanism for connecting a sensor unit or other external device to the portable electronic device. More particularly, it relates to a connector mechanism for assuring reliability in a wrist-worn portable electronic device.

2. Description of the Related Art

Devices that measure the pulse wave count or other pulse wave information include devices that optically detect the change in the amount of blood and display pulse wave information based on a pulse wave signal. These optical type pulse wave measuring devices are configured such that a sensor unit with an LED (light-emitting diode) or other light-emitting element and a photodiode, a phototransistor or other photoreceptor element are mounted on a finger, and that part of the light emitted from the LED that is reflected back from the finger (blood vessel) is received by the phototransistor. The change in the amount of blood is detected by the change in the amount of light and the pulse, etc., and is sought based on this detection result. Detection of the pulse signal is not limited to the finger and may be performed by irradiating light from the LED on a wrist or other body part and detecting the scattered light with the photodiode. In either case, in an optical pulse wave measurement device, a photoelectric pulse wave detection sensor is used that irradiates light on body tissue and detects the resulting scattered light.

In recent years, pulse wave measurement devices capable of measuring the pulse while jogging or running have come into demand. Here, the inventors propose a wrist-worn portable electronic device that is a wrist-worn portable pulse wave measurement device whose main unit is attached to the wrist by means of a wrist band. Further, the inventors proposed the addition of a watch function to the main unit and making the wrist-worn portable electronic device a multifunction type device by making it possible to measure lap times while jogging or running.

However, in such wrist-worn portable electronic devices, even though they may have a watch function, devices in which a cable extends from the main unit or a sensor unit or another external device is integrated in the main unit are difficult to use as wrist watches in daily use.

Wrist-worn portable electronic devices having a connector mechanism at the 3 o'clock position of the main unit of the wrist watch for connecting to a cable or sensor unit can be considered, but a wrist-worn portable electronic device with this kind of structure has a protruding structure from the main unit toward the hand (3 o'clock position on wrist watch) to accommodate the connector mechanism. This causes the connector mechanism to interfere with the arm whenever the wrist is bent. This makes the device uncomfortable to wear and the connector mechanism may come off easily. Therefore, when a connector system is used, the ease of use may be improved, but the reliability of the wrist-worn portable electronic device is poor.

Further, when a structure is used in the wrist-worn portable electronic device that connects the main unit to a separate sensor unit via a connector mechanism, the terminals that connect the LED, photodiode or other semiconductor elements from among the sensor circuits built into the sensor unit are left exposed in the connector when the sensor unit is detached from the main unit. If static electricity is discharged on these exposed terminals in this type of structure, the semiconductor elements may be damaged by the static electricity. Therefore, the ease of use may be improved when a connector system is used, but the reliability of the wrist-worn portable electronic device is poor.

Further, when a connector piece is attached that covers the connector on the main unit, a narrow gap occurs between the top surface of the connector and the bottom surface of the connector piece. Therefore, if water comes in contact with this part, capillary action causes the water to travel all the way in, resulting in a short circuit between terminals. Moreover, since water that enters like this will not come out by just shaking the connector, the connector piece must be removed each time and the water carefully cleaned out or else the unit will not recover from the short-circuit condition.

In view of these problems, the invention offers a wrist-worn portable electronic device that maintains a high level of reliability and ease of use is improved by using a structure which connects a sensor unit or other external device to the main unit via a connector mechanism.

The invention also offers a wrist-worn portable electronic device that protects the semiconductor elements built into the sensor unit, etc., from static electricity, whereby a high level of reliability is maintained and ease of use is improved by providing a connector mechanism.

The invention also offers a wrist-worn portable electronic device that prevents the occurrence of a short circuit between terminals in the connector due to the intrusion of water, whereby a high level of reliability is maintained and ease of use is improved by providing a connector mechanism.

SUMMARY OF THE INVENTION

In order to solve the above problems, this invention features a wrist-worn portable electronic device comprising a main unit having a display member for displaying information, including time, etc., a wrist band connected to the main unit for allowing a user to wear the device on the wrist and a connector mechanism for allowing signals to be input to the main unit. The connector mechanism comprises a connector member disposed on an edge of the main unit at one of the 6 o'clock or 12 o'clock position of the main unit and a connector piece for removably coupling to the connector member. The connector member includes a first terminal group comprising a plurality of terminals. The connector piece includes a second terminal group comprising a plurality of terminals for electrically connecting to the first terminal group. The second terminal group receives signals for inputting to the main unit.

In this invention, a reference to a position of a certain time on the main unit indicates only a position on the main unit and does not mean that the display on the main unit is a hand type display.

A wrist-worn portable electronic device configured in this way uses a connector mechanism that allows free attachment and detachment of a cable, etc., to the main unit. Therefore, the wrist-worn portable device can be used as a regular wrist watch in daily use by just removing the cable, etc., from the main unit. Also, of the edges of the main unit, the connector mechanism is disposed on the edge at the 6 o'clock or 12 o'clock position on the main unit. That is, it is disposed on the surface of the edge where the wrist band attaches to the main unit. Therefore, since the connector mechanism does not protrude from the main unit in the 3 o'clock direction, the wrist can be moved freely. Also, since the connector mechanism does not protrude from the main unit in the 3 o'clock or 9 o'clock direction, the user's hand will not come in contact with the connector mechanism even if the user should stumble. For this reason, since the connector mechanism will not be damaged while being safe for the user, high reliability is maintained and ease of use is enhanced by using a structure that connects a sensor unit or other external device to the main unit via a connector mechanism.

In this invention, it is desirable the connector mechanism include a latching mechanism that latches the connector piece to the connector member when the connector piece is slid on the connector member in a predetermined sliding direction and holds them in a latched condition. The latching mechanism releases the latched condition when the connector piece is slid in an opposite direction from the sliding direction.

By using this configuration, the connector member and connector piece become securely latched and the cable will not become inadvertently detached during running. Therefore, the wrist-worn portable electronic device of this invention can be conveniently used as a pulse meter to measure pulse, for example, during running without worry and also as a watch.

In this invention, it is desirable that, on an edge of the main unit, the connector member be formed on the edge surface at the 6 o'clock position on the main unit. The latching mechanism becomes latched when the connector piece is slid on the connector member in the direction from 6 o'clock to 12 o'clock on the main unit and becomes connected to the connector member. By using this configuration, the connector mechanism is positioned in the front when the main unit is placed on the wrist, thus facilitating attachment and detachment.

When this type of latching mechanism is used, it is desirable that the first terminal group be disposed in a plurality of rows along the predetermined sliding direction of the connector piece and be formed in positions shifted between the terminals in a direction crossing the sliding direction. The second terminal group may be formed in positions shifted between the terminals in a direction crossing the predetermined sliding direction of the connector piece such that it corresponds with the positions at which the first terminal group is formed.

By using this configuration, the first terminal group and second terminal group are disposed in a plurality of rows along the sliding direction of the connector piece and the positions are shifted between the terminals in a direction crossing the sliding direction. Therefore, as the connector piece is slid on the connector member, non-corresponding terminals will not come in contact with each other. Also, even if the surface area forming the connector member is small, terminals can be separated from each other, thus making it difficult for terminals to short-circuit even if water should enter between the connector piece and the connector member.

In this invention, the latching mechanism may include, for example, a first protrusion group connected to the connector member for latching. The first protrusion group includes a plurality of protrusions disposed such that at least two protrusions project outward from the connector member in each of the 3 o'clock and 9 o'clock directions on the main unit. The latching mechanism also includes a pair of protruding members connected to the connector piece and each protruding down from one side of the connector piece. The protruding members are positioned outside the first protrusion group when the connector piece is attached to the connector member. Moreover, the latching mechanism includes a second protrusion group connected to the protruding members for latching. The second protrusion group includes a plurality of protrusions disposed such that they protrude inward from the protruding members. In a latching operation, the second protrusion group passes between the first protrusion group by a first action that fits the connector piece on the connector member. The second protrusion group slides to the respective positions under the first protrusion group by a second action that slides the connector piece on the connector member in the sliding direction, so that the connector member and the connector piece are coupled together. By using this configuration, latching can be performed reliably and easily.

In this invention, it is desirable that the connector mechanism includes a first stopper mechanism connected to the connector member for stopping the connector piece at an attachment position on the connector member when the second operation is performed and a second stopper mechanism connected to the connector member for stopping the connector piece at a preset position when slid in the direction opposite from the second operation when removing the connector piece from the connector member, so as to allow the second protrusion group to pass between the first protrusion group when the operation opposite from the first operation is performed. By using this configuration, the user can attach and detach the connector piece to and from the connector member without looking.

In this invention, it is desirable that the connector mechanism include through holes on either the bottom surface of the connector piece or on the top surface of the connector member, moving pins capable of moving in the holes and springs attached to the moving pins for pushing the moving pins in the direction that causes the ends of the moving pins to protrude from the holes. The terminals of either the first or second terminal group are configured with the moving pins. By using this configuration, a reliable electrical connection between the first terminal group and the second terminal group is achieved.

In this invention, it is desirable that the terminals of the first or second terminal group which are for electrically connecting to the moving pins have round protruding members disposed around a position where the moving pins are positioned when the connector piece is attached to the connector member. The moving pins, the springs and the protruding members of the terminals constitute a click mechanism that causes the moving pins to ride up on the protruding members when the connector piece is attached to the connector member.

In this invention, from the standpoint of protection of the connector member when the connector piece is removed, in addition to the connector piece, there is a connector cover having essentially the same mechanism as the connector piece that attaches on the connector member such that it covers the connector member surface.

In this invention, it is desirable that a switch mechanism be provided on the connector piece for automatically closing and opening contact in conjunction with the attachment and detachment operations of the connector piece on the connector member.

This switch mechanism may be configured to include a plurality of through holes on the bottom surface of the connector piece, moving pins capable of moving in the holes to cause their ends to protrude from the holes, and springs attached to the moving pins for pushing the pins in a direction that causes the moving pins to protrude from the surface of the connector piece. For example, it automatically closes and opens contact based on the movement of the moving pins in the holes. By using this configuration, the switch mechanism that is linked to the attachment operation of the connector piece to the connector member can be easily configured and its operation is reliable.

Also, by providing a magnetic reed switch in the connector piece that magnetically detects the attachment and detachment of the connector piece on the connector member, the switch mechanism can automatically close and open contact in conjunction with the attachment and detachment of the connector piece on the connector member.

This type of wrist-worn portable electronic device may also include a cable that connects to the connector piece and a sensor unit that inputs the detection results to the main unit via the cable and the connector piece.

For example, by providing the sensor unit with a light-emitting element that irradiates light toward a body and a photoreceptor element that detects light returning from the body, the wrist-worn portable electronic device of this invention can be a portable pulse wave measuring device. In this portable pulse wave measuring device, the sensor unit inputs the detection results of the photoreceptor element to the main unit via the cable and the main unit displays pulse wave measurement results in the display member.

The wrist-worn portable electronic device may also include a capacitance element in either the connector piece or the sensor unit for protecting the semiconductor elements that make up the sensor from static electricity when the capacitance element is electrically connected to the semiconductor elements in parallel. The switch mechanism changes to a state in which the capacitance element is electrically connected to the semiconductor elements in parallel when the connector piece is removed from the connector member, and this state of the switch mechanism is canceled when the connector piece is attached to the connector member.

By using this configuration, the connection state of the capacitance element can be switched between the standby mode and normal mode (pulse wave measuring mode). That is, in the state in which the connector piece is detached from the connector member, the capacitance element is electrically connected in parallel to the semiconductor elements, i.e., light-emitting element and photoreceptor element, and therefore the semiconductor elements can be protected from static electricity. But since the state in which the capacitance element is electrically connected to the semiconductor elements in parallel can be released in the state in which the connector piece is detached from the connector member, the device can be used normally. Also, since the charge stored in the capacitance element up until the connector piece is attached to the connector member is not discharged from the capacitance element to the main unit, the circuit in the main unit can be protected. Therefore, a high level of reliability is maintained and ease of use is improved by using a structure which connects a sensor unit or other external device to the main unit via a connector mechanism. Moreover, since the connection state of the capacitance element can be automatically switched between a standby mode and a normal mode (pulse wave measurement mode), it is convenient while reliably protecting the light-emitting element or the photoreceptor element.

Here, it is desirable that the connector piece or the sensor unit include a diode to prevent an excessive reverse current from flowing to the semiconductor elements when the diode is electrically connected to the semiconductor elements in parallel.

Further, by providing the sensor unit with a light-emitting element that irradiates light toward a body and a photoreceptor element that detects light returning from the body as the semiconductor element, the device can be used as a pulse wave measuring device. In this pulse wave measurement device, the sensor unit inputs the detection results output by the photoreceptor element to the main unit via the cable, whereby the main unit displays the pulse wave measurement results in the display member.

In this invention, it is desirable that a surface of the connector member or the connector piece have a structure that prevents short circuits between terminals. For example, it is desirable that on at least one surface of the surfaces facing each other on the connector member and connector piece, the contact angle of water in a first area around the terminals of one of the first and second terminal groups be greater than the contact angle of water in a second area surrounding the first area.

When the connector piece is attached so that it covers the connector member, the terminal groups become electrically connected and the top surface of the connector member and the bottom surface of the connector piece face each other with a small gap between them. If the connector should come in contact with water, capillary action will cause water to travel into the gap. Here, the contact angle of water in the first area around the terminals is larger than the contact angle of water in the surrounding area.

That is, the contact angle $\Theta$ obtained by the equation $$\Theta = 2 \tan^{-1}(h/r)$$

$\Theta$: contact angle
h: height of water drop
r: radius of water drop based on the diameter and height of the water drop when a water drop is on the bare material is equivalent to the angle formed by the liquid on the bare material and the bare material surface. Therefore, it becomes an indicator of the wettability of the liquid (hydrophilic property) and water repellence (hydrophobic property) of the liquid. Here, in a comparison of the first area around the terminals and the second area surrounding this first area in this invention, the first area is hydrophobic while the second area is hydrophilic. Therefore, even if water should enter in the gap between the connector member and the connector piece, water near the terminals is prevented from entering the first area around the terminals and is pulled toward the surrounding area. Therefore, short circuits do not occur between terminals. Also, even if a short-circuit condition should occur temporarily, the short-circuit condition can be cleared by shaking the connector piece. Therefore, even if rain water gets on the device, a short circuit will not readily occur between the terminals, and even if a short-circuit condition should occur temporarily, the short-circuit condition can be easily cleared by just shaking the wrist. Therefore, this device is suited to pulse wave measurement during running outside.

In this invention, it is desirable that the contact angle of water in the first area around the terminals be greater than the contact angle of water in the surrounding area on both opposing surfaces of the connector member and the connector piece. In this way, it is possible to more reliably prevent short circuits and more easily recover from a short-circuit condition.

In this invention, it is desirable that the difference between the contact angle of water in the first area around the terminals and the contact angle of water in the second area surrounding the area around the terminals be greater than 50 degrees.

In this connector structure, it is desirable that the first area around the terminals undergo hydrophobic treatment and that the surrounding area undergo hydrophilic treatment. Rather than changing the type of material that makes up the connector member or the connector piece in just the first area around the terminals or the surrounding area, subjecting the first area around the terminals to hydrophobic treatment and the surrounding area to hydrophilic treatment makes it possible to increase the difference between the contact angles of water in these areas.

Also, the structure of the opposing surfaces of the connector member and the connector piece for preventing short circuits between terminals can be configured such that the contact angle of water in the first area around the terminals is greater than the contact angle of water in the second area surrounding this first area on at least one surface of the surfaces facing each other on the connector member and the connector piece when a contact angle of water is evaluated with fatty oil applied.

By using this configuration, if the contact angle of water in the first area around the terminals is larger than the contact angle of water in the surrounding area when the connector member and the connector piece are handled by hand and the hand comes in contact with them and causes fatty oil (finger prints) to adhere to them, the occurrence of short circuits can be reliably prevented and it is easy to recover from a short-circuit condition. Therefore, even if a short-circuit condition should occur temporarily, it can be easily recovered by simply shaking the wrist, thus making this device is suited to pulse wave measurement during running outside.

Here, it is desirable that the contact angle of water in the first area around the terminals be greater than the contact angle of water in the second area surrounding the first area on both surfaces facing each other on the connector member and connector piece when a contact angle of water is evaluated with fatty oil applied.

In order to obtain this difference in the contact angle of water in a condition in which fatty oil is applied, the first area around the terminals can be made smooth and the second area surrounding the first area can be made rough. When the presence and absence of roughness is utilized to achieve a difference in contact angle, the molds used to form the connector member and the connector piece need only be treated.

In this case, it is desirable that the main unit include a short-circuit detection means that measures the electric potential of at least the terminals of the first terminal group to which signals are input from the sensor unit when the connector piece is attached to the connector member. The short-circuit detection means detects whether or not there is a short-circuit condition between the terminals of the first terminal group and the terminals of the sensor unit for receiving a drive voltage. The detection result is displayed on the display member.

By using this configuration, it can be determined immediately whether a short circuit is the cause of a problem, and therefore the user can quickly shake his wrist, etc., to recover from the problem and quickly return the device to a normal condition.

Other objects and attainments together with a fuller understanding of the invention will become apparent and appreciated by referring to the following description and claims taken in conjunction with the accompanying drawings.

BRIEF DESCRIPTION OF THE DRAWINGS

FIGS. 1A and 1B are explanatory diagrams showing how the wrist-worn portable electronic device of the first embodiment of the invention is used.

FIG. 2 is a plan view of the main unit of the wrist-worn portable electronic device shown in FIGS. 1A and 1B.

FIG. 3 is a bottom plan view of the main unit of the wrist-worn portable electronic device shown in FIGS. 1A and 1B.

FIG. 4 is an explanatory diagram showing the main unit of the wrist-worn portable electronic device shown in FIGS. 1A and 1B as seen from the 6 o'clock direction on the watch.

FIG. 5 is a side elevation showing the main unit of the wrist-worn portable electronic device shown in FIGS. 1A and 1B as seen from the 3 o'clock direction on the watch.

FIG. 6 is a plan view of the optical unit of the sensor unit used in the wrist-worn portable electronic device shown in FIGS. 1A and 1B; FIG. 6B is a plan view showing the sensor attachment band of the sensor unit used in this wrist-worn portable electronic device in the open position; and FIG. 6C is an explanatory diagram showing the structure of another sensor unit.

FIGS. 7A and 7B are explanatory diagrams showing how another sensor attachment band is used in the wrist-worn portable electronic device of the first embodiment of the invention.

FIG. 8 is an explanatory diagram showing the sensor unit in the wrist-worn portable electronic device shown in FIGS. 1A and 1B attached to the finger.

FIG. 9 is an explanatory diagram showing the light-emitting spectrum of an InGaN type blue LED used in the wrist-worn portable electronic device shown in FIGS. 1A and 1B.

FIG. 10 is an explanatory diagram showing the photoreceptor characteristic of an InGaP type phototransistor used in the wrist-worn portable electronic device shown in FIGS. 1A and 1B.

FIG. 11 is an explanatory diagram showing the photoreceptor characteristic of a filter-equipped phototransistor used in the wrist-worn portable electronic device shown in FIGS. 1A and 1B.

FIG. 12 is a block diagram showing the functions of the data processing circuit in the wrist-worn portable electronic device shown in FIGS. 1A and 1B.

FIG. 13 is an enlarged view of the connector member of the wrist-worn portable electronic device shown in FIGS. 1A and 1B as seen from the 3 o'clock direction on the watch.

FIG. 14 is an explanatory diagram showing the electrical connection in the connector member in the wrist-worn portable electronic device shown in FIGS. 1A and 1B.

FIGS. 15A and 15B are explanatory diagrams showing the structure of the connector piece (connector piece on sensor unit side) used in the connector mechanism shown in FIG. 13.

FIG. 16 is an explanatory diagram showing the structure of the connector member (connector member on main unit side) used in the connector mechanism shown in FIG. 13.

FIG. 17 is a cross section showing the connector piece shown in FIGS. 15A and 15B connected to the connector member shown in FIG. 16.

FIG. 18 is a plan view showing the disposition of the electrodes on the connector piece shown in FIGS. 15A and 15B.

FIGS. 19A and 19B are explanatory diagrams showing the configuration of the connector cover that covers the connector member in place of the connector piece in the wrist-worn portable electronic device shown in FIGS. 1A and 1B.

FIG. 20A is a graph showing the relationship between the wavelength of the light and the light transmittance of the skin; and FIG. 20B is an explanatory diagram showing the relationship between the wavelength of the light and the absorption characteristic of each type of hemoglobin.

FIG. 21 is an explanatory diagram showing the photoreceptor characteristic of the silicon type phototransistor used in a prior art wrist-worn portable electronic device.

FIG. 22 is an explanatory diagram showing the light-emitting spectrum of GaP type LED used in the wrist-worn portable electronic device shown in FIGS. 1A and 1B.

FIG. 23 is an explanatory diagram showing the photoreceptor characteristic of a GaAsP type phototransistor used in the wrist-worn portable electronic device shown in FIGS. 1A and 1B.

FIG. 24 is a circuit diagram of the sensor unit configured separate from the main unit and the connector piece that connects this sensor unit with the main unit in the wrist-worn portable electronic devices of the second and third embodiments of the invention.

FIG. 25 is a cross section showing the structure of the connector member on the sensor unit side of the connector piece in the wrist-worn portable electronic device of the second embodiment of the invention.

FIG. 26 is a cross section showing the structure of the connector member on the sensor unit side of the connector piece in the wrist-worn portable electronic device of the third embodiment of the invention.

FIG. 27 is a circuit diagram of the sensor unit configured separate from the main unit and the connector piece that connects this sensor unit with the main unit in the wrist-worn portable electronic device of the fourth embodiment of the invention.

FIGS. 28A and 28B are explanatory diagrams showing the structure of the connector piece that makes up the connector mechanism in the wrist-worn portable electronic devices of the fifth and sixth embodiments of the invention.

FIG. 29 is an explanatory diagram showing the structure of the connector member that makes up the connector mechanism in the wrist-worn portable electronic devices of the fifth and sixth embodiments of the invention.

FIG. 30 is an explanatory diagram showing the relationship of the electrical connections in the connector member and the circuit for detecting short circuits in the connector member in the wrist-worn portable electronic devices of the fifth and sixth embodiments of the invention.

FIGS. 31A to 31D are explanatory diagrams showing the method for testing the resistance to short-circuiting and the recoverability from short circuits when the connector piece shown in FIGS. 28A and 28B are connected to the connector member shown in FIG. 29.

DESCRIPTION OF THE PREFERRED EMBODIMENTS

First Embodiment

Overall Configuration

FIGS. 1A and 1B are explanatory diagrams showing how the wrist-worn portable electronic device (wrist-worn pulse wave measuring device) of this embodiment is used. In the explanation of this embodiment, a reference to a position of a certain time on the device indicates only a position on the main unit and does not mean that the display on the main unit is a hand type display.

In FIGS. 1A and 1B, wrist-worn portable electronic device 1 of this embodiment comprises main unit 10 (main unit) having a wrist watch structure, cable 20 connected to this main unit 10, and sensor unit 30 disposed on the end of cable 20. Main unit 10 has a wrist band 12 that wraps around the wrist from the 12 o'clock position on the watch and is secured at the 6 o'clock position, and main unit 10 can be freely attached to and removed from the wrist by means of this wrist band 12. Sensor unit 30 is attached to the base of the finger by sensor attachment band 40 which is about 10 mm wide.

Configuration of the Main Unit

FIG. 2 is a plan view showing the main unit of the wrist-worn portable electronic device of this embodiment with the wrist band, cable, etc., removed. FIG. 3 is a bottom plan view of this main unit. FIG. 4 is an explanatory diagram showing this main unit from the 6 o'clock direction, and FIG. 5 is a side view of the main unit from the 3 o'clock direction.

In FIG. 2, main unit 10 has a plastic watch case 11, and a liquid-crystal display device 13 (display member) that digitally displays the pulse and other pulse wave information in addition to the current time and date is disposed on the front side of this watch case 11. Data processing circuit 50 that performs signal processing of the detection signals in order to display changes, etc., in the pulse based on detection results (pulse wave signal) from sensor unit 30 is built into watch case 11, and information display means 60 is configured from this data processing circuit 50 and liquid-crystal display device 13. Also, since a clock circuit is also included in data processing circuit 50, information display means 60 can also display the regular time, lap times, split times, etc., on liquid-crystal display device 13. Button switches 111–115 for setting the time, switching the display mode, etc., are disposed around the outside of watch case 11. Switch 112 is used to switch between the time mode and the pulse measurement mode. Also, button switches 116, 117 are disposed on the front surface of watch case 11. Switch 116 is a lap time switch. Switch 117 is a start/stop switch for starting and stopping the pulse measurement.

The power source of wrist-worn portable electronic device 1 is battery 59 disposed inside of watch case 11, and cable 20 supplies power from battery 59 to sensor unit 30 as well as inputs detection results from sensor unit 30 to data processing circuit 50 inside watch case 11. The object disposed toward 9 o'clock on the watch from battery 59 is piezoelectric element 58 for generating notification sounds.

As can be seen from FIG. 2 and FIG. 3, the width-wise length of watch case 11 is utilized to dispose flat battery 59 used as the power source and flat piezoelectric element 58 used a buzzer side by side inside watch case 11. Therefore, main unit 10 can be made thin. Also, as shown in FIG. 4, the structure can be configured such that battery cover 118 can be removed and battery 59 exchanged by the user himself. Of the electronic components, relatively heavy battery 59 is disposed in a position displaced in the 3 o'clock direction with respect to center position C of main unit 10. In contrast, relatively light piezoelectric element 58 is disposed in a position displaced in the 9 o'clock direction with respect to center position C. Therefore, center of gravity position G in the 3 o'clock and 9 o'clock direction of main unit 10 is displaced in a position in the 3 o'clock direction with respect to center position C, and since wrist band 12 is attached toward the side this center of gravity is shifted, main unit 10 can be worn on the wrist in a stable condition. Analog circuit board 501 and digital circuit board 502 which make up data processing circuit 50 are displaced on the front surface of piezoelectric element 58 and battery 59 and liquid-crystal display device 13 is displaced on this front surface. Further, cover glass 131 covers the front surface of liquid-crystal display device 13.

In FIG. 5, linkage member 105 for holding shaft 121 to which the end of wrist band 12 is attached is formed at the 12 o'clock position on the watch on the outside edge of watch case 11 of main unit 10. Holder 106, to which is attached fastener 122 for holding wrist band 12 wrapped around the wrist and folded back at an intermediate position lengthwise at the intermediate position, is disposed at the 6 o'clock position on the watch.

The part extending from the edge of flat rear surface 119 to which battery cover 118, etc., is attached down to holder 106 in the 6 o'clock direction on the watch on main unit 10 is rotation stop member 108 bent at an angle of about 115 degrees. That is, when main unit 10 is affixed to the wrist by means of wrist band 12, rear surface 119 of main unit 10 fits snugly against the top of the wrist while rotation stop member 108 of main unit 10 comes in contact with the front side of the wrist, and therefore main unit 10 will not slip around the wrist in the direction of either arrow A or arrow B.

Structure for Preventing Rotation of Main Unit

Linkage member 171 for holding shaft 17 to which the end of wrist band 12 is attached is formed at the 12 o'clock position on the outside edge of watch case 11. Holder 18 to which fastener 62 is attached is disposed at the 6 o'clock position on the outside edge of watch case 11, and fastener 62 holds wrist band 12 wrapped around the wrist at an intermediate position.

The part extending from the edge of flat rear surface 119 to which battery cover 118, etc., is attached down to holder 18 in the 6 o'clock direction on main unit 10 is rotation stop member 108 formed as a single unit with watch case 11 and bent at an angle of about 115 degrees with respect to rear surface 119. Therefore, when wrist-worn portable electronic device 1 of this embodiment is worn by means of wrist band 12 so that main unit 10 is positioned on the top surface L1 (side toward back of hand) of a right or left wrist L (arm), rear surface 110 of watch case 11 is in close contact with the top surface L1 of the wrist L while rotation stop member 108 is in contact with the side surface L2 on the radius R side of the arm. In this condition, rear surface 119 of main unit 10 feels like it is straddling the radius R and ulna U of the arm with the skin in between them, while the curved part of rotation stop member 108 and rear surface 119 is disposed opposite the radius R of the arm.

Since rotation stop member 108 and rear surface 119 form an anatomically ideal angle of about 115 degrees, even if main unit 10 is rotated in the direction of arrow A, i.e., main unit 10 is rotated around the wrist L from the front toward the back, rotation stop member 108 remains in contact with the side surface L2 of the wrist L and does not move any further. If main unit 10 is moved in the opposite direction in the direction of arrow B, i.e., main unit 10 is rotated around the wrist L toward the front, rear surface 119 of main unit 10 will remain in contact with the top surface L1 of the wrist L and will not move any further. Also, since main unit 10 is not completely in contact around the wrist L and there is a suitable gap between it and the surface of the wrist L, comfort is not sacrificed even with rotation stop member 108. Further, rotation is only restricted at two locations on one side around the wrist by rear surface 119 and rotation stop member 108. Therefore, even if the wrist is thin, rear surface 119 and rotation stop member 108 are securely in contact with the wrist and prevention of rotation is achieved, while there is no tight feeling even if the wrist is thick.

Rotation of main unit 10 around the wrist can be prevented by setting the angle formed by rear surface 119 and rotation stop member 108 to between about 105 degrees and about 125 degrees. Also, wrist-worn pulse wave detection device 1 may be worn so that main unit 10 is positioned on the bottom surface L3 (side toward palm) of the wrist L, in which case rotation stop member 108 of main unit 10 will come in contact with the side surface L4 toward the ulna side of the arm. Even in this condition, main unit 10 will not rotate unnecessarily if force is applied in the direction of either arrow A or arrow B.

Structure for Securing Sensor FIG. 6A is a plan view of the optical unit of the sensor unit used in the wrist-worn portable electronic device of this embodiment. FIG. 6B is a plan view showing the band for securing the sensor of the sensor unit used in this wrist-worn portable electronic device in the open position, and FIG. 6C is an explanatory diagram showing the structure of a different sensor unit.

Again in FIG. 1, sensor unit 30 comprises sensor attachment band 40 and optical unit 300. Sensor attachment band 40 comprises a plastic molded part having a flexible thickness, and when spread out from a curled condition and wrapped around the base of the finger, its ability to return to its own shape holds it around the base of the finger when let go.

In about the middle of sensor attachment band 40, it is thicker and has a hole 41 capable of housing optical unit 300.

In FIG. 6A, optical unit 300 has an outer casing formed from plastic in a square shape with a pair of protrusions 311, 312 on both sides, and a cable is led out from the inside of optical unit 300.

In FIG. 6B, hole 41 of sensor attachment band 40 is of a shape and size in which optical unit 300 can be inserted, and it also has notches 411, 412 into which protrusions 311, 312 fit when optical unit 300 is inserted. Therefore, optical unit 300 will not fall out of sensor attachment band 40. Sensor attachment band 40 has four constricted locations 410 to facilitate attachment to the finger.

Since the hand can lightly grip even if sensor unit 30 is attached to the base of the finger, the width of sensor attachment band 40 can be about 20 mm with no problem. Also, as shown in FIG. 6C, the width of that part of sensor attachment band 40 to which optical unit 300 is attached can be slightly wider.

Another Structure for Securing the Sensor

FIGS. 7A and 7B are explanatory diagrams showing the use of a different sensor attachment band in the wrist-worn portable electronic device of this embodiment.

In FIGS. 7A and 7B, sensor unit 30 comprises optical unit 300 and sensor attachment band 40A which is separate from this unit. Sensor attachment band 40A is an elastic type that can be stretched, but since it has an inner layer of sponge rubber, it continues to block light even though it stretches when placed on the finger. Also, since sensor attachment band 40A is an elastic type, optical unit 300 is pressed against the finger with the appropriate force by just placing a unit of the appropriate size on the finger.

Configuration of the Sensor Unit

In FIG. 8, optical unit 300 includes lid 302 placed on sensor frame 301, which serves as the case, and has a space inside for housing parts. A light-transmission window is formed on the top surface of sensor frame 301 from glass plate 304 (filter). Circuit board 305 is disposed inside sensor frame 301 such that it faces glass plate 304. LED 31 (light-emitting diode/light-emitting element/semiconductor element), phototransistor 32 (photoreceptor element/semiconductor element), transistors and other electronic components are mounted on circuit board 305, and the light-emitting surface and photoreceptor surface of LED 31 and phototransistor 32, respectively, face glass plate 304.

In this embodiment, a blue InGaN (indium-gallium-nitrogen) type LED is used as LED 31, and as shown in FIG. 9, its light-emitting spectrum has a light-emitting peak at 450 nm and its light-emitting wavelength band is from 350 nm to 600 nm. In order to conform with LED 31 with this light-emitting characteristic, this embodiment uses a GaAsP (gallium-arsenic-phosphorus) type phototransistor as phototransistor 32, and the main range of sensitivity of the photoreceptor wavelength range of the element itself is from 300 nm to 600 nm as shown in FIG. 10. The range of sensitivity of GaAsP phototransistors also extends below 300 nm. A sensor can also be used as phototransistor 32 wherein a filter is affixed to the element, and the main range of sensitivity of the photoreceptor wavelength range of this sensor unit, for example, would be in the 400 nm to 550 nm range. Since the power consumption of LED 31 and phototransistor 32 is relatively small, the continuous operating time is long even if the clock function and pulse wave measurement function are driven with one small battery as in wrist-worn portable electronic device 1 of this embodiment.

Again, in FIG. 8, optical unit 300 is fixed in place such that glass plate 304 faces the finger surface, and therefore the light-emitting surface and photoreceptor surface of LED 31 and phototransistor 32, respectively, face the surface of the finger. Therefore, when light is irradiated from LED 31 toward the finger, phototransistor 32 receives the light reflected back from the body (blood vessels), and when optical unit 300 inputs the received result (pulse wave signal) to main unit 10 via cable 20, the pulse is obtained from the pulse wave signal in main unit 10.

Configuration of the Data Processing Circuit

As shown in the block diagram in FIG. 12 of some of the functions of the data processing circuit configured inside the watch case, in data processing circuit 50, pulse wave signal converter 51 converts the signal input from sensor unit 30 via cable 20 and outputs a pulse wave signal to memory 52. Pulse wave signal memory 52 is RAM that stores pulse wave data converted to a digital signal. Pulse wave signal operator unit 53 reads the signal stored in pulse wave signal memory 52 and performs frequency analysis (fast Fourier transformation), the result of which is input to pulse wave component extraction unit 54. Pulse wave component extraction unit 54 discriminates the pulse wave component from the output signal (spectrum) of pulse wave signal operator unit 53, extracts it and outputs it to pulse count operator unit 55. This pulse count operator unit 55 calculates the pulse count from the frequency component of the input pulse wave, and the result is output to liquid-crystal display device 13.

Configuration of the Connector Mechanism

FIG. 13 is an enlargement of the connector piece attached to the connector member looking from the 3 o'clock direction.

In order to make it possible to handle wrist-worn portable electronic device 1 of this embodiment as a regular watch for daily use, cable 20 and sensor unit 30 are configured such that they can be connected and disconnected at the surface on the edge at the 6 o'clock position on the watch of main unit 10. That is, in FIG. 13, of the edges on main unit 10, connector member 70 is disposed on the surface of the part extended as rotation stop member 108 in the 6 o'clock direction on the watch, and connector piece 80 (connector piece) disposed on the end of cable 20 is configured such that it can be attached and detached to and from it.

In the connector mechanism that utilizes this connector member 70 and connector piece 80, the electrical connection between connector member 70 and connector piece 80 is as shown in FIG. 14.

In FIG. 14, terminals 751 to 756 (first terminal group) are disposed in connector member 70 disposed on the side of main unit 10. Electrodes 831 to 836 (second terminal group) are disposed in connector piece 80 such that they correspond to these terminals 751 to 756. Of these, terminal 752 is a plus terminal for supplying the second drive voltage VDD to LED 31 via electrode 832. Terminal 753 is a terminal that is made the minus potential of LED 31 via electrode 833. Terminal 754 is a terminal for supplying the constant voltage VREG for drive to the collector terminal of phototransistor 32 via electrode 834. Terminal 751 is a terminal for inputting the signal from the emitter of phototransistor 32 via electrode 831. Terminal 755 is a terminal for inputting the signal for detecting whether or not connector piece 80 is connected to connector member 70 via electrode 835. Electrode 836 is configured such that it shields electrodes 831 to 836 by using VDD as a ground when sensor unit 30 is grounded to the body and terminal 756 and electrode 836 are electrically connected.

In connector piece 80, first capacitor C1 (capacitance element) and first switch SW1 are inserted between the terminals (between electrodes 832, 833) of LED 31. This switch SW1 goes to a closed state when connector piece 80 is detached from connector member 70 and first capacitor C1 becomes connected in parallel with LED 31, and when connector piece 80 is connected to connector member 70, switch SW1 goes to an open state. Similarly, second capacitor C2 (capacitance element) and second switch SW2 are inserted between the terminals (electrodes 831, 834) of phototransistor 32. This switch SW2 goes to a closed state when connector piece 80 is detached from connector member 70 and second capacitor C2 becomes connected in parallel with phototransistor 32, and switch SW2 goes to an open state when connector piece 80 is connected to connector member 70.

The configuration of the connector mechanism that connects and disconnects connector piece 80 to and from connector member 70 in this manner is explained by referring to FIGS. 15A and 15B to 18.

FIGS. 15A and 15B show the configuration of the connector piece disposed at the end of the cable. FIG. 16 is an enlargement of the connector member on the main unit. FIG. 17 is a cross section showing the connector piece attached to the connector member, and FIG. 18 is an explanatory diagram showing the layout of each electrode and the circuit pattern on the connector piece.

In FIGS. 15A and 15B, pair of protrusions 81, 82 is formed on both sides of bottom side 801 of connector piece 80 such that they extend down. Four latching members 811, 812, 821, 822 (second protrusions for latching) protrude toward the inside on the end of these protrusions 81, 82.

Six electrodes 831, 832, 833, 834, 835, 836 (second terminal group) are formed on bottom surface 801 of connector piece 80, and around them are formed circular protrusions 841, 842, 843, 844, 845, 846. Here, when connector piece 80 is connected to connector member 70, connector piece 80 is slid in the direction of arrow Q after placing connector piece 80 over connector member 70 as described below, and electrodes 831 to 836 are formed in two rows comprising electrodes 831, 832, 833 and electrodes 834, 835, 836, respectively, in the direction of sliding (direction of arrow Q). In both rows, all of electrodes 831 to 836 are disposed diagonally such they are shifted in a direction crossing the sliding direction (direction of arrow Q) of connector piece 80.

Further, two moving pins 837, 838 that switch the circuit for preventing the effect of static electricity when cable 20 is connected to main unit 10 are disposed on the bottom surface of connector piece 80. As in the explanation below of the connection structure referring to FIG. 17, these moving pins 837, 838 are in a state in which their ends protrude from bottom surface 801 when connector piece 80 is removed from connector member 70.

As shown in FIG. 16, latching members 71, 72, 73, 74 (first protrusion group for latching) protruding toward the outside are formed on the sides of connector member 70 of main unit 10. Therefore, connector piece 80 can be connected to connector member 70 as described below. First, protrusions 81, 82 of connector piece 80 are positioned on the outside of latching members 71, 72, 73, 74 of connector member 70, and also connector 80 is placed over connector member 70 such that latching members 811, 821 of connector piece 80 are positioned between latching member 71 and latching member 72 and between latching member 73 and latching member 74. Next, connector piece 80 is pushed toward connector member 70 such that latching members 811, 821 pass between latching member 71 and latching member 72 and between latching member 73 and latching member 74, respectively (first operation for attaching connector piece 80 to connector member 70). Following this, connector piece 80 is slid (second operation for attaching connector piece 80 to connector member 70) in the direction of arrow Q (attachment direction of connector piece 80; direction from 6 o'clock toward 12 o'clock on main unit 10). As a result, latching members 811, 821 slide under latching members 71, 73. Also, latching members 812, 822 slide under latching members 72, 74. Therefore, since latching members 811, 821, 812, 822 hold latching members 71, 72, 73, 74 between themselves and bottom surface 801 of connector piece 80, respectively, connector piece 80 can be easily and reliably connected to connector member 70.

Here, as with electrodes 831 to 836, terminals 751 to 756 are formed in two rows comprising terminals 751, 752, 753 and terminals 754, 755, 756 along the sliding direction (direction of arrow Q) of connector piece 80. Also, as with electrodes 831 to 836, all of terminals 751 to 756 are disposed diagonally in both rows such they are shifted in a direction crossing the sliding direction (direction of arrow Q) of connector piece 80. Therefore, when connector piece 80 is attached to connector member 70, the six terminals 751 to 756 connect electrically with the six electrodes 831 to 836, whereby it becomes possible to input the measurement results obtained in sensor unit 30 to main unit 10 via cable 20.

When connector piece 80 is removed from connector member 70, however, connector piece 80 is slid back in the direction of arrow R. As a result, latching members 811, 821 return to where they are positioned between latching member 71 and latching member 72 and between latching member 73 and latching member 74. Therefore, by just lifting connector piece 80 up, connector piece 80 can be removed from connector 70 simply and reliably.

In this way, latching mechanism 700 is configured such that when connector piece 80 is slid on connector member 70, they become latched and connector piece 80 is held on connector member 70 in an attached condition, and also when connector piece 80 is slid in the opposite direction (direction of arrow R) from this condition, the latched condition is released. The latching mechanism of this configuration assures reliable latching with few parts.

Configuration of Stopper Mechanism

As can be seen from FIG. 16, vertical walls 711, 721, 731, 741 are formed on the side of latching members 71 to 74 in the direction of arrow Q as seen from the side. Therefore, when connector piece 80 is attached to connector member 70, latching members 811, 812, 821, 822 come in contact with vertical walls 711, 721, 731, 741 as connector piece 80 is slid in the direction of arrow R (second operation), and connector piece 80 stops at the attachment position on connector member 70. Therefore, vertical walls 711, 721, 731, 741 function as the first stoppers for connector piece 80.

When connector piece 80 is slid in the direction of arrow R in order to remove it from connector member 70, latching members 811, 821 come in contact with the back sides of vertical walls 721, 741 of latching members 72, 74 and connector piece 80 is stopped at the original position on connector member 70. Therefore, the back sides of vertical walls 721, 741 function as the second stoppers for connector piece 80.

For this reason, the user can easily attach and detach connector piece 80 to and from connector member 70 without looking. Also, since the user will not accidentally use excessive force, connector 70, etc., will not be damaged.

Structure of Terminals and Electrodes

In connector member 70, terminals 751 to 756 are all positioned in holes 761, 762, 763, 764, 765, 766 formed in connector member 70, and FIG. 17 shows a cross section cut along the position where terminals 753, 756 of these, moving pin 838 and electrodes 833, 836 are formed.

In FIG. 17, connector piece 80 has a structure wherein cover 806 covers outside case 805 capable of housing circuit board 85 inside it. Holes 863, 866 are formed in cover 806, and circular protrusions 843, 846 are formed along the edge of the opening on the lower side. Electrodes 833, 836 are positioned on the inside of holes 863, 866. Electrode 833 is fixed in place by screw 881. Electrode 836 is fixed in place by being sandwiched between circuit board 85 and cover 806. Water proof packing is affixed around electrodes 833, 836. Electrodes 833, 836 are electrically connected to the circuit pattern on circuit board 85 disposed inside connector piece 80. This electrode structure is applicable to electrodes 831, 832, 834, 835 as well as electrodes 833, 836. The wires in cable 20 are electrically connected to the circuit pattern on circuit board 85 by soldering.

Configuration of Click Mechanism

Connector member 70 is configured such that cover 706 covers the recessed area. Holes 763, 766 are formed in cover 706. Terminals 753, 756 are disposed as moving pins in these holes 763, 766 and are capable of moving in and out such that their ends protrude from holes 763, 766. Since coil springs 773, 776 are disposed on collar members 783, 786 formed on the base end of terminals 753, 756, terminals 753, 756 are pushed in a direction by these coil springs 773, 776 such that they protrude from holes 763, 766. Since the outside diameters of collars 783, 786 are larger than the inside diameter of holes 763, 766, terminals 753, 756 will not fall out of holes 763, 766. This terminal structure is applicable to terminals 751, 752, 754, 755 as well as terminals 753, 756.

When connector piece 80 is attached to connector member 70 in a terminal structure configured in this manner, connector piece 80 slides on connector member 70, and therefore terminals 753, 756 ride up on circular protrusions 843, 846 while being pushed by coil springs 773, 776, thus making sure contact with electrodes 833, 836. Since protrusions 843, 846, terminals 753, 756 and coil springs 773, 776 are used as is to make up the click mechanism, connector piece 80 can be reliably attached to connector member 70. In contrast to this embodiment, this click mechanism may comprise terminals that use moving pins disposed on connector piece 80 and protrusions disposed on connector member 70.

Configuration of Switch Mechanism

Hole 868 is formed in cover 806 of connector piece 80. Moving pin 838 is disposed in this hole 838. This moving pin 838 is disposed in hole 868 in a movable condition such that its end protrudes from hole 868. Switch spring 88, which is a flat spring, is disposed on collar member 898 formed on the base of moving pin 838. End member 885 of switch spring 88 pushes on moving pin 838 in the direction that causes it to protrude from hole 868. Since the outside diameter of collar 898 is larger than the inside diameter of hole 868, moving pin 838 will not fall out of hole 868. The base of switch spring 88 is fixed to the top surface of electrode 833 by spring 881, thus electrically connecting it to electrode 833.

In FIG. 18, contact member 886, which comes in contact with the base of moving pin 838, is formed on the end of switch spring 88, and contact 887 is formed on the part extending from the side. This contact 887 is electrically connected to circuit pattern 852 on circuit board 85. This circuit pattern 852 is not included in the figure, but it is inserted between first capacitor C1 and electrode 833.

Therefore, moving pin 838 is pushed by switch spring 88 and its end protrudes from hole 868 as shown in FIG. 17 when connector piece 80 is removed from connector member 70, and in this condition contact 887 of switch spring 88 becomes electrically connected to the circuit pattern 852 of circuit board 85. That is, in FIG. 14, first switch SW1 closes and first capacitor C1 becomes electrically connected to LED 31 in parallel in conjunction with the movement of moving pin 838 indicated by the arrow. Therefore, even if something with a high potential due to static electricity should come in contact with electrodes 832, 833, that charge is stored in first capacitor C1 and LED 31 is not damaged.

In contrast to this, when connector piece 80 is attached to connector member 70, moving pin 838 moves in the direction in which it draws down into hole 868 as indicated by the two-dot chain line in FIG. 17, thus changing the shape of switch spring 88 as indicated by the two-dot chain line. When switch spring 88 changes like this, contact 887 rises up from circuit pattern 852 on circuit board 85, thus cutting the electrical connection. Therefore, in FIG. 14, when connector piece 80 is attached to connector member 70, first switch SW1 becomes open, thus resulting in a circuit configuration that facilitates measurement of the pulse wave. Moreover, even if a charge is stored in first capacitor C1, since this charge is not discharged through electrodes 832, 833, and terminals 752, 753, none of the circuits housed in connector member 70 and main unit 10 are damaged.

While having a simple configuration, this switch mechanism is reliably linked to the attachment of connector piece 80 to connector member 70.

A switch mechanism with this configuration is also employed for the phototransistor as shown in FIG. 14, but this configuration, as shown in FIG. 18, utilizes moving pin 837 and switch spring 89 in the same way as the switch mechanism for LED 31, and therefore its explanation will be omitted here.

Configuration of Connector Cover

FIGS. 19A and 19B are explanatory diagrams showing the configuration of connector cover 90 attached to connector member 70 in place of connector piece 80 when cable 20 and sensor unit 30 are removed from wrist-worn portable electronic device 1 and it is used as a regular wrist watch. This connector cover 90 differs from connector piece 80 in that, since it does not require electrodes, a sensor circuit, or a cable, it is thin overall and it is shaped such that it does not detract from the appearance when attached to connector member 70. However, its attachment structure for connector member 70 is configured the same as connector piece 80. That is, pair of protrusions 91, 92 is formed on both sides of bottom side 901 of connector cover 90 such that they extend down. Four latching members 911, 912, 921, 922 (second protrusions for latching) protrude toward the inside on the end of these protrusions 91, 92. Also, protrusions 941 to 946 are formed on bottom surface 901 of connector cover 90 corresponding to the positions where terminals 751 to 756 of connector member are disposed. Therefore, protrusions 941 to 946 and terminals 751 to 756 make up a click mechanism like that described above.

When attaching connector cover 90 to connector member 70, connector cover 90 is placed on connector member 70 such that latching members 911, 921 of connector cover 90 are positioned between latching member 71 and latching member 72 and between latching member 73 and latching member 74 as when attaching connector piece 80, after which connector cover 90 is pushed down on connector member 70 so that latching members 911, 921 pass through latching member 71 and latching member 72 and between latching member 73 and latching member 74. When connector cover 90 is slid in the direction of arrow Q (direction from 6 o'clock to 12 o'clock on main unit 10) following this, latching members 911, 921 slide under latching members 71, 73. Also, latching members 912, 922 slide under latching members 72, 74. As a result, latching members 911, 921, 912, 922 hold latching members 71, 72, 73, 74 between them and bottom surface 901 of connector cover 901. Also, terminals 751 to 756 of connector member 70 ride up on protrusions 941 to 946 and perform a click action. In this way, connector cover 90 becomes attached to connector member 70.

Operation

The operation of wrist-worn portable electronic device 1 configured in this manner is simply explained by referring to FIGS. 1A and 1B and FIG. 8.

First, in FIGS. 1A and 1B, when wrist-worn portable electronic device 1 is used as a regular wrist watch, main unit 10 is affixed to the wrist using wrist band 12 with cable 20 and sensor unit 30 detached from connector member 70 of main unit 10. At this time, connector cover 90 shown in FIGS. 19A and 19B are attached to connector member 70, whereby appearance is improved and connector member 70 is protected.

When wrist-worn portable electronic device 1 is used to measure the user's pulse while running, after connecting connector piece 80 to connector member 70 and connecting cable 20 to main unit 10, main unit 10 is affixed to the wrist using wrist band 12. Also, after placing glass plate 304 of optical unit 300 against the finger using sensor attachment band 40, then the user starts running.

In this condition, when LED 31 irradiates light toward the finger and this light arrives at blood vessels, some is absorbed by hemoglobin in the blood and some is reflected. The light reflected from the finger (blood vessels) is received by phototransistor 32, and the change in the amount of light received corresponds to the change in the amount of blood caused by the pulse wave of the blood. That is, when there is much blood, the reflected light weakens, and when there is little blood, the reflected light strengthens. Therefore, by monitoring the change in the intensity of reflected light using phototransistor 32, the pulse, etc., can be detected. In order to perform this detection, the signal input from phototransistor 32 (sensor unit 30) is converted to a digital signal in data processing circuit 50 shown in FIG. 12, and this digital signal undergoes frequency analysis, etc., to calculate the pulse. Also, the pulse sought by calculation is displayed in liquid-crystal display device 13. In other words, wrist-worn portable electronic device 1 functions as a pulse meter.

Again, in FIG. 8, part of the light emitted from LED 31 passes through the finger as indicated by arrow C and arrives at the blood vessels, and the light reflected back from the hemoglobin in the blood arrives at phototransistor 32 as indicated by arrow D. The amount of light received via this path is the body-reflected amount. Also, some of the light emitted from LED 31 is reflected by the surface of the finger as indicated by arrow E and arrives back at phototransistor 32. The amount of light received via this path is the skin-reflected amount. Further, some of the light emitted from LED 31 and reflected from the blood vessels is either absorbed or dispersed inside the finger and does not return to phototransistor 32.

Since LED 31 with a light-emitting wavelength range of 350 nm to 600 nm and phototransistor 32 with a photoreceptor wavelength range of 300 nm to 600 nm are used in sensor unit 30, body information is displayed based on detection results obtained in the overlapping wavelength range from about 300 nm to about 600 nm. By using sensor unit 30, of the light included in the external light, light with a wavelength of less than 700 nm does not arrive at phototransistor 32 (photoreceptor member) because the finger acts as a light guide while light with a wavelength of less than 300 nm is almost completely absorbed at the skin surface. Therefore, the detection results are not affected by external light, and therefore body information can be measured from detection results in the wavelength range from about 300 nm to about 600 nm based only on light from the light-emitting member. Since pulse wave information can be obtained without any influence from external light, LED 31 can have a light-emitting wavelength range from 300 nm to 700 nm, and phototransistor 32 can have a photoreceptor wavelength range less than 700 nm.

Principal Effectiveness of the Embodiment

As described above, in wrist-worn portable electronic device 1 of this embodiment, a connector mechanism (connector member 70 and connector piece 80) is provided that facilitates switching of cable 20 extending from sensor unit 30 between a condition wherein it is connected to main unit 10 and a condition wherein it is disconnected from main unit 10. Therefore, since sensor unit 30 and cable 20 can be removed from main unit 10, it can be conveniently used as a regular wrist watch. Here, connector member 70 is configured on the surface of the edge at the 6 o'clock position of the watch. That is, it is disposed on the surface of the edge on the side where wrist band 12 connects to main unit 10. Therefore, since connector member 70 does not protrude from main unit 10 in the 3 o'clock direction on the watch, the wrist can be moved freely. Also, since connector member 70 does not protrude from main unit 10 in the either the 3 o'clock or 9 o'clock directions on the watch, the user's hand will not interfere with connector member 7 even if he should fall. Therefore, while being safe for the user, connector member 70 will not become damaged, for this reason, and high reliability can be maintained even while improving ease of use by employing a structure that connects sensor unit 30 or other external device to main unit 10 via a connector mechanism.

Further, since connector member 70 and connector piece 80 are reliably joined by a latching mechanism that utilizes latching members 71, 72, 73, 74 and latching members 811, 812, 821, 822, the cable will not come off even while running. Therefore, wrist-worn portable electronic device 1 of this embodiment can measure the pulse wave during running without worry and still be conveniently used as a regular watch.

This effect is obtained even if connector member 70 is disposed in the 12 o'clock direction on the watch, but since connector member 70 is disposed in the 6 o'clock direction on the watch in this embodiment, connector member 70 is positioned on the front, thus making it easy to connect and disconnect cable 20.

Further, the switch mechanism is configured such that moving pins 837, 838 are used to electrically connect first and second capacitors C1, C2 to LED 31 and phototransistor 32 in parallel when connector piece 80 is removed from connector member 70 and such that the above electrical parallel connection is released when connector piece 80 is connected to connector member 70 and measurement of the pulse wave becomes possible. Therefore, even if electrodes 831, 832, 833, 834 are exposed in connector member 80, LED 31 and phototransistor 32 will not be damaged by static-electricity. For this reason, high reliability is maintained even if ease of use is improved by employing a structure that connects sensor unit 30 or other external device to main unit 10 via a connector mechanism.

Also, terminals 751 to 756 and electrodes 831 to 836 are disposed in two rows along the direction in which connector piece 80 slides, and since their positions are shifted between each of the terminals and each of the electrodes in a direction that crosses this sliding direction, non-corresponding terminals 751 to 756 and electrodes 831 to 836 do not come in contact even when connector piece 80 is slid on connector member 70. Moreover, even if the surface area is small on which connector member 70 is formed, since the terminals and electrodes are disposed in positions separated from each other, terminals or electrodes will not easily short-circuit even if water should enter between connector piece 80 and connector member 70. Since terminals 752, 754, 756 and electrodes 832, 834, 836 on which the drive voltage is applied are particularly disposed away from each other, tracking will not occur between terminals or electrodes of differing potentials even if water should enter between connector piece 80 and connector member 70. Therefore, an excess voltage will not be applied to either LED 31 or phototransistor 32.

Further, in wrist-worn portable electronic device 1 of this embodiment, the light-emitting wavelength range of LED 31 is from 350 nm to 600 nm. and the principal range of sensitivity of the photoreceptor wavelength range of phototransistor 32 is from 300 nm to 600 nm. The photoreceptor wavelength range when a unit that combines a filter with the element is used as phototransistor 32 is from 400 nm to 550 nm. Therefore, as shown in FIGS. 1A and 1B and FIG. 8. even if the wave pulse is measured under a simple shielded condition, since the finger acts as a light guide, that light included in the external light with a wavelength of less than 700 nm does not arrive at phototransistor 32 (photoreceptor member) as described below, and only that light with a wavelength that does not affect detection passes through the finger acting as a light guide. Therefore, even though light strikes the exposed part of the finger, the external light does not affect the detection results of the pulse wave in this embodiment, and therefore a sensor unit 30 that shields the detection member with a narrow sensor attachment band 40 can be used. For this reason, it is still possible to grip with the hand even if compact sensor unit 30 of this embodiment is attached to the base of the finger, thus not interfering with running. Also, with sensor unit 30 attached at the base of the finger, cable 20 can be short, and therefore cable 20 will not interfere with running. That makes wrist-worn portable electronic device 1 of this embodiment suited to measuring the pulse, etc., during running. In measurements of body heat from the palm to the end of the fingers, the temperature at the base of the finger drops relatively little compared to the marked drop in temperature at the end of the finger. That is, even when it is cold, blood flow at the base of the finger will not drop significantly. Therefore, with sensor unit 30 attached at the base of the finger, the pulse can be accurately measured even when running outside on a cold day.

Further, since light with wavelengths from about 300 nm to about 700 nm is used to obtain pulse wave information, the S/N ratio of the pulse wave signal based on the change in the amount of blood is high.

These reasons are explained below.

First, the reason why there is little influence from external light is explained by referring to FIG. 20A. FIG. 20A shows the relationship between the wavelength of light and the light transmittance of the skin. In this figure, line a shows the light transmittance for light with a wavelength of 200 nm. Line b shows the light transmittance for light with a wavelength of 300 nm. Line c shows the light transmittance for light with a wavelength of 500 nm. Line d shows the light transmittance for light with a wavelength of 700 nm. Line e shows the light transmittance for light with a wavelength of 1 μm.

As can be seen from this figure, of the light contained in external light, that light with a wavelength of less than 700 nm tends not to pass through the finger, and therefore even if that part of the finger not covered by sensor attachment band 40 is irradiated with external light, it does not pass through the finger and arrive at phototransistor 32 as indicated by the dotted line X in FIG. 8. For this reason, by using light with a wavelength of less than 700 nm as in this embodiment, the effect of external light can be suppressed by covering only a minimum necessary area and not having to cover much of the finger, thus making it possible to use wrist-worn portable electronic device 1 of this embodiment outdoors. Since light with a wavelength of less than 300 nm is almost entirely absorbed at the skin surface, even though the wavelength range of received light is less than 700 nm, the wavelength range of received light is essentially from 300 nm to 700 nm.

When an LED with a light-emitting peak near 880 nm and a silicon type phototransistor are used, however, the wavelength range of received light is from 350 nm to 1200 nm as shown in FIG. 21. Therefore, since the pulse wave is detected in prior art optical systems (detection devices) based on detection results obtained using external light with a wavelength of 1 μm, which readily arrives at the photoreceptor member via the finger as a light guide as indicated by arrow Y in FIG. 8, i.e., light indicated by line e in FIG. 20A, errors will readily occur due to fluctuations in the external light.

Below, the reason why the S/N ratio of the pulse wave signal is high in wrist-worn portable electronic device 1 of this embodiment is explained by referring to FIG. 20B. FIG. 20B is an explanatory diagram showing the relationship between the light wavelength and absorption by the various types of hemoglobin.

In FIG. 20B, the absorption of hemoglobin not combined with oxygen is indicated by curve Hb, and the absorption of hemoglobin that has combined with oxygen is indicated by curve $HbO_2$. As indicated by these curves, hemoglobin in the blood has a high absorption coefficient for light with wavelengths from 300 nm to 700 nm, which is several times to several hundred times greater than the absorption coefficient for light with a wavelength of 880 nm, which was used as detection light in the prior art. Therefore, by using light with wavelengths (300 nm to 700 nm) that have a high absorption coefficient to match the absorption of hemoglobin, the detection value changes with good sensitivity to the change in blood, and therefore the detection ratio (S/N ratio) of the pulse wave based on the change in the amount of blood is high.

As shown in FIG. 22, a GaP type LED whose main light-emitting wavelengths range from 540 nm to 570 nm and a GaAsP type phototransistor whose sensitivity ranges from 200 nm to almost 700 nm can be used as the optical units.

Second Embodiment

FIG. 24 is a circuit diagram of the sensor unit configured separate from the main unit and the connector member that connects this sensor unit with the main unit in the wrist-worn portable electronic device (wrist-worn pulse wave measuring device) of this embodiment. This embodiment and the third and fourth embodiments are essentially the same as the first embodiment, and therefore an explanation of the main unit, cable, etc., will be omitted here.

In FIG. 24, sensor unit 30B is configured, as in the first embodiment, such that it is electrically connected to data processing circuit 50B of main unit 10B (main unit) via terminals 801B, 802B, 803B (connector terminals on sensor unit 30B) of connector mechanism 100B and terminals 111B, 112B, 113B (connector terminals on main unit 10B). Sensor unit 30B is a photoelectric detection type pulse sensor, and in sensor circuit 300B, light emitted from LED 31 (light-emitting diode/light-emitting element/ semiconductor element) irradiates tissue inside the finger or other part of the body, and the scattered light is received by phototransistor 32 (photoreceptor element/semiconductor element).

LED 31 is connected in series to a resistor 316B for current limiting, and it is biased via connector mechanism 10 by a power source (not shown) built into main unit 10. LED 31 and phototransistor 32 are disposed several millimeters apart, and by bringing them lightly in contact with the surface of the finger or other part of the body as shown in FIG. 8, the light beam emitted from LED 31 is scattered by capillaries, etc., in the tissue and enters phototransistor 32. By this means, changes in the amount of incident light accompanying the expansion and contraction of the capillaries caused by blood coming from the heart is detected as changes in the photoelectric current flowing to phototransistor 32.

This change in the photoelectric current is converted to a change in voltage by load resistance 317B and is then sent to data processing circuit 50B in main unit 10. Data processing circuit 50B comprises a low-frequency filter which discriminates the pulse wave signal, an amplifier, waveform generating circuit, etc., and outputs a pulse signal. The pulse count of this signal is counted by a counter circuit not show in the figure, and after the period or frequency is measured from this count value, this value is converted to the pulse. The pulse is then displayed in the display member (not shown) disposed in main unit 10.

Also, main unit 10B includes a clock function and a memory for the pulse measurement result, and when sensor unit 30 is not connected, it can be used as a regular watch. Here, when connecting sensor unit 30B to main unit 10B from a disconnected condition between sensor unit 30B and main unit 10B (pulse non-measurement condition), or when discharge of static electricity occurs in sensor unit 30B caused by the putting on or taking off of clothes, there is a danger phototransistor 32 and LED 31 may be damaged by the static electricity because of their particular susceptibility to static electricity.

Here, as described below, damage to sensor circuit 300B disposed in sensor unit 30B due to static electricity is prevented in this embodiment. That is, capacitors C3, C4 (capacitance elements) are disposed in each circuit (circuit contained in LED 31 and circuit contained in phototransistor 32) in sensor unit 30B. However, since switch mechanisms 131B, 132B are configured for these capacitors C3, C4, capacitors C3, C4 are electrically connected to LED 31 and phototransistor 32 in parallel when switch mechanisms 131B, 132B are closed, and this state is canceled when switch mechanisms 131B, 132B are open.

Here, switch mechanisms 131B, 132B open and close automatically in conjunction with the operation that connects sensor unit 30B to main unit 10B via connector mechanism 100B and the operation that disconnects sensor unit 30B from main unit 10B. It is also possible to open and close switch mechanisms 131B, 132B manually. Therefore, when sensor unit 30B is not connected to main unit 10B (when not measuring pulse), switch mechanisms 131B, 132B are closed, and therefore capacitors C3, C4 are electrically connected to the circuits of sensor unit 30B in parallel. In this state, the overall capacitance of the circuits in sensor unit 30B is increased by capacitors C3, C4, and therefore even if static electricity should discharge into terminals 801B, 802B, 803B of sensor unit 30B, the instantaneous transfer of an excessive charge can be prevented. Therefore, it is possible to protect sensor circuit 300B of sensor unit 30B from static electric damage. Phototransistor 32 and LED 31, in particular, are relatively susceptible to static electricity as compared to other circuit elements due to their structure, and therefore this static electricity countermeasure has significant effect.

When connecting sensor unit 30B to main unit 10B from this state, switch mechanisms 131B, 132B are still in a closed state, and therefore even when terminals 801B, 802B, 803B on sensor unit 30B and terminals 111B, 112B, 113B on main unit 10B are connected to each other, capacitors C3, C4 are electrically connected to phototransistor 32 and LED 31 in parallel as when sensor unit 30B is not connected to main unit 10B. For this reason, static electricity can be flowed to the main unit 10B side.

Following this, when terminals 801B, 802B, 803B and terminals 111B, 112B, 113B are connected to each other in connector mechanism 100B and switch mechanisms 131B, 132B are in an open state, capacitors C3, C4 are electrically cut off, thus facilitating detection of the pulse wave signal. Moreover, since capacitors C3, C4 are electrically cut off, there is no problem with a drop in the ability to detect the pulse wave signal or a drop in the drive power. Therefore, sensor unit 30B can detect changes in blood flow in body tissue with high sensitivity.

In this way, when the connection between sensor unit 30B and main unit 10B is released in connector mechanism 100B, switch mechanisms 131B, 132B are used to electrically connect capacitors C3, C4 to LED 31 and phototransistor 32 in parallel, and when sensor unit 30B and main unit 10B are connected in connector mechanism 100B, the above electrical, parallel connection is released, thus facilitating measurement of the pulse wave, whereby, even if terminals 801B, 802B, 803B of sensor unit 30B are exposed in connector mechanism 100B, LED 31 and phototransistor 32 will not be damaged by static electricity. For this reason, high reliability is maintained and ease of use is improved by employing a structure that connects sensor unit 30B or other external device to main unit 10B via connector mechanism 100B.

A more specific configuration for realizing a method to prevent damage due to static electricity is explained by referring to FIG. 25.

FIG. 25 is a cross section showing the structure of the connector member on the sensor unit side of the connector mechanism of the wrist-worn portable electronic device of this embodiment.

In the figure, terminals 831B, 832B, 833B on sensor unit 30B are moving pins (retracting pins) supported inside the holes formed in case 170B, and they are pushed in the direction in which their ends protrude by conductive springs 814B, 815B, 816B. Case 170B comprises an upper lid and a main body. Since case 170B is made from plastic or other insulative material, circuit block 180B and hollow ring-shaped conductive plates 190B, 200B are insulated. Conductive springs 814B, 815B, 816B are electrically connected to the pattern formed in circuit block 180B, and therefore the sensor circuit disposed in circuit block 180B and terminals 831B, 832B, 833B are electrically connected.

Here, magnets 211B, 212B are affixed to the edge of case 170B, and magnets 211B, 212B adhere to the magnetic plate (not shown) affixed to the connector member on main unit 10B, thus linking sensor unit 30B and main unit 10B. This is how connector mechanism 100B is configured.

Conductive spring 814B is connected to conductive plate 190B via the pattern on circuit block 180B, capacitor C3 and lead terminal 240B. Similarly, conductive spring 815B is connected to conductive plate 200B via capacitor C4 and through lead terminal 250B. In a conductive state in the connector member configured like this, terminals 832B, 833B are pushed up by conductive springs 815B, 816B and are connected to conductive plates 190B, 200B, respectively. Therefore, in this state, terminal 831B and terminal 832B are electrically connected via conductive spring 814B, the pattern on circuit block 180B, capacitor C3, lead terminal 240B and conductive plate 190B. Similarly, terminal 832B is connected to terminal 833B with capacitor C4 in a connected state. This corresponds to the closed state of switch mechanisms 131B, 132B in FIG. 24. For this reason, even if there should be a static electric discharge on sensor unit 30B in this state, static electric damage is prevented as described above because capacitors C3, C4 are connected to sensor circuit 300B in parallel.

Also, when sensor unit 30B is connected to main unit 10B in order to measure the pulse, first, with terminals 831B, 832B, 833B being pushed up by conductive springs 814B, 815B, 816B (capacitors C3, C4 are connected in parallel because switch mechanisms 131B, 132B are in a closed state), terminals 831B, 832B, 833B are connected to the terminals on main unit 10B and any static electricity is discharged. Therefore, static electric damage is prevented in sensor unit 30B.

Next, sensor unit 30B is connected to main unit 10B by magnets 211B, 212B adhering to the magnetic plate on main unit 10B. As a result, terminals 831B, 832B, 833B are pushed down by terminals 111B, 112B, 113B on main unit 10B, thus depressing conductive springs 814B, 815B, 816B. By this means, the electrical connections between conductive plates 190B, 200 and terminals 832B, 833B are released, thus separating capacitors C3, C4 from the circuit. In this state, pulse measurement is enabled, thus corresponding to the open state of switch mechanisms 131B, 132B in FIG. 24.

Next, when pulse measurement is completed and sensor unit 30B is removed, terminals 831B, 832B, 833B are pushed up by conductive springs 814B, 815B, 816B again until they come in contact with conductive plates 190B, 200B. That is, in FIG. 24, switch mechanisms 131B, 132B go to an ON state; i.e., capacitors C3, C4 become connected and establish a state wherein the function that prevents damage due to static electricity is manifested.

Third Embodiment

The third embodiment is explained by referring to FIG. 26. FIG. 26 is a cross section showing the structure of the connector member on the sensor unit of the connector mechanism of the wrist-worn portable electronic device (wrist-worn pulse wave measuring device) of this embodiment.

Since the basic configuration of the sensor unit of the wrist-worn portable electronic device of this embodiment is generally the same as the configuration of the sensor unit in the second embodiment, parts with common functions are designated by the same numbers and their descriptions are omitted.

In this embodiment, the connector member on the sensor unit 30 has magnetic reed switches 271B, 272B. Of these magnetic reed switches, one terminal of magnetic reed switch 271B is connected to conductive spring 814B via lead wire 291B and the pattern on circuit block 180B, and the other terminal is connected to capacitor C3 via lead wire 291B and the pattern on circuit block 180B and also to conductive spring 815B via the pattern on circuit block 180B. Therefore, terminal 831B and terminal 832B are electrically connected via magnetic reed switch 271B and capacitor C3. Similarly, terminal 832B and terminal 833B are electrically connected via magnetic reed switch 272B and capacitor C4.

When sensor unit 30B is removed from main unit 10B in the connector member configured in this manner, magnetic reed switches 271B, 272B become closed due to the leakage flux from magnets 211B, 212B. Therefore, capacitors C3, C4 become electrically connected to the circuit. This state corresponds to the closed state of switch mechanisms 131B, 132B in FIG. 24 and is a state that prevents damage due to static electricity.

In this embodiment, as well, when sensor unit 30B is connected to main unit 10B, the adherence of the magnetic plate (not shown) to main unit 10B and magnets 211B, 212B is utilized. Therefore, when sensor unit 30B is connected to main unit 10B the leakage flux of magnets 211B, 212B stops and magnetic reed switches 271B, 727B go to an open state. Therefore, capacitors C3, 1223 are separated from the circuit, thus facilitating pulse measurement.

Fourth Embodiment

The fourth embodiment is explained by referring to FIG. 27.

FIG. 27 is a circuit diagram of the sensor unit configured separately from the main unit and connector member that connects this sensor unit to the main unit.

The basic configuration of sensor unit 30B in the wrist-worn portable electronic device of this embodiment is generally the same as the configuration of sensor unit 30B in the wrist-worn portable electronic device of the second embodiment or the third embodiment. Therefore, corresponding parts are indicated by the same numbers and their descriptions are omitted.

In this embodiment, diode 261B is connected to LED 31 in parallel and in reversed polarity. Similarly, diode 262B is connected to the photoreceptor element phototransistor 32 in parallel. By means of these electrical connections, diodes 261B, 262B prevent excessive reverse voltage from flowing to LED 31 and phototransistor 32. The structures of the other circuits and the connector members are the same as the embodiments described above.

When sensor unit 30B is not connected to main unit 10B, switch mechanisms 131B, 132B become closed and capacitors C3, C4 become electrically connected to each circuit in parallel as in the second and third embodiments.

If a discharge of static electricity should occur in this state due to the taking on or off of clothing, the static electricity is temporarily stored in capacitors C3, C4. Since the overall capacitance of the sensor unit 30B circuit is increased by capacitors C3, C4 at this time, the instantaneous transfer of an excessive charge is prevented, thus preventing damage to LED 31 and phototransistor 32 due static electricity.

Further, since diodes 261B, 262B are connected to LED 31 and phototransistor 32 in parallel in this embodiment, the flow of an excessive reverse current to LED 31 and phototransistor 32, which are particularly susceptible to static electricity, is prevented due to rectification by diodes 261B, 262B. By preventing this excessive reverse current, it is possible to more reliably prevent damage to LED 31 and phototransistor 32 due to static electricity.

When the pulse is measured, switch mechanisms 131B, 132B are opened and capacitors C3, C4 are separated from sensor circuit 300B as in the second and third embodiments, and therefore the pulse wave signal can be measured. Moreover, since capacitors C3, C4 are electrically cut off, there is no problem with a drop in the ability to detect the pulse wave signal or a drop in the drive power. Therefore, sensor unit 30B can detect changes in blood flow in body tissue with high sensitivity.

In this way, when the connection between sensor unit 30B and main unit 10B is released in connector mechanism 100B, switch mechanisms 131B, 132B are used to electrically connect capacitors C3, C4 to LED 31 and phototransistor 32 in parallel, and when sensor unit 30B and main unit 10B are connected, the above electrical, parallel connection is released, thus facilitating measurement of the pulse wave. Therefore, even if terminals 801B, 802B, 803B are exposed in the sensor unit 30B side of connector mechanism 100B, LED 31 and phototransistor 32 will not be damaged by static electricity. For this reason, high reliability is maintained even if ease of use is improved by employing a structure that connects sensor unit 30B or other external device to main unit 10 via connector mechanism 100B.

Modifications of Second to Fourth Embodiments In the second to the fourth embodiments, a light-emitting diode was used in sensor unit 30B, but it is possible to measure the pulse wave without using a light-emitting diode. That is, sun light, incandescent light or other external light is used, and this scattered light is detected by the phototransistor. In this case, the only semiconductor element that requires protection from static electricity is phototransistor 32, which is a photoreceptor element, thus simplifying the configuration of sensor unit 30B.

Also, in the second to the fourth embodiments, sensor unit 30B contains only an LED and a phototransistor, but various circuits can be added in addition to these. Examples of these include a temperature measurement circuit that uses a thermistor, a humidity measurement circuit that uses a dew sensor, a pressure sensor circuit that measures the pressure between the sensor and the body, a power supply circuit that supplies power to the sensor, etc., and a display circuit that displays the sensor state, etc.

Further, the second to the fourth embodiments described a portable electronic device that detects the pulse wave, but the invention is not limited to these. For example, this invention is applicable to thermometers, etc., that utilize the temperature sensitivity of semiconductor if they are wrist-worn portable electronic devices that use a semiconductor element, which is susceptible to static electricity, as sensor unit 30B.

Further, the switch mechanisms, the semiconductor protection circuit that uses diodes, and other configurations in the second to the fourth embodiments can also be applied to the first embodiment.

Fifth Embodiment

The wrist-worn portable electronic device (wrist-worn pulse wave measuring device) of this embodiment and the sixth embodiment described below have basically the same configuration as the first embodiment and only the connector member is different. Therefore, components with common functions are indicated by the same numbers and their explanations are omitted, while only the connector member is described here.

Structure of Electrode Surfaces of Connector Pieces

FIGS. 28A and 28B are explanatory diagrams of the connector pieces that make up the connector mechanism in the wrist-worn portable electronic device of this embodiment.

In FIGS. 28A and 28B, six electrodes 831, 832, 833, 834, 835, 836 (second terminal group) are formed on bottom surface 801 of connector piece 80 in this embodiment, as well, and circular protrusions 841, 842, 843, 844, 845, 846 are formed around these. Here, as described above, when connector piece 80 is connected to connector member 70, connector piece 80 is slid in the direction of arrow Q after placing connector piece 80 on connector member 70, and electrodes 831 to 836 are formed in two rows of electrodes 831, 832, 833 and electrodes 834, 835, 836 in this sliding direction (direction of arrow Q). Also, in both rows, electrodes 831 to 836 are each disposed diagonally such that they are shifted in a direction that crosses the sliding direction of connector piece 80 (direction of arrow Q).

Area 802 around positions where electrodes 831, 832, 833 are formed and area 802 around positions where electrodes 834, 835, 836 are formed on bottom surface 801 of connector piece 80 have undergone hydrophobic treatment so that the contact angle of water is greater than 85 degrees. In contrast, area 803 surrounding area 802 around the terminals has undergone hydrophilic treatment so that the contact angle of water is less than about 75 degrees or more desirably less than about 35 degrees.

The types of hydrophilic treatments that can be used around electrodes 831 to 836 include the application of a hydrophilic sheet containing a surfactant and plasma treatment of the surface of the plastic from which connector piece 80 itself is configured. Possible hydrophobic treatments include the application of a fluorine-based coating material, application of a paint and the application of a hydrophobic tape. Since the contact angle of water in area 802 around the terminals need only be larger than the contact angle of water in surrounding area 803, then if connector piece 80 itself is configured from plastic with a relatively high hydrophobic characteristic, then only surrounding area 803 need undergo hydrophilic treatment. On the other hand, if connector piece 80 is configured from an ABS plastic that has already undergone hydrophilic treatment by graft polymerization of an acrylic or other type of monomer with a hydrophilic characteristic on the ABS plastic surface, then only area 802 around the terminals need undergo hydrophobic treatment.

Here, the results of comparisons of the contact angle on polycarbonate plastics used to make connector member 70 and connector piece 80, after each of the hydrophobic and hydrophilic treatment methods has been performed (measured values and their means), and after application of finger prints to demonstrate durability (measured values and their means) are shown in TABLE 1. The application of finger prints was approximated by applying a fatty oil (the fatty acid glycerol ester).

TABLE 1

Unit: degrees

| Treatment Name | | Contact Angle | | | Mean | After finger prints | Mean |
| --- | --- | --- | --- | --- | --- | --- | --- |
| Hydrophobic treatment | MCF-323L (Dainihon Ink) | 80.1 | 90.0 | 85.0 | 85.0 | 61.2 | 61.8 | 61.5 |
| | FR-108 (Dainihon Ink) | 106.8 | 107.2 | 107.6 | 107.2 | 89.9 | 98.5 | 94.2 |
| | Modipa F200 (Nihon Yushi) | 100.6 | 101.2 | 102.8 | 101.5 | 83.5 | 85.2 | 84.4 |
| | Saitop (Asahi Glass) | 98.4 | 96.6 | 96.6 | 96.0 | 73.5 | 77.8 | 75.6 |
| Hydrophobic tape | Nitofuron (Nitto Denko) | 93.7 | 99.4 | 101.4 | 98.2 | 54.8 | 52.9 | 53.9 |
| | Nafuron (Nichi Asu) | 95.0 | 97.6 | 99.1 | 97.2 | 70.2 | 66.2 | 68.2 |
| | ASF-110 (Chuko Kasei) | 97.3 | 95.2 | 96.7 | 96.4 | 62.2 | 69.8 | 66.0 |

TABLE 1-continued

Unit: degrees

| Treatment Name | | Contact Angle | | | Mean | After finger prints | | Mean |
|---|---|---|---|---|---|---|---|---|
| Hydrophilic treatment | Hydrophilic sheet (PR Topura) | 12.3 | 17.3 | 12.7 | 14.1 | 5.2 | 6.2 | 5.7 |
| | Graft polymerization (on ABS) | 29.9 | 33.7 | 33.4 | 32.3 | 26.5 | 26.3 | 26.4 |
| | Yupiron + plasma treatment | 75.8 | 82.2 | 67.6 | 75.1 | 46.6 | 50.9 | 48.8 |
| Material | Yupiron (Mitsubishi Gasu Kagaku) | 81.5 | 85.0 | 83.4 | 83.3 | 41.6 | 45.9 | 43.8 |
| | Polycarbonate (Teijin) | 86.9 | 85.6 | 88.1 | 86.9 | 50.1 | 50.7 | 50.4 |

As shown in TABLE 1, the contact angle changes with each type of treatment, but when coated with the product Saitop made by Asahi Glass after hydrophobic treatment, the surface demonstrated particularly superior durability when beat. Also, of each of the hydrophilic treatments, ABS plastic that has undergone hydrophilic treatment by graft polymerization of the ABS plastic surface with an acrylic or other type of monomer with a hydrophilic characteristic demonstrates superior wear resistance.

Structure of Terminal Surface of Connector Members

In this embodiment, connector member 70 is disposed at the 6 o'clock position on main unit 10, and as with terminals 831 to 836, terminals 751 to 756 disposed here are each formed in two rows comprising terminals 751, 752, 753 and terminals 754, 755, 756 along the sliding direction (direction of arrow Q) of connector piece 80. Also, in both rows, as with terminals 831 to 836, terminals 751 to 756 are each disposed diagonally in both rows such that they are shifted in a direction that crosses the sliding direction (direction of arrow Q) of connector piece 80. Therefore, when connector piece 80 is connected to connector member 70, the six terminals 751 to 756 electrically connect to the six terminals 831 to 836, thus making it possible to input the measured results of sensor unit 30 to main unit 10 via cable 20.

When connector piece 80 is removed from connector member 70, connector piece 80 is slid back in the direction of arrow R. As a result, latching members 811, 821 return 'to where they are positioned between latching member 71 and latching member 72 and between latching member 73 and latching member 74. Therefore, by just lifting up connector piece 80, connector piece 80 can be easily and reliably removed from connector member 70.

In this way, latching mechanism 700 is configured such that connector piece 80 and connector member 70 become latched when connector piece 80 is slid on connector member 70 in the direction of arrow Q and they become unlatched when connector piece 80 is slid in the opposite direction (direction of arrow R) from this condition. The latching mechanism with this configuration latches reliably with few parts.

Also, when connector piece 80 is slid on connector member 70 in the direction from 6 o'clock toward 12 o'clock, the force applied to main unit 10 is in a direction that main unit 10 will not rotate easily due to rotation stop member 108. Therefore, main unit 10 will not slip around the wrist when connector piece 80 is connected, thus simplifying connection.

Area 702 around positions where terminals 751 to 756 are formed on top surface 701 of connector member 70 has undergone hydrophobic treatment so that the contact angle of water is greater than 85 degrees. In contrast, area 703 surrounding area 702 around the terminals has undergone hydrophilic treatment so that the contact angle of water is less than about 75 degrees or more desirably less than about 35 degrees.

The types of hydrophilic treatments that can be used around electrodes 751 to 756 include, as in the case of connector piece 80, the application of a hydrophilic sheet containing a surfactant and plasma treatment of the surface of the plastic from which connector member 70 itself is configured. Possible hydrophobic treatments include the application of a fluorine-based coating material, application of a paint and the application of a hydrophobic tape. Since the contact angle of water in area 702 around the terminals need only be larger than the contact angle of water in surrounding area 703, then if connector member 70 itself is configured from plastic with a relatively high hydrophobic characteristic, then only surrounding area 703 need undergo hydrophilic treatment. On the other hand, if connector member 70 is configured from an ABS plastic that has already undergone hydrophilic treatment by graft polymerization of an acrylic or other type of monomer with a hydrophilic characteristic on the ABS plastic surface, then only area 702 around the terminals need undergo hydrophobic treatment.

Configuration of Short-Circuit Detection Means

Even in the connector mechanism comprising connector member 70 and connector piece 80 configured in this manner, electrical connection between connector member 70 and connector piece 80 is performed, as shown in FIG. 30, the same way as in the first embodiment. However, in main unit 10, the short-circuit detection mechanism for detecting whether or not a short circuit has occurred between terminals or between electrodes due to water entering between connector piece 80 and connector member 70 when they are connected is disposed in data processing circuit 50. That is, in FIG. 30, when the sensor drive signal causes switching to the pulse wave measurement mode by LED 31 and phototransistor 32, the potential of terminals 753, 751 is detected based on the signals input in sequence from terminals 753, 751 (signal input terminals from LED 31 and phototransistor 32) to multiplexer 56 via A/D converter 57 (pulse wave signal converter 51), and it is determined from this potential level whether or not there is a short circuit between terminal 753 (electrode 833) and terminal 752 (electrode 832) for applying the second drive voltage VDD on LED 31 and whether or not there is a short circuit between terminal 751 (electrode 831) and terminal 754 (electrode 834) for applying the constant voltage VREG on phototransistor 32. Also, this detection result is displayed on liquid-crystal display device 13.

Principal Effectiveness of the Embodiment

When connector piece 80 is connected to connector member 70 such that it covers it in wrist-worn portable electronic device 1 configured in this manner, top surface 701 of connector member 70 and bottom surface 801 of connector piece 80 oppose each other with a narrow gap between them. Therefore, when water comes in contact with the connectors, capillary action causes water to penetrate deep into the gap. Here, in wrist-worn portable electronic device 1 of this embodiment, terminals 751 to 756 and electrodes 831 to 836 are disposed in two rows along the sliding direction of connector piece 80, and since each of the terminals and each of the electrodes are shifted diagonally in a direction that crosses this sliding direction, the terminals and electrodes are separated from each other. Therefore, even if water should penetrate between connector piece 80 and connector member 70, it is difficult for the terminals or the electrodes to short-circuit.

Moreover, if a short circuit should occur, it is displayed in liquid-crystal display device 13 of main unit 10, and so it can be judged whether a problem is due to a short circuit. Therefore, a normal condition can be restored by quickly shaking the wrist or performing some other action that will restore a normal condition.

Further, the contact angle of water in area 702 around the positions where terminals 751 to 756 are formed is greater than the contact angle of water in surrounding area 703 on top surface 701 of connector member 70. Also, the contact angle of water in area 802 around the positions where electrodes 831 to 836 are formed is greater than the contact angle of water in surrounding area 803 on bottom surface 801 of connector piece 80. That is, in comparing areas 702, 802 around the terminals with surrounding areas 703, 803, areas 702, 802 around the terminals are hydrophobic, while surrounding areas 703, 803 are hydrophilic. Therefore, even if water should enter in the gap between connector member 70 and connector piece 80, near terminals 751 to 756 and electrodes 831 to 836, water is pulled away from areas 702, 802 around the terminals toward surrounding areas 703, 803. For this reason, short circuits do not readily occur between terminals 751 to 756 and between electrodes 831 to 836. Even if a short circuit should occur, water can be easily removed from the area around terminals 751 to 756 and electrodes 831 to 836 by simply shaking the wrist, thus facilitating easy recovery from a short-circuit condition.

Therefore, even if some rain water should get on wrist-worn portable electronic device 1 of this embodiment, short circuits do not readily occur between terminals, and even if a temporary short circuit should occur, it can be quickly and easily recovered, thus making this device suited to measuring the pulse during running.

Moreover, in the wrist-worn portable electronic device of this embodiment, the contact angle of water in areas 702, 802 around the terminals on opposing top surface 701 and bottom surface 801 of connector member 70 and connector piece 80 is larger than the contact angle of water in surrounding areas 703, 803, and therefore in addition to more reliably preventing short circuits, it is easier to recover from a short-circuit condition.

For example, to compare resistance to short-circuiting and recoverability, the following tests were performed on connector member 70 and connector piece 80 shown in FIGS. 28A, 28B and 29 under the conditions shown in TABLE 2 using sample 1 (main connector unit) wherein area 702 around the terminals on connector member 70 underwent hydrophobic treatment by coating with the Asahi Glass product Saitop, while surrounding area 703 underwent plasma treatment as a hydrophilic treatment, and area 802 around the terminals on connector piece 80 underwent hydrophobic treatment by coating with the Nihon Yushi K.K. product Modipa F200, while surrounding area 803 retained the contact angle of the material (Mitsubishi Gasu Kagaku K.K. product Yupiron:polycarbonate plastic) itself used to make connector piece 80, and sample 2 (main connector unit) wherein area 702 around the terminals on connector member 70 underwent hydrophobic treatment by coating with the Nihon Yushi K.K. product Modipa F200, while a hydrophilic sheet was applied to surrounding area 703, and area 802 around the terminals on connector piece 80 underwent hydrophobic treatment by coating with the Asahi Glass product Saitop, while a hydrophilic sheet was applied to surrounding area 803.

TABLE 2

| Item | Sample | Sample 1 | Sample 2 |
|---|---|---|---|
| At connector member 70: | | | |
| Contact angle in area around terminals (degrees) | | 96.0 | 101.5 |
| Contact angle in surrounding area (degrees) | | 75.1 | 14.1 |
| At connector piece 80: | | | |
| Contact angle in area around terminals (degrees) | | 101.5 | 96.0 |
| Contact angle in surrounding area (degrees) | | 83.3 | 14.1 |
| Resistance (kilohms) between terminals 751, 754 after removal from saltwater | First time | 230 | 680 |
| | Second time | 230 | 1180 |
| | Third time | 240 | 1140 |
| Resistance (kilohms) between terminals 751, 754 3 minutes after removal from saltwater | First time | 740 | 1020 |
| | Second time | 470 | 1300 |
| | Third time | 900 | 1180 |
| Resistance (kilohms) between terminals 751, 754 immediately after removal from saltwater | | 230 | 1490 |
| Resistance (kilohms) between terminals 751, 754 2 minutes after removal from saltwater | | 290 | 1600 |

In sample 1, the contact angle of water in area 702 around the terminals was 96.0 degrees, the contact angle of water in surrounding area 703 was 75.1 degrees, the contact angle of water in area 802 around the terminals was 101.5 degrees, and the contact angle of water in surrounding area 803 was 83.3 degrees. Therefore, in sample 1, the contact angle of water in areas 702, 802 around the terminals was 10 to 25 degrees larger than in surrounding areas 703, 803.

In sample 2, however, the contact angle of water in area 702 around the terminals was 101.5 degrees and the contact angle of water in area 802 around the terminals was 96.0 degrees, while the contact angle of water in surrounding areas 703, 803 was 14.1 degrees. Therefore, the contact angle of water in areas 702, 802 around the terminals in sample 2 was 80 to 85 degrees larger than in surrounding areas 703, 803.

The pitch between terminals and electrodes in samples 1 and 2 was 0.56 mm.

In this evaluation, first main connector units of samples 1 and 2 with the same structure as connector member 70 and connector piece 80 were dipped bottom edge first (edge on side of terminals 751, 754) in a 5% saltwater solution, and then they were pulled out and the resistance between terminal 751 and terminal 754 and the resistance between terminal 751 and terminal 752 were measured immediately. The results showed infinite resistance between any of the terminals, thus confirming there was no short circuit.

Also, after completely dipping main connector units of samples 1 and 2 with the same structure as connector member 70 and connector piece 80 in a 5% saltwater solution, they were taken out and the resistance between terminal 751 and terminal 754 and the resistance between terminal 751 and terminal 752 were measured immediately and after three minutes. The results, as shown in TABLE 2, indicated a drop in the resistance down to several hundred kilohm, indicating a short-circuit condition. However, it was confirmed that the short-circuit condition could be recovered by just pressing tissue paper against the bottom side of the connector member in both samples 1 and 2.

Further, by performing hydrophobic treatment of areas 702, 802 around the terminals and hydrophilic treatment of surrounding areas 703, 803 in this embodiment, the difference between the contact angle of water in these areas is made large in connector member 70 and connector piece 80. For this reason, short circuits do not occur between terminals 751 to 756 and between electrodes 831 to 836. Even if a short circuit should occur, water can be easily removed from near terminals 751 to 756 and electrodes 831 to 836 by just shaking wrist-worn portable electronic device 1, thus facilitating recovery from a short-circuit condition.

For example, to compare resistance to short-circuiting and recoverability, the following tests were performed on connector member 70 and connector piece 80 shown in FIGS. 28A, 28B and 29 under the conditions shown in TABLE 3 using sample 3 (main connector unit) wherein area 702 around the terminals on connector member 70 underwent hydrophobic treatment by coating with the Nihon Yushi K.K. product Modipa F200 and area 802 around the terminals on connector piece 80 underwent hydrophobic treatment by coating with the Asahi Glass product Saitop, while surrounding areas 703, 803 retained the contact angle of the material (Mitsubishi Gasu Kagaku K.K. product Yupiron-:polycarbonate plastic) itself used to make connector member 70 and connector piece 80, and sample 4 (main connector unit) wherein area 702 around the terminals on connector member 70 underwent hydrophobic treatment by coating with the Nihon Yushi K.K. product Modipa F200 and area 802 around the terminals on connector piece 80 underwent hydrophobic treatment by coating with the Asahi Glass product Saitop, while a hydrophilic sheet was applied to surrounding areas 703, 803.

TABLE 3

| | | Sample | |
| --- | --- | --- | --- |
| | | Sample 3 | Sample 4 |
| Item | | Pitch 0.6 | Pitch 0.6　Pitch 0.3 |
| At connector member 70: | | | |
| Contact angle in area around terminals (degrees) | | 101.5 | 101.5 |
| Contact angle in surrounding area (degrees) | | 83.3 | 14.1 |
| At connector piece 80: | | | |
| Contact angle in area around terminals (degrees) | | 96.0 | 96.0 |
| Contact angle in surrounding area (degrees) | | 83.3 | 14.1 |
| Number of times dropped until | 1 | 12/430 | 2/390　3/270 |
| infinite resistance value/ | 2 | 8/410 | 2/430　4/310 |
| resistance (kilohms) when | 3 | 8/430 | 1/390　3/370 |
| removed from saltwater | 4 | 17/440 | 2/430　2/450 |
| | 5 | 12/420 | 1/460　3/410 |
| | 6 | 8/430 | 1/490　2/460 |
| | 7 | 5/450 | 1/900　3/470 |
| | 8 | 7/560 | 2/1000　2/530 |
| | 9 | 14/420 | 2/980　2/510 |
| | 10 | 14/430 | 2/990　2/510 |
| | 11 | 9/340 | 2/960　2/530 |
| | 12 | 10/410 | 2/970　3/540 |
| | 13 | 14/410 | 2/980　2/540 |

TABLE 3-continued

| | | Sample | |
| --- | --- | --- | --- |
| | | Sample 3 | Sample 4 |
| Item | | Pitch 0.6 | Pitch 0.6　Pitch 0.3 |
| | 14 | 8/410 | 2/1000　2/550 |
| | 15 | 6/430 | 2/990　2/560 |
| | 16 | 10/400 | 2/1000　3/560 |
| | 17 | 7/430 | 2/1000　2/870 |
| | 18 | 12/450 | 2/1000　2/890 |
| | 19 | 6/460 | 2/1000　2/900 |
| | 20 | 8/430 | 2/1000　3/850 |
| Number of times dropped until | av | 9.8 | 1.8　2.5 |
| infinite resistance value | σ | 3.2 | 0.4　0.6 |

In sample 3, the contact angle of water in area 702 around the terminals was 101.5 degrees, the contact angle of water in area 802 around the terminals was 96.0 degrees, and the contact angle of water in surrounding areas 703, 803 was 83.3 degrees. Therefore, in sample 3, the contact angle of water in areas 702, 802 around the terminals was 10 to 20 degrees larger than in surrounding areas 703, 803.

In sample 4, however, the contact angle of water in area 702 around the terminals was 101.5 degrees and the contact angle of water in area 802 around the terminals was 96.0 degrees, while the contact angle of water in surrounding areas 703, 803 was 14.1 degrees. Therefore, the contact angle of water in areas 702, 802 around the terminals in sample 4 was 80 to 85 degrees larger than in surrounding areas 703, 803.

In sample 3, the pitch between terminals and between electrodes was 0.6 mm. In sample 4, however, samples with pitches of 0.6 mm and 0.3 mm between terminals and between electrodes were evaluated.

In this evaluation, a main connector unit with the same structure as connector member 70 and connector piece 80 was first completely dipped in a 5% saltwater solution as shown in FIG. 31A, taken out as shown in FIG. 31B, and then repeatedly dropped from a free height of 6 cm as shown in FIG. 31C and FIG. 31D, and the number of times the main connector unit had to be dropped until the resistance between electrode 834 and electrode 835 (between terminal 754 and terminal 755) became infinitely large was counted. The results are shown in TABLE 3.

As shown in TABLE 3, the above test, was repeated 20 times each, and when the mean values were compared, sample 4, wherein areas 702, 802 around the terminals had undergone hydrophobic treatment and surrounding areas 703, 803 had undergone hydrophilic treatment required 1.8 drops to recover from the short-circuit condition in the sample with a 0.6-mm pitch between terminals and between electrodes and 2.5 drops to recover from the short-circuit condition in the sample with a 0.3-mm pitch between terminals and between electrodes. Sample 3, however, wherein the material that made up connector member 70 and connector piece 80 had been improved for areas 702, 802 around the terminals required 9.8 drops to recover from a short-circuit condition, thus requiring more effort for recovery than sample 4.

When samples with the same 0.6-mm pitch between terminals and between electrodes where compared, sample 4 demonstrated a larger resistance than sample 3 immediately after immersion in the 5% saltwater solution: i.e., indicating that a short-circuit condition does not readily occur.

As a result of repeating the evaluation test, it was confirmed that if there was at least a 50-degree difference between the contact angle of water in areas 702, 802 around the terminals and the contact angle of water in surrounding areas 703, 803, then it was notably difficult for a short circuit to occur between terminals and that even if there was a temporary short circuit, it could be easily recovered.

Sixth Embodiment

The fifth embodiment was configured such that the contact angle of water was different in areas 702, 802 around the terminals and in surrounding areas 703, 803 in the initial state, but this embodiment is configured such that it is after a so-called rough grain surface was formed, a fine grain surface was formed, and a lined surface was formed (initial state) and after fatty oil was applied. With respect to the smooth surface that makes up areas 702, 802 around the terminals, we measured the contact angle of water after a smooth surface with a near mirror finish was formed (initial state) and after fatty oil was applied. The measurement results are shown in TABLE 4. Regular polycarbonate plastic and polycarbonate plastic containing fluorine were used as the substrate.

TABLE 4

| Material | Item | | Contact angle of water (degrees) | | | |
|---|---|---|---|---|---|---|
| | | | Mirror surface | Surface with rough grain | Surface with fine grain | Surface with lines |
| Regular polycarbonate | Initial | Mean of measured values | 79.3 | 85.2 | 89.3 | 81.2 |
| | | | 81.4 | 86.3 | 91.1 | 88.6 |
| | | | 81.1 | 86.6 | 95.9 | 86.5 |
| | | | 80.6 | 86.0 | 92.1 | 85.4 |
| | After applying oil | Mean of measured values | 66.0 | 79.2 | 47.1 | 57.8 |
| | | | 71.3 | 54.2 | 48.7 | 58.7 |
| | | | 72.0 | 55.5 | 51.0 | 61.4 |
| | | | 69.8 | 63.0 | 48.9 | 59.3 |
| Polycarbonate containing fluorine | Initial | Mean of measured values | 79.7 | 87.5 | 97.5 | 86.6 |
| | | | 83.4 | 87.7 | 97.9 | 86.2 |
| | | | 83.3 | 85.9 | 98.2 | 87.6 |
| | | | 82.1 | 87.0 | 97.9 | 86.8 |
| | After applying oil | Mean of measured values | 58.7 | 50.1 | 46.3 | 55.6 |
| | | | 63.8 | 49.6 | 43.9 | 55.8 |
| | | | 62.0 | 48.6 | 44.9 | 54.7 |
| | | | 61.5 | 49.4 | 45.0 | 55.4 | difficult for a short circuit to occur between terminals or between electrodes even after repeatedly handling connector member 70 and connector piece 80 by hand.

Since this embodiment has basically the same configuration as the first and fifth embodiments, corresponding components are designated by the same numbers and an explanation of their structure, etc., is omitted, but in this embodiment, bottom surface 801 of connector piece 80 shown in FIGS. 28A and 28B and top surface 701 of connector member 70 shown in FIG. 29 are made of the same material while areas 702, 802 around the terminals have a smooth surface and surrounding areas 703, 803 have a fine rough surface.

In the connector structure of wrist-worn portable electronic device 1 configured in this manner, there is no difference in the contact angle of water between areas 702, 802 around the terminals and surrounding areas 703, 803 in the initial stage, or in contrast to the first embodiment the contact angle of water in areas 702, 802 around the terminals may be slightly smaller than in surrounding areas 703, 803, but when finger prints are adhered to the surface, the contact angle of water in the smooth areas 702, 802 around the terminals will become larger than in surrounding areas 703, 803 which have a rough surface. That is, when a fatty oil (e.g., the fatty acid glycerol ester) is applied to approximate a condition in which finger prints are applied to each area, the contact angle of water is smaller in surrounding areas 703, 803 which have a rough surface than in areas 702, 802 around the terminals which have a smooth surface.

Here, there are various types of rough surfaces, but in this embodiment, we measured the contact angle of water on the rough surface that makes up surrounding areas 703, 803

The results showed that, as can be seen in TABLE 4, the contact angle of water on the rough surfaces was not necessarily smaller on either plastic initially, but when compared after applying the fatty oil, the contact angle of water on the rough surfaces was 10 to 20 degrees smaller than on the mirror surface. Of the rough surfaces, the surface on which a fine grain was formed demonstrated particularly good wettability.

Therefore, it can be said that when oil from the hand adheres to connector member 70 and connector piece 80 as wrist-worn portable electronic device 1 is used, the hydrophobic characteristic in areas 702, 802 around the terminals is enhanced while the hydrophilic characteristic in surrounding areas 703, 803 is enhanced. Even if water should penetrate between connector member 70 and connector piece 80 in this condition, the water will be pulled from areas 702, 802 around the terminals toward surrounding areas 703, 803 in the vicinity of terminals 751 to 756 and electrodes 831 to 836. For this reason, short circuits will not readily occur between terminals 751 to 756 and between electrodes 831 to 836. Also, even if a temporary short circuit should occur, water in the vicinity of terminals 751 to 756 and electrodes 831 to 836 can be easily removed by just shaking the wrist, thus facilitating recovery from a short-circuit condition.

Moreover, by utilizing the presence or absence of roughness to establish a difference in contact angle as in this connector structure, only the mold used to form connector member 70 and connector piece 80 need be treated.

On the surface on which lines were formed, water drops were elongated in the direction along the lines about 10 percent more than in the direction transverse to the lines.

Therefore, by forming circular lines concentric to areas 702, 802 around the terminals, for example, in surrounding areas 703, 803 as a structure that utilizes this anisotropy of wettability, the penetration of water to areas 702, 802 around the terminals can be prevented. In addition to a grain surface or a line surface, a satin finish may be used as the rough surface.

Modifications of the Fifth and Sixth Embodiments

By combining the treatments in the fifth embodiment and the surface types in the sixth embodiment such that the contact angle of water in areas 702, 802 around the terminals is greater than the contact angle of water in surrounding areas 703, 803 both in the initial state and after time (after fatty acid, finger prints have adhered), a connector structure can be realized wherein short-circuits will not occur initially or after time has passed, or even if a short circuit does occur, it can be easily recovered.

Effectiveness of the Invention

As described above, the connector mechanism in the wrist-worn portable electronic device of this invention is disposed in either the 6 o'clock or 12 o'clock direction on the main unit. Therefore, by means of this invention, the wrist-worn portable electronic device can be used as a regular watch in daily use by just disconnecting the cable, etc., from the main unit by means of the connector mechanism. Also, this connector mechanism is disposed on the surface of the edge of the main unit in either the 6 o'clock direction or the 12 o'clock direction on the watch. That is, it is disposed on the surface of the edge where the wrist band is attached to the main unit. Therefore, since the connector mechanism does not protrude from the main unit in the 3 o'clock direction on the watch, the wrist can be moved freely. Also, since the connector mechanism does not protrude from the main unit in either the 3 o'clock or the 9 o'clock direction on the watch, the user's hand will not bump against the connector mechanism should he fall. For this reason, since the connector mechanism will not be damaged as well as being safe for the user, high reliability is maintained and ease of use is enhanced by using a structure that connects a sensor unit or other external device to the main unit via a connector mechanism.

Further, since the connector member and the connector piece are securely latched by a latching mechanism, the cable will not come off inadvertently while running. Therefore, assuming the wrist-worn portable device of this invention is used as a pulse meter, for example, then it can be conveniently used without worry to measure the pulse wave while running as well as being used as a regular watch.

Particularly if the connector member is disposed in the 6 o'clock direction on the watch, then: since the connector mechanism is disposed on the front when the main unit is worn on the wrist, it can be easily connected and disconnected.

When the first terminal group and the second terminal group are disposed in a plurality of rows along the sliding direction of the connector piece and the position of each terminal is shifted in a direction that crosses this sliding direction, terminals that do not correspond with each other will not come in contact when the connector piece is slid on the connector member. Also, since terminals can be separated from each other even if the surface area of the connector member is small, short-circuits between terminals will not occur even if water should penetrate between the connector piece and the connector member.

When the connector mechanism is configured such that the second protrusion group for latching of the connector piece slides under the first protrusion group for latching of the connector member and is held in place, latching is reliable and attachment and detachment are easy with only a few components. Here, by configuring a first stopper mechanism that prescribes the attachment position of the connector piece and a second stopper mechanism that prescribes the slide position when it is removed, the user can easily attach or detach the connector piece to or from the connector member without looking.

Further, when a connector cover having the same mechanism as the latching mechanism is provided that covers the connector member surface in place of the connector piece, the first terminal group is protected while appearance is enhanced when the connector piece is removed and the main unit is used as a regular watch in daily use. When the first or second terminal group is configured as movable pins and these movable pins are pushed by springs in a direction in which they protrude from holes, the electrical connection between the first terminal group and the second terminal group is reliable. Also, when protrusions are formed around the pins that electrically connect with the moving pins, the moving pins ride up on the protrusions when the connector piece is attached to the connector member, thus comprising a simple click mechanism.

When moving pins pushed by springs are disposed in holes in the connector piece, a switch mechanism that is linked to the attachment of the connector piece to the connector member can be easily configured and operation is reliable.

By utilizing this switch mechanism to electrically connect capacitance elements to the light-emitting element and the photoreceptor element in parallel when the connector piece is disconnected from the connector member and to release the electrical connection of the capacitance elements between the terminals when the connector piece is connected to the connector member, it is possible to switch the connection state of the capacitance elements between a standby mode and a pulse wave measurement mode. That is, since the capacitance elements are electrically connected in parallel to the light-emitting element and the photoreceptor element when the connector piece is removed from the connector member, the light-emitting element and the photoreceptor element can be protected from static electricity. For this reason, high reliability is maintained even though ease of use is enhanced by using a structure that connects a sensor unit or other external device to the main unit via a connector mechanism.

When the switch mechanism is configured such that it opens and closes automatically in conjunction with the connection operation of the connector piece and the operation that releases the connection, the connection state of the capacitance elements can be automatically switched between a standby mode and a pulse wave measurement mode, thus providing convenience while reliably protecting the light-emitting element or the photoreceptor element.

When the contact angle of water in the first area around the terminals surrounding the positions where the terminal groups are formed is larger than the contact angle of water in the second area surrounding the first area, in a comparison of the area around the terminals with the surrounding area, the first area has a hydrophobic characteristic while the second area has a hydrophilic characteristic. Therefore, even if water should enter the gap between the connector member and the connector piece, water in the vicinity of the terminals is pulled away from the first area around the terminals toward the second area, thus making it difficult for short circuits to occur between terminals. Even if a short circuit should occur, it is easy to recover from the short-circuit condition by just shaking the connector piece.

When the contact angle of water in the first area around the terminals is larger than the contact angle of water in the surrounding area on both opposing surfaces of the connector member and the connector piece, the occurrence of short circuits can be more reliably prevented and recovery from a short circuit is easier.

Rather than changing the material from which the connector member or the connector piece is configured for either the first area around the terminals or the second area, the difference between the contact angles of water in these areas can be made larger by hydrophobic treatment of the area around the terminals and hydrophilic treatment of the surrounding area, thus more reliably preventing the occurrence of short circuits and making it easier to recover from a short circuit.

When the contact angle of water differs in a condition in which fatty oil is adhered, the contact angle of water in the first area around the terminals is larger than in the second area even when fatty oil (finger prints) is adhered to the connector member and the connector piece, the occurrence of short circuits can be more reliably prevented and recovery from a short circuit is easier.

When the presence and absence of roughness is used to establish a difference in contact angle, the molds used to form the connector member and the connector piece need only be treated.

When this connector mechanism is provided on a wrist-worn portable electronic device, short circuits between terminals do not readily occur even if rain water should get on the connector mechanism, and even if a temporary short circuit should occur, it can be easily recovered by just shaking the wrist, and therefore this device is suited to measuring the pulse wave while running outside.

When a short-circuit detection means is provided on this wrist-worn portable electronic device, it can be judged immediately whether or not the current problem is due to a short circuit, thus making it possible to quickly recover to a normal condition by shaking the wrist or performing some other recovery action.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A wrist-worn portable electronic device, comprising:

a main unit having a display member for displaying information including time;

a wrist band, connected to said main unit, for allowing a user to wear said main unit on a wrist; and a connector for allowing signals to be input to said main unit, said connector comprising:

a connector member disposed on an edge of said main unit at one of a 6 o'clock and a 12 o'clock position of said main unit, said connector member including a first terminal group comprising a plurality of terminals, and a connector piece for removably coupling to said connector member, said connector piece including a second terminal up comprising a plurality of terminals for electrically connecting to said first terminal group, said second terminal group receiving signals for inputting to said main unit;

wherein said connector further includes latching means for attaching said connector piece to said connector member when said connector piece is slid on said connector member in a predetermined sliding direction and holding said connector piece and connector member together in a latched condition, said latching means releasing said connector piece and connector member from the latched condition when said connector piece is slid in an opposite direction from said sliding direction; and wherein on at least a first surface of one of said connector member and said connector piece which faces a second surface of the other one of said connector member and said connector piece, a first area around the terminals of one of said first and second terminal groups is hydrophobic relative to a second area and has as a material characteristic a first contact angle of water, and said second area surrounding said first area is hydrophilic relative to said first area and has as a material characteristic a second contact angle of water that is less than said first contact angle.

2. The electronic device of claim 1 wherein said connector member is disposed on an edge of said main unit at the 6 o'clock position, and said latching means attaches said connector piece and connector member together in said latched condition when said connector piece is slid on said connector member in a direction from said 6 o'clock position to said 12 o'clock position of the main unit.

3. The electronic device of claim 1 wherein said first terminal group is disposed in a plurality of rows at an angle to said sliding direction, and said second terminal group is disposed in a plurality of rows at an angle to said sliding direction such that the position of said second terminal group corresponds to the position at which said first terminal group is disposed when said connector piece and connector member are attached in the latched condition.

4. The electronic device of claim 1 wherein said latching means comprises:

a first protrusion group, connected on said connector member, for latching, said first protrusion group including a plurality of protrusions disposed such that at least two protrusions project outward from said connector member in a 3 o'clock direction of the main unit, and at least two protrusions project outward from said connector member in a 9 o'clock direction of the main unit;

a pair of protruding members connected to said connector piece and each protruding down from one side of said connector piece, said protruding members being positioned outside said first protrusion group when said connector piece is attached to said connector member; and a second protrusion group, connected to said protruding members, for latching, said second protrusion group including a plurality of protrusions disposed such that they protrude inward from said protruding members;

wherein in a latching operation said protruding members of said second protrusion group initially pass between said protruding members of said first protrusion group by a first action that fits said connector piece on said connector member, said protruding members of said second protrusion group subsequently slide to respective positions under said protruding members of said first protrusion group by a second action that slides said connector piece on said connector member in said sliding direction, so that said connector member and said connector piece are coupled together.

5. The electronic device of claim 4 wherein said connector includes:

first stopper means, connected to said connector member, for stopping said connector piece at a first preset position on said connector member when said second action is performed, and second stopper means, connected to said connector member, for stopping said connector piece at a second preset position when said connector piece is moved when an action opposite to said second action is performed, so as to allow said protruding members of said second protrusion group to pass between said protruding members of said first protrusion group when an action opposite from said first action is performed.

6. The electronic device of claim 1 wherein one of said connector piece and said connector member includes through holes on one surface, moving pins movable in said holes and springs attached to said moving pins for pushing said moving pins in said holes to cause ends of said moving pins to protrude from said holes, wherein terminals of said one of said first terminal group and said second terminal group includes said moving pins.

7. The electronic device of claim 6 wherein terminals of or said first and second terminal groups are for electrically connecting to said moving pins and include round protruding members disposed around a position where said moving pins are positioned when said connector piece is attached to said connector member, and wherein said moving pins, said springs and said protruding members of said terminals constitute click means for causing said moving pins to ride up on said protruding members of said terminals during attachment of said connector piece to said connector member.

8. The electronic device of claim 1 wherein said connector piece is a connector cover for attaching to said connector member and covering said connector member.

9. A wrist-worn portable electronic device, comprising:

a main unit having a display member for displaying information including time;

a wrist band, connected to said main unit, for allowing a user to wear said main unit on a wrist; and a connector for allowing signals to be input to said main unit, said connector comprising:

a connector member disposed on an edge of said main unit at one of a 6 o'clock and a 12 o'clock position of said main unit, said connector member including a first terminal group comprising a plurality of terminals, and a connector piece for removably coupling to said connector member, said connector piece including a second terminal group comprising a plurality of terminals for electrically connecting to said first terminal group, said second terminal group receiving signals for inputting to said main unit; and wherein said connector further includes a switch, positioned on said connector piece, for closing and opening a contact in conjunction with attachment and detachment operations of said connector piece on said connector member; and a cable having two ends, one of which is connected to said connector piece;

a sensor unit connected to the other end of said cable, for producing detection results transmitted to said main unit via said cable and said connector piece, said sensor including semiconductor elements; and wherein one of said connector piece and said sensor unit includes a capacitance element for protecting the semiconductor elements of said sensor unit from static electricity when said capacitance element is electrically connected to said semiconductor elements in parallel; and wherein said switch electrically connects in parallel said capacitance element to said semiconductor elements when said connector piece is removed from said connector member, and said switch disconnects said capacitance from parallel connection to said semiconductor elements when said connector piece is attached to said connector member.

10. The electronic device of claim 9 wherein said switch includes:

a plurality of through holes on a surface of said connector piece which faces said connector member when said connector piece and connector member are attached, moving pins for moving in said holes to allow ends of said pins to protrude from said holes, and springs attached to said moving pins for pushing said pins in a direction that causes said moving pins to protrude from said surface of said connector piece, wherein said switch automatically closes and opens a contact in accordance with movement of said moving pins in said holes.

11. The electronic device of claim 9 wherein said connector piece further includes a magnetic reed switch that magnetically detects attachment and detachment of said connector piece to said connector member.

12. The electronic device of claim 1, further comprising:

a cable having two ends, one of which is connected to said connector piece, and a sensor unit, connected to the other end of said cable, for producing detection results transmitted to said main unit via said cable and said connector piece.

13. The electronic device of claim 12 wherein said sensor unit includes:

a light-emitting element for irradiating light toward a body, and a photoreceptor element for detecting light returning from the body and for outputting detection results, and wherein said sensor unit sends the detection results output by said photoreceptor element to said main unit, and said display member of said main unit displays the detection results.

14. The electronic device of claim 9 wherein one of said connector piece and said sensor unit includes a diode for preventing an excessive reverse current from flowing to said semiconductor elements of said sensor unit when said diode is electrically connected in parallel to said semiconductor elements.

15. The electronic device of claim 9 wherein said semiconductor elements of said sensor unit include a light-emitting element for irradiating light toward a body and a photoreceptor element for detecting light returning from the body and for outputting detection results, and wherein said sensor unit sends the detection results output by said photoreceptor element to said main unit, and said display member of said main unit displays the detection results.

16. The electronic device of claim 1 wherein on a second surface of the other one of said connector member and said connector piece, which faces the first surface, a third area around the terminals of the other one of said first and second terminal groups is hydrophobic relative to a fourth area and has as a material characteristic a third contact angle of water, and said fourth area surrounding said third area is hydrophilic relative to said third area and has as a material characteristic a fourth contact angle of water that is less than said third contact angle.

17. The electronic device of claim 1 wherein a difference between said first contact angle of water measured on said first area and the second contact angle of water measured on said second area is greater than about 50 degrees.

18. The electronic device of claim 1 wherein said material characteristic of said first area results from hydrophobic treatment and said material characteristic of said second area results from hydrophilic treatment.

19. The electronic device of claim 1 wherein said first contact angle of water is evaluated with a fatty oil applied on at least said first surface of one of said connector member and said connector piece which faces a second surface of the other one of said connector member and said connector piece.

20. The electronic device of claim 16 wherein said third contact angle of water is evaluated with fatty oil applied on said second surface of the other one of said connector member and said connector piece.

21. The electronic device of claim 19 wherein said first area includes a smooth surface and said second area includes a rough surface.

22. The electronic device of claim 1, further comprising:
a cable having two ends, one of which is connected to said connector piece, and
a sensor unit, connected to the other end of said cable, for producing detection results transmitted to said main unit via said cable and said connector piece, said sensor unit including a light-emitting element for irradiating light toward a body and a photoreceptor element for detecting light returning from the body and for outputting detection results, and
wherein said sensor unit sends the detection results output by said photoreceptor element to said main unit, and said display member of said main unit displays the detection results.

23. The electronic device of claim 22 wherein said sensor unit includes terminals for receiving a drive voltage, and wherein said main unit includes short-circuit detection means for measuring an electric potential of at least the terminals of said first terminal group, and for detecting whether a short-circuit condition exists between the terminals of said first terminal group and the terminals of said sensor unit, and wherein said display member of said main unit displays the detection results.

24. A connector for inputting signals to a wrist-worn portable electronic device which includes a main unit with a display member for displaying information including time, and a wrist band connected to said main unit, said connector comprising:
a connector member disposed on an edge of said main unit at one of a 6 o'clock and a 12 o'clock position of said main unit, said connector member including a first terminal group comprising a plurality of terminals, and
a connector piece for removably coupling to said connector member, said connector piece including a second terminal group comprising a plurality of terminals for electrically connecting to said first terminal group, said second terminal group receiving signals for inputting to said main unit; and latching means for attaching said connector piece to said connector member when said connector piece is slid on said connector member in a predetermined sliding direction and holding said connector piece and connector member together in a latched condition, said latching means releasing said connector piece and connector member from the latched condition when said connector piece is slid in an opposite direction from said sliding direction; and wherein on at least a first surface of one of said connector member and said connector piece which faces a second surface of the other one of said connector member and said connector piece, a first area around the terminals of one of said first and second terminal groups is hydrophobic relative to a second area and has as a material characteristic a first contact angle of water, and said second area surrounding said first area is hydrophilic relative to said first area and has as a material characteristic a second contact angle of water that is less than said first contact angle.

25. The connector of claim 24 wherein said connector member is disposed on an edge of said main unit at the 6 o'clock position, and said latching means attaches said connector piece and connector member together in said latched condition when said connector piece is slid on said connector member in a direction from said 6 o'clock position to said 12 o'clock position of the main unit.

26. The connector of claim 24 wherein said first terminal group is disposed in a plurality of rows at an angle to said sliding direction, and said second terminal group is disposed in a plurality of rows at an angle to said sliding direction such that the position of said second terminal group corresponds to the position at which said first terminal group is disposed where said connector piece and connector member are attached in the latched condition.

27. The connector of claim 24 wherein said latching means comprises:
a first protrusion group, connected on said connector member, for latching, said first protrusion group including a plurality of protrusions disposed such that at least two protrusions project outward from said connector member in a 3 o'clock direction of the main unit, and at least two protrusions project outward from said connector member in a 9 o'clock direction of the main unit;
a pair of protruding members connected to said connector piece and each protruding down from one side of said connector piece, said protruding members being positioned outside said first protrusion group when said connector piece is attached to said connector member; and
a second protrusion group, connected to said protruding members, for latching, said second protrusion group including a plurality of protrusions disposed such that they protrude inward from said protruding members;
wherein in a latching operation said protruding members of said second protrusion group initially pass between said protruding members of said first protrusion group by a first action that fits said connector piece on said connector member, said protruding members of said second protrusion group subsequently slide to respective positions under said protruding members of first protrusion group by a second action that slides said connector piece on said connector member in said sliding direction, so that said connector member and said connector piece are coupled together.

28. The connector of claim 27, further comprising:
first stopper means, connected to said connector member, for stopping said connector piece at a first preset position on said connector member when said second action is performed, and
second stopper means, connected to said connector member, for stopping said connector piece at a second preset position when said connector piece is moved when an action opposite to said second action is performed, so as to allow said protruding members of said second protrusion group to pass between said protruding members of said first protrusion group when an action opposite from said first action is performed.

29. The connector of claim 24 wherein one of said connector piece and said connector member includes through holes on one surface, moving pins movable in said holes and springs attached to said moving pins for pushing said moving pins in said holes to cause ends of said moving pins to protrude from said holes, wherein terminals of said one of said first terminal group and said second terminal group include said moving pins.

30. The connector of claim 29 wherein terminals of one of said first and second terminal groups are for electrically connecting to said moving pins and include round protruding members disposed around a position where said moving pins are positioned when said connector piece is attached to said connector member, and wherein said moving pins, said springs and said protruding members of said terminals constitute click means for causing said moving pins to ride up on said protruding members of said terminals during attachment of said connector piece to said connector member.

31. The connector of claim 24 wherein said connector piece is a connector cover for attaching to said connector member and covering said connector member.

32. A connector for inputting signals to a wrist-worn portable electronic device which includes a main unit with a display member for displaying information including time, and a wrist band connected to said main unit, said connector comprising:
a connector member disposed on an edge of said main unit at one of a 6 o'clock and a 12 o'clock position of said main unit, said connector member including a first terminal comprising a plurality of terminals, and
a connector piece for removably coupling to said connector member, said connector piece including a second terminal group comprising a plurality of terminals for electrically connecting to said first terminal group, said second terminal group receiving signals for inputting to said main unit; and
wherein said connector further includes a switch, positioned on said connector piece, for closing and opening a contact in conjunction with attachment and detachment operations of said connector piece on said connector member; and
a cable having two ends, one of which is connected to said connector Piece;
a sensor unit connected to the other end of said cable, for producing detection results transmitted to said main unit via said cable and said connector piece, said sensor including semiconductor elements; and
wherein one of said connector piece and said sensor unit includes a capacitance element for protecting the semiconductor elements of said sensor unit from static electricity when said capacitance element is electrically connected to said semiconductor elements in parallel; and
wherein said switch electrically connects in parallel said capacitance element to said semiconductor elements when said connector piece is removed from said connector member, and said switch disconnects said capacitance from parallel connection to said semiconductor elements when said connector piece is attached to said connector member.

33. The connector of claim 32 wherein said switch includes:
a plurality of through holes on a surface of said connector piece which faces said connector member when said connector piece and connector member are attached,
moving pins for moving in said holes to allow ends of said pins to protrude from said holes, and
springs attached to said moving pins for pushing said pins in a direction that causes said moving pins to protrude from said surface of said connector piece,
wherein said switch automatically closes and opens a contact in accordance with movement of said moving pins in said holes.

34. The connector of claim 32 wherein said connector piece further includes a magnetic reed switch that magnetically detects attachment and detachment of said connector piece to said connector member.

35. The connector of claim 24, further comprising:
a cable having two ends, one of which is connected to said connector piece, and
a sensor unit, connected to the other end of said cable, for producing detection results transmitted to said main unit via said cable and said connector piece.

36. The connector of claim 35 wherein said sensor unit includes:
a light-emitting element for irradiating light toward a body, and
a photoreceptor element for detecting light returning from the body and for outputting detection results, and
wherein said sensor unit sends the detection results output by said photoreceptor element to said main unit, and said display member of said main unit displays the detection results.

37. The connector of claim 32, further comprising:
a cable having two ends, one of which is connected to said connector piece, a sensor unit connected to the other end of said cable, for producing detection results transmitted to said main unit via said cable and said connector piece, said sensor including semiconductor elements, and
wherein one of said connector piece and said sensor unit includes a capacitance element for protecting the semiconductor elements of said sensor unit from static electricity when said capacitance element is electrically connected to said semiconductor elements in parallel, and
wherein said switch means electrically connects in Parallel said capacitance element to said semiconductor elements when said connector piece is removed from said connector member, and said switch means disconnects said capacitance from parallel connection to said semiconductor elements when said connector piece is attached to said connector member.

* * * * *

UNITED STATES PATENT AND TRADEMARK OFFICE
CERTIFICATE OF CORRECTION

PATENT NO.    : 5,781,511
DATED         : July 14, 1998
INVENTOR(S)   : Naoki Yasukawa, et al.

It is certified that errors appear in the above identified patent and that said Letters Patent is hereby corrected as shown below:

Column 39, line 67, change "up" to --group--.

Column 41, line 28, change "or" to --one of--.

Column 45, line 57, change "Piece" to --piece--.

Column 46, line 58, change "Parallel" to --parallel--.

Signed and Sealed this

Third Day of November, 1998

BRUCE LEHMAN

*Attest:*

*Attesting Officer*          *Commissioner of Patents and Trademarks*